(12) United States Patent
Kamiki

(10) Patent No.: US 7,523,802 B2
(45) Date of Patent: Apr. 28, 2009

(54) SAFE-DRIVING PROMOTION SYSTEM AND SAFE-DRIVING PROMOTION DEVICE

(76) Inventor: Hiroshi Kamiki, 11-1, Honmachi 5-chome, Toyonaka-shi, Osaka 5600021 (JP)

( * ) Notice: Subject to any disclaimer, the term of this patent is extended or adjusted under 35 U.S.C. 154(b) by 118 days.

(21) Appl. No.: 11/794,296

(22) PCT Filed: Jan. 10, 2006

(86) PCT No.: PCT/JP2006/300120

§ 371 (c)(1),
(2), (4) Date: Jun. 27, 2007

(87) PCT Pub. No.: WO2006/075565

PCT Pub. Date: Jul. 20, 2006

(65) Prior Publication Data

US 2008/0041652 A1    Feb. 21, 2008

(30) Foreign Application Priority Data

Jan. 11, 2005  (JP) .................. 2005-003983

(51) Int. Cl.
*B60R 21/01* (2006.01)
*B60R 22/00* (2006.01)
(52) U.S. Cl. .................. 180/272; 180/268; 180/270; 340/576; 340/439; 280/801.1
(58) Field of Classification Search .................. 180/268, 180/270, 271, 272; 340/576, 439; 701/45; 280/801.1
See application file for complete search history.

(56) References Cited

U.S. PATENT DOCUMENTS 6,293,361 B1 * 9/2001 Mueller .................. 180/272

2005/0099310 A1 * 5/2005 Jones .................. 340/576

FOREIGN PATENT DOCUMENTS

| DE | 24 38 642 A1 * | 3/1976 |
|----|----|----|
| JP | 50-79022 | 6/1975 |
| JP | 6-239200 | 8/1994 |
| JP | 3514733 | 1/2004 |
| JP | 2004-284424 | 10/2004 |
| JP | 2005-1572 | 1/2005 |

* cited by examiner

*Primary Examiner*—Ruth Ilan
(74) *Attorney, Agent, or Firm*—Kratz, Quintos & Hanson, LLP

(57) ABSTRACT

An object of the present invention is to provide a safe-driving promotion system for obliging a driver to wear a seat belt and effectively preventing drunk driving and/or drug driving.

The safe-driving promotion system includes attachment sensing means 100 for sensing that a male part 11 of the seat belt of an automobile 1 has been attached to a female part 12, and for outputting a first start permission signal α; start controlling means 200 for receiving the first start permission signal α and putting a motor 20 of the automobile 1 into a startable state; breath component concentration determining means 300 for detecting alcohol contained in the breath of the driver of the automobile 1 and performing concentration determination of the alcohol; and attachment preventing means 400 for preventing the attachment between the male part 11 and the female part 12 of the seat belt. The attachment preventing means 400 is configured to allow attachment of the male part 11 to the female part 12 in accordance with a determination result of the breath component concentration determining means 300.

21 Claims, 32 Drawing Sheets

(a)

(b)

(a)

(b)

(a)

(b)

(a)

(b)

(a)

(b)

SAFE-DRIVING PROMOTION SYSTEM AND SAFE-DRIVING PROMOTION DEVICE

TECHNICAL FIELD

The present invention relates to a safe-driving promotion system and a safe-driving promotion device that promote safe driving by obliging a user of an automobile to wear a seat belt.

BACKGROUND ART

Conventional devices to promote safe driving of an automobile include a seat-belt forcibly-wearing device in which a motor of an automobile cannot be started unless a male part of a seat belt of the automobile is attached to a female part thereof (see Patent Documents 1 and 2), a number plate having a function of indicating outside an automobile if alcohol of a predetermined concentration is contained in breath of a driver (see Patent Document 3).

Patent Document 1: Japanese Patent Application Laid-Open No. 50-79022
Patent Document 2: Japanese Patent Application Laid-Open No. 06-239200
Patent Document 3: Japanese Patent No. 3514733

DISCLOSURE OF THE INVENTION

However, there has been no conventional device capable of obliging the wearing of a seat belt and effectively preventing drunk driving.

The present invention is devised in light of the above-described situations, and an object of the present invention is to provide a safe-driving promotion system and a safe-driving promotion device capable of obliging the wearing of a seat belt and effectively preventing drunk driving and/or drug driving.

Means to be Solved the Problem

In order to solve the above-described problem, the present invention provides a safe-driving promotion system employed in an automobile, which is equipped with attachment sensing means for sensing that a male part of a seat belt of an automobile has been attached to a female part of the seatbelt and outputting a first start permission signal, and start controlling means for receiving the first start permission signal and putting a motor of the automobile into a startable state, the system comprising breath component concentration determining means for detecting alcohol and/or drug contained in breath of a driver of the automobile and performing concentration determination of the alcohol and/or drug; and attachment preventing means for preventing attachment between the male part and the female part of the seat belt. The attachment preventing means is configured to allow attachment of the male part of the seat belt to the female part in accordance with a determination result of the breath component concentration determining means.

In the case where the attachment preventing means is provided in the female part of the seat belt, the attachment preventing means may be configured to open and close an insertion slot of the female part for receiving the male part, or may be configured to be projectable and retractable within an insertion slot of the female part for receiving the male part. In the case where the attachment preventing means is provided in the male part of the seat belt, the attachment preventing means may be projectable and retractable along an insertion part of the male part, the insertion part insertable into an insertion slot of the female part, or the attachment preventing means may be configured such that an insertion part of the male part of the seat belt can move into and out of a male part main body.

It is preferable that the safe-driving promotion system has biometric means for reading physical characteristics of the driver to authenticate the driver. In this case, the breath component concentration determining means can detect the alcohol and/or drug in the breath of the driver only when the biometric means determines that the driver is authentic.

It is preferable that the breath component concentration determining means can detect the alcohol and/or drug in the breath of the driver only within a predetermined period of time after the biometric means determines that the driver is authentic.

It is preferable that the breath component concentration determining means is separately provided from the attachment preventing means and the attachment sensing means. In the case where the biometric means is included, the breath component concentration determining means is separately provided together with the biometric means.

A global positioning system (GPS) transmitter may be provided in the male part or the female part of the seat belt. This GPS transmitter can be separately provided together with the breath component concentration determining means.

The breath component concentration determining means, the biometric means and/or the GPS transmitter can be incorporated in a mobile telephone.

The system may further include recording means for recording that the first start permission signal of the attachment sensing means is received. It is preferable to simultaneously record a reception time of the first start permission signal on the recording means. Since such recording data serve as operation data of the driver's automobile, it can be used for operation management and the like.

The start controlling means has means for directly putting the motor of the automobile into the startable state or means for indirectly putting the same into the startable state. As means for directly putting the motor into the startable state, a body controller of an automobile for controlling the start of the motor of the automobile may be used. This body controller puts the motor into the startable state only when receiving the first start permission signal. In the case where the system includes signal output means for outputting a second start permission signal to put the motor of the automobile into the startable state, the body controller preferably puts the motor of the automobile into the startable state only when receiving both of the first and second start permission signals.

As first means for indirectly putting the motor into the startable state, the system may use first blocking means that is adapted to open and close at least part of a keyhole of the automobile. This first blocking means may be configured to open the keyhole upon receiving the first start permission signal of the attachment sensing means.

As second means for indirectly putting the motor into the startable state, the system may use means that is projectable and retractable in a keyhole of the automobile, and is configured to be retracted from a projected position with respect to the keyhole in response to the first start permission signal of the attachment sensing means.

As third means for indirectly putting the motor into the startable state, the system may use second blocking means for openably blocking a receiving unit of a receiving means. The receiving means is provided for receiving second start permission signal for putting the motor of the automobile into the startable state, which is outputted from the signal output means. This second blocking means may open the receiving means in accordance with the first start permission signal of the attachment sensing means.

As a fourth means for indirectly putting the motor into the startable state, the system may use operation preventing means for preventing operation of a start operating unit operated to start the motor of the automobile. This operation preventing means puts the start operating unit into an operable state in accordance with the first start permission signal of the attachment sensing means.

More specifically, the operation preventing means may be third blocking means for openably blocking an operating surface of the start operating unit, and open the start operating unit upon receiving the first start permission signal of the attachment sensing means. In the case where the start operating unit is a push switch, the operation preventing means may be engagement means for engagement with the start operating unit or a housing of an automobile where the start operating unit is provided, to prevent the pushing operation of the start operating unit. Further, upon receiving the first start permission signal of the attachment sensing means, the operation preventing means may be brought out of engagement with the start operating unit or the housing of the automobile where the start operating unit is provided.

A safe-driving promotion device of the present invention includes breath component concentration determining means for detecting alcohol and/or drug contained in breath of a driver of an automobile and performing concentration determination of the alcohol and/or drug; and attachment preventing means for preventing attachment between a male part and a female part of a seat belt. The attachment preventing means is configured to allow attachment of the male part of the seat belt to the female part in accordance with a determination result of the breath component concentration determining means.

EFFECTS OF THE INVENTION

In the case of the safe-driving promotion system according to claim 1 of the present invention, in starting the motor of the automobile, the driver of the automobile is subjected to the concentration determination of alcohol and/or drug in the breath of the driver using the breath component concentration determining means. As a result, if the concentration of the alcohol and/or drug is in an acceptable level that would not harm the driving of the automobile, the attachment preventing means allow the male part of the seat belt to be attached to the female part, and thus the seat belt can be attached. When the seat belt is attached, the first start permission signal is outputted from the attachment sensing means for sensing the attachment of the seat belt, and the motor of the automobile is put into the startable state by the start controlling means, so that the motor can be started. On the other hand, if the concentration of the alcohol and/or drug is in a level that would harm the driving of the automobile, the attachment preventing means keeps preventing the attachment between the male part and the female part of the seat, and thus the seat belt cannot be fastened. When the seat belt cannot be fastened, the first start permission signal is not outputted from the attachment sensing means, and thus, the start controlling means keeps inhibiting the start of the motor of the automobile. Therefore, the driver can be forced to wear the seat belt, and drunk driving and/or drug driving of the driver of the automobile can be effectively prevented.

The safe-driving promotion system according to claim 2 of the present invention can be realized with a simple configuration because the attachment preventing means is configured to open and close the insertion slot of the female part for receiving the male part. Therefore, cost reduction can be achieved. Moreover, the safe-driving promotion system according to claim 3 of the present invention can be realized with a simple configuration as in claim 2, because the attachment preventing means is projectable and retractable within an insertion slot of the female part for receiving the male part. Therefore, cost reduction can be achieved.

The safe-driving promotion system according to claim 4 of the present invention can be realized with a simple configuration, because is projectable and retractable along an insertion part of the male part. Therefore, cost reduction can be achieved. Moreover, the safe-driving promotion system according to claim 5 of the present invention can be realized with a simple configuration, because the attachment preventing means is configured such that an insertion part of the male part of the seat belt can move into and out of a male part main body. Therefore, cost reduction can be achieved.

In the case of the safe-driving promotion system according to claim 6 of the present invention, the breath component concentration determining means does not perform the detection of the alcohol and/or drug in the breath of the driver unless the biometric means determines that the driver is authentic. Therefore, the system can prevent a third person, in place of the driver, from being subjected to the concentration determination of the alcohol and/or drug using the breath component concentration determining means.

In the case of the safe-driving promotion system according to claim 7 of the present invention, the breath component concentration determining means can detect the alcohol and/or drug in the breath of the driver only within a predetermined period of time after the biometric means determines that the driver is authentic. Therefore, the system can prevent a third person, in place of the driver, from being subjected to the concentration determination of the alcohol and/or drug using the breath component concentration determining means.

In the case of the safe-driving promotion system according to claim 8 of the present invention, the breath component concentration determining means is separately provided from the attachment preventing means and the attachment sensing means. Such configuration makes the breath component concentration determining means portable, thereby improving usability.

In the case of the safe-driving promotion system according to claim 9 of the present invention, the breath component concentration determining means is provided together with the biometric means, and is separately provided from the attachment preventing means and the attachment sensing means. Such configuration makes the breath component concentration determining means and the biometric means portable, thereby improving usability.

The safe-driving promotion system according to claim 10 of the present invention is provided with a global positioning system (GPS) transmitter is provided in the male part or the female part of the seat belt. A GPS signal of the GPS transmitter is received by a management center or the like to be utilized for position search of the automobile and for operation management of the automobile. Therefore, the system can attain high general versatility.

In the case of the safe-driving promotion system according to claim 11 of the present invention, since the GPS transmitter is provided together with the separated breath component concentration determining means. The system can be used not only for the position search of the automobile but also for position search of a user. Therefore, the system can attain high general versatility.

In the case of the safe-driving promotion system according to claim 12 of the present invention, the breath component concentration determining means is incorporated in a mobile telephone together with the biometric means, or the breath component concentration determining means is incorporated in a mobile telephone together with the biometric means and the GPS transmitter. Therefore, since only carrying the mobile telephone results in carrying the breath component concentration determining means and the like, the usability and convenience are improved.

In the case of the safe-driving promotion system according to claim 13 of the present invention, the start controlling means is a body controller of the automobile that controls the start of the motor of the automobile. Thus, since the system can utilize the body controller of the automobile, the automobile does not need extensive modifications in design. Therefore, cost reduction can be achieved.

In the case of the safe-driving promotion system according to claim 14 of the present invention, the start controlling means puts the motor of the automobile into the startable state only when receiving both of the first start permission signal of the attachment sensing means and the second start permission signal of the signal output means such as an immobilizer. That is, since the motor can be started only when the start controlling means receives the first and second start permission signals, there is a merit in preventing automobile theft.

In the case of the safe-driving promotion system according to claim 15 of the present invention, the start controlling means is the first blocking means that opens and closes at least part of the keyhole of the automobile, and opens the keyhole upon receiving the first start permission signal of the attachment sensing means. Thus, just adopting the keyhole to open and close partly, the system can be realized with a simple configuration without extensively modifying the automobile in design. Therefore, cost reduction can be achieved.

In the case of the safe-driving promotion system according to claim 16 of the present invention, the start controlling means is projectable and retractable within a keyhole of the automobile, and is configured to be retracted from a projected position with respect to the keyhole in response to the first start permission signal of the attachment sensing means. Thus, just providing means that is projectable and retractable within a keyhole of the automobile, the system can be realized with a simple configuration without extensively modifying the automobile in design. Therefore, cost reduction can be achieved.

In the case of the safe-driving promotion system according to claim 17 of the present invention, the start controlling means is the second blocking means for openably blocking a receiving unit of the receiving means, and releases the receiving means in accordance with the first start permission signal of the attachment sensing means. Thus, since the start controlling means only needs to openably block the receiving means for receiving the second start permission signal, the system can be realized with a simple configuration without extensively modifying the automobile in design. Therefore, cost reduction can be achieved.

In the case of the safe-driving promotion system according to claim 18 of the present invention, the start controlling means is the operation preventing means for preventing the operation of a start operating unit operated to start the motor of the automobile, and puts the start operating unit into an operable state in accordance with the first start permission signal of the attachment sensing means. Therefore, the system can be realized without extensively modifying the automobile in design, and cost reduction can be achieved.

In the case of the safe-driving promotion system according to claim 19 of the present invention, the start controlling means is the third blocking means for openably blocking the operating surface of the start operating unit, and opens the start operating unit upon receiving the first start permission signal of the attachment sensing means. Thus, since the start controlling means only needs to openably block the operating surface of the start operating unit, the system can be realized with a simple configuration, which can bring about lower cost.

In the case of the safe-driving promotion system according to claim 20 of the present invention, the start controlling means is engagement means for engagement with the start operating unit or a housing of an automobile where the start operating unit is provided, to prevent the pushing operation of the start operating unit. Further, upon receiving the first start permission signal of the attachment sensing means, the start controlling means brings the engagement means out of engagement with the start operating unit or the housing of the automobile where the start operating unit is provided. Thus, since the start controlling means only engages with the start operating unit or the housing part of the automobile, the system can be realized with a simple configuration. Therefore, cost reduction can be achieved.

In the case of the safe-driving promotion device according to claim 21 of the present invention, in starting the motor of the automobile, the driver of the automobile is subjected to the concentration determination of alcohol and/or drug in the breath of the driver using the breath component concentration determining means. As a result, if the concentration of the alcohol and/or drug is in an acceptable level that would not harm the driving of the automobile, the attachment preventing means allow the male part of the seat belt to be attached to the female part, and thus the seat belt can be attached. On the other hand, if the concentration of the alcohol and/or drug is in a level that would harm the driving of the automobile, the attachment preventing means keeps preventing the attachment between the male part and the female part of the seat belt, and thus the seat belt cannot be attached. In some of recent automobiles has a warning device that continues to sound when the seat belt cannot be fastened. Moreover, the police crack down on drivers with unfastened seatbelt. Accordingly, the claimed device can promote the wearing of the seat belt and can effectively prevent the driver of the automobile from drunk driving and/or drug driving.

BEST MODE FOR CARRYING OUT THE INVENTION

Hereinafter, the embodiments of the present invention will be described.

EMBODIMENT 1

Figure 1:
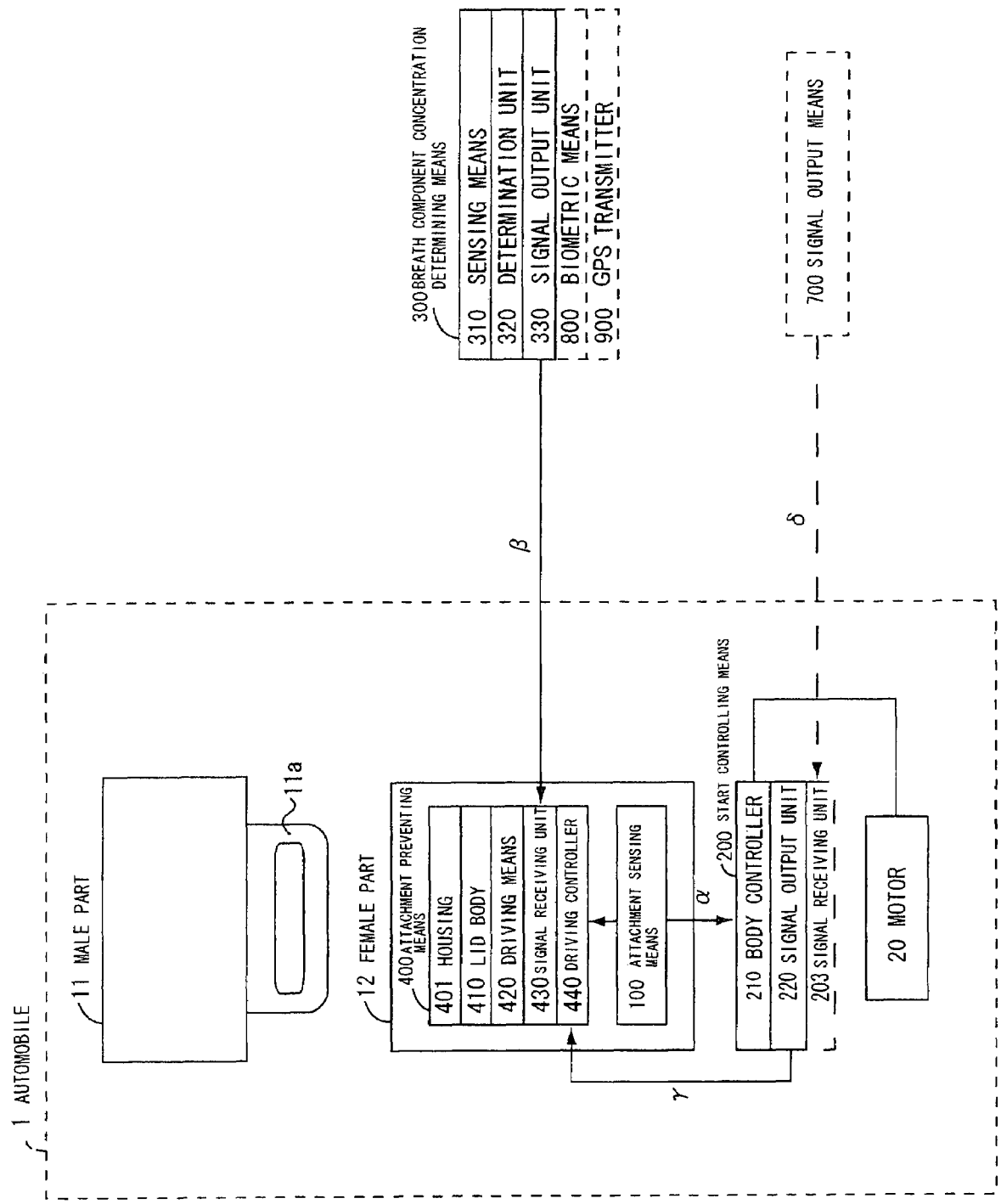
FIG. 1 is a block diagram of a safe-driving promotion system according to a first embodiment of the present invention.
Figure 2:
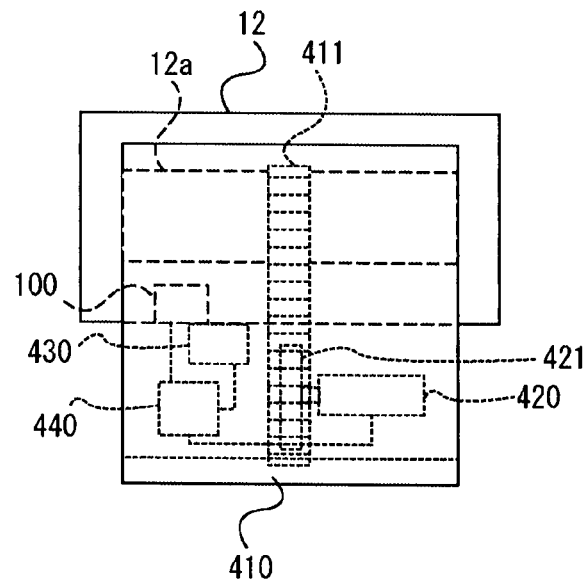
FIG. 2 is schematic plane views showing a female part of a seat belt of the same system, (a) being a view showing a state where an insertion slot is shut by attachment preventing means, (b) being a view showing a state where the insertion slot is opened by the attachment preventing means.
Figure 2:
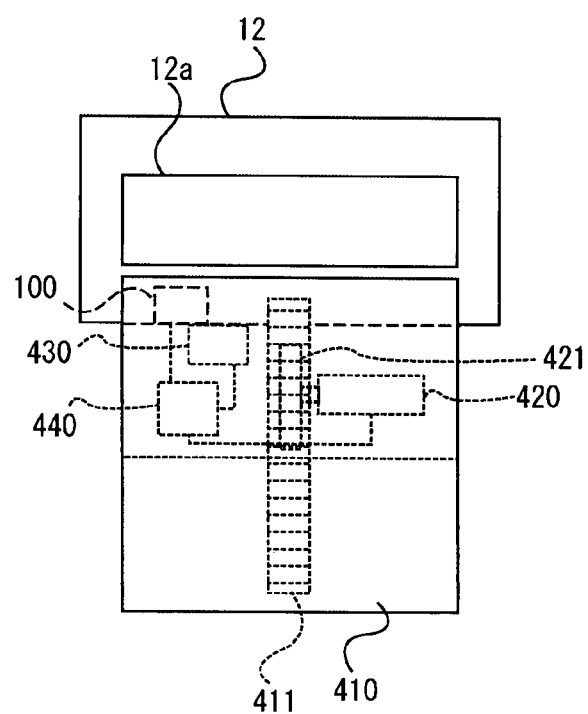
Figure 3:
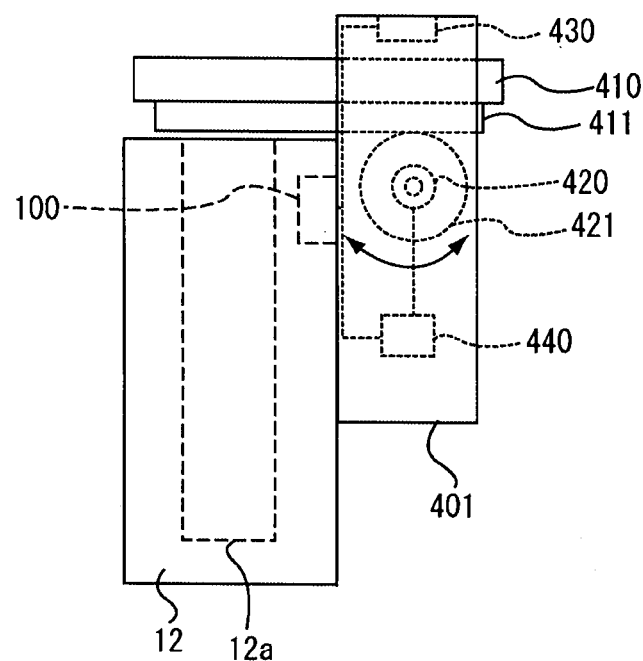
FIG. 3 is schematic side views showing the female part of the seat belt of the same system, in which an inside can be seen transparently, (a) being a view showing the state where the insertion slot is shut by the attachment preventing means, (b)) being a view showing the state where the insertion slot is opened by the attachment preventing means.
Figure 3:
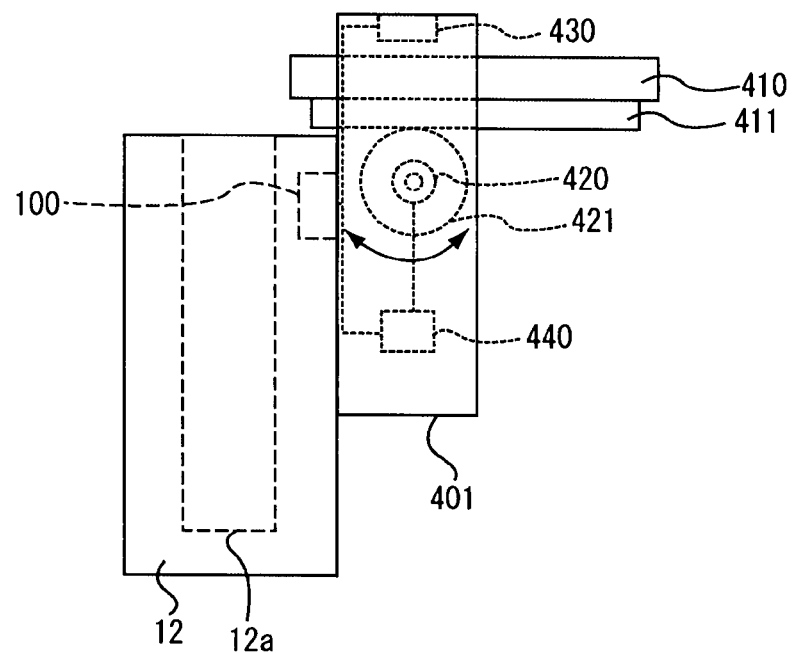
Figure 4:
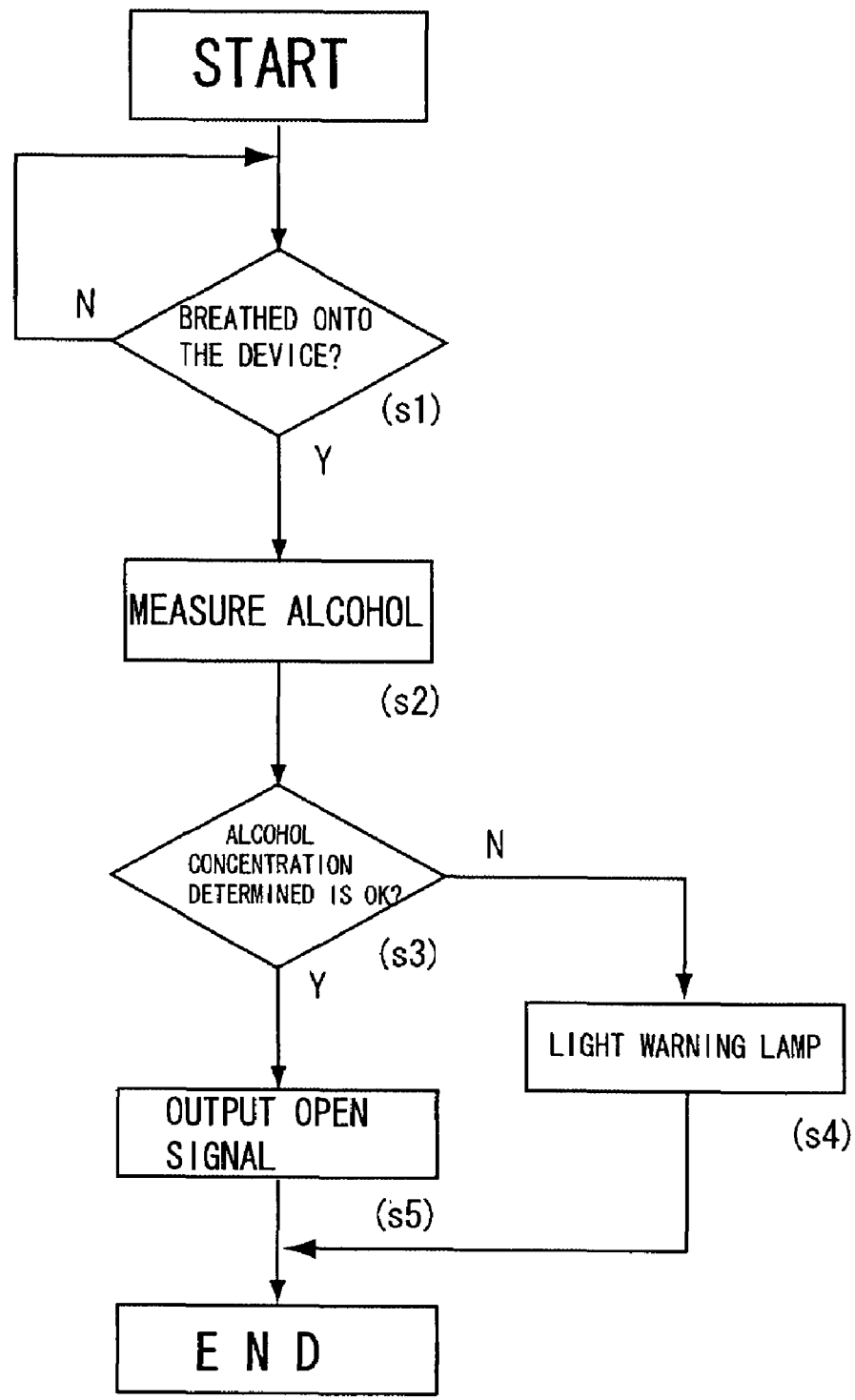
FIG. 4 is a flowchart of a first alcohol concentration determining program processed by a determination unit of breath component concentration determining means of the same system.
Figure 5:
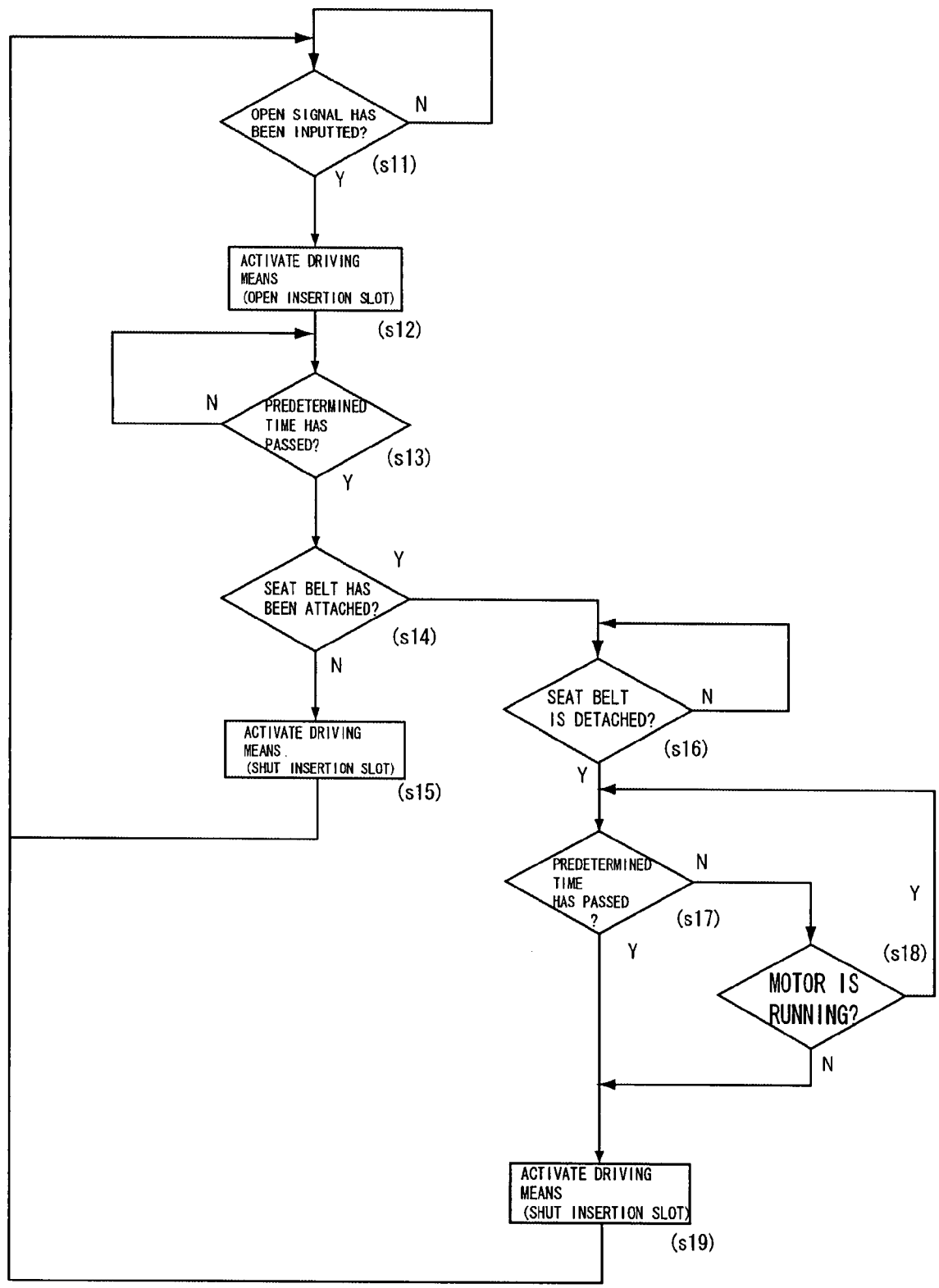
FIG. 5 is a flowchart of a motor driving control program processed by a driving controller of the attachment preventing means of the same system.

Referring to the drawings, a safe-driving promotion system according to a first embodiment of the present invention is described. FIG. 1 is a block diagram of the safe-driving promotion system according to the first embodiment of the present invention. FIG. 2 is schematic plane views showing a female part of a seat belt of the same system, (a) being a view showing a state where an insertion slot is shut by attachment preventing means, (b) being a view showing a state where the insertion slot is opened by the attachment preventing means. FIG. 3 is schematic side views showing the female part of the seat belt of the same system, in which an inside can be seen transparently, (a) being a view showing the state where the insertion slot is shut by the attachment preventing means, (b) being a view showing the state where the insertion slot is opened by the attachment preventing means. FIG. 4 is a flowchart of a first alcohol concentration determining program processed by a determination unit of breath component concentration determining means of the same system. FIG. 5 is a flowchart of a motor driving control program processed by a driving controller of the attachment preventing means of the same system.

The safe-driving promotion system shown in FIG. 1 includes attachment sensing means 100 for sensing that a male part 11 of a seat belt of an automobile 1 has been attached to a female part 12 and outputting a first start permission signal α, start controlling means 200 for receiving this first start permission signal α and bringing a motor 20 of the automobile 1 into a startable state, breath component concentration determining means 300 for detecting alcohol contained in breath of a driver of the automobile 1 and determining the alcohol concentration, and attachment preventing means 400 for preventing the attachment between the male part 11 and the female part 12 of the seat belt. Hereinafter, the respective units and parts are described in detail.

The male part 11 of the seat belt has a tongue 11a (insertion part) adapted to be attachable to the female part 12, as shown in FIG. 1. On the other hand, as shown in FIGS. 2 and 3, the female part 12 of the seat belt is provided with an insertion slot 12a for receiving the tongue 11a, and a locking mechanism (not shown) for locking the tongue 11a inserted into this insertion slot 12a.

The breath component concentration determining means 300 is incorporated in a mobile device (i.e., separated body) or a mobile telephone carried by the driver. The determining means 300 has sensing means 310 for sensing alcohol contained in the breath of the driver, a determination unit 320 for determining the alcohol concentration in accordance with a detection result of this sensing means 310, and a signal output unit 330 for outputting an open signal β to the attachment preventing means 400 in accordance with a determination result of the determination unit 320.

The sensing means 310 is equipped with a well-known semiconductor sensor. When a user breathes on the sensor for a predetermined time (for about 2 seconds), the internal resistance of the sensor changes and this change of the internal resistance is outputted as an output signal. In the sensing means 310, if alcohol is contained in the breath, the alcohol adheres to a catalyst within the sensor, and the internal resistance significantly changes. The alcohol adhering to the catalyst burns and evaporates by heating-up the sensor.

The determination unit 320 uses a microcomputer or the like. It has an input port to connect the sensing means 310, and also has an output port to connect the signal output unit 330. On a memory (not shown) of the determination unit 320, there are recorded a first alcohol concentration determining program as shown in FIG. 4 and a reference value of alcohol by which it is determined that the driver is under the influence of drinking. That is, by processing the first alcohol concentration determining program, the determination unit 320 measures the alcohol concentration in the breath of the driver based on sensing data of the sensing means 310, and compares a value of this measurement result with the reference value on the memory to determine whether or not the measured value is above the reference value. If the determination unit 320 determines that the measured value (i.e., the value of the alcohol concentration in the breath of the driver) is less than the reference value, then the determination unit 320 allows the signal output unit 330 to output the open signal β, while the determination unit 320 determines that the value is the reference value or above, a warning lamp not shown is switched on.

The breath component concentration determining means 300 may also be equipped with biometric means 800 for reading physical characteristics of the driver to authenticate the driver and/or a global positioning system (GPS) transmitter 900.

In the case where the biometric means 800 is equipped, the determination unit 320 also functions as an authentication determining unit of the biometric means 800. More specifically, personally-identifying information of the driver(s) is recorded on the memory of the determination unit 320 in advance. As the determination unit 320 compares personally-identifying data read by the biometric means 800 and the personally-identifying information on the memory, the alcohol in the breath of the driver can be detected only when it is determined that the driver is authentic. More preferably, the detection of the alcohol in the breath of the driver is allowed only within a predetermined period of time after the determination that the driver is authentic. This can prevent a person other than the driver from being subjected to the alcohol concentration determination in place of the driver.

In the case where the GPS transmitter 900 is equipped, the reception of a GPS signal enables position search of a driver holding the breath component concentration determining means 300 and operation management of the automobile 1.

The attachment sensing means 100 is provided in the female part 12 of the seat belt and includes a position detecting switch such as a limit switch, a photosensor and the like. The attachment sensing means 100 senses a position of the tongue 11a of the inserted male part 11, and outputs an output signal thereof as the first start permission signal α to the start controlling means 200, while outputting the same output signal to a driving controller 440 of the attachment preventing means 400.

The attachment preventing means 400 is provided in the female part 12 of the seat belt, and is configured to open and close the insertion slot 12a of the female part 12 for receiving the tongue 11a of the male part 1. More specifically, as shown in FIGS. 2 and 3, the attachment preventing means 400 has a housing 401 provided integrally with the female part 12 of the seat belt, a lid body 410 that is provided in such a manner as to move into and out of the housing 401 and is intended to shut the insertion slot 12a of the female part 12, driving means 420 that moves this lid body 410 from a shutting position where the insertion slot 12a of the female part 12 is shut (FIGS. 2(a) and 3(a)) to an opening position where the insertion slot 12a is opened (FIGS. 2(b) and 3(b)), a signal receiving unit 430 that receives the open signal β of the signal output unit 330 of the breath component concentration determining means 300, and a driving controller 440 that controls the driving of the driving means 420.

The lid body 410 is a resin-molded component, and is provided with a rack gear 411 extending in a moving direction on one surface. The driving means 420 includes a motor and its top is provided with a pinion 421 for engagement with the rack gear 411 of the lid body 410. That is, rotational motion of the driving means 420 is converted to linear motion of the lid body 410.

The driving controller 440 uses a microcomputer or the like. It has an input port to connect the signal receiving unit 430, the attachment sensing means 100, and a signal output unit 220 of the start controlling means 200, and also has an output port to connect the driving means 420. A motor driving control program shown in FIG. 5 is recoded on a memory of the driving controller 440. That is, by processing the motor driving control program, the driving controller 440 rotationally drives the driving means 420 in accordance with the open signal β inputted through the signal receiving unit 430 to move the lid body 410 from the shutting position to the opening position. Moreover, the driving controller 440 determines whether or not the male part 11 of the seat belt has been attached to the female part 12 based on the output signal of the attachment sensing means 100. If it is determined that the male part 11 has not been attached, the driving controller 440 rotationally drives the driving means 420 to move the lid body 410 from the opening position to the shutting position. Furthermore, when a motor state signal γ of the signal output unit 220 of the start controlling means 200 is inputted, the driving controller 440 sets a predetermined flag on the memory, and when the motor state signal γ is inputted again, the predetermined flag on the memory is reset.

The start controlling means 200, equipped in the automobile 1, has an automobile body controller 210 to control the entire automobile 1 such as controlling the start of the motor 20, and the signal output unit 220 to output the motor state signal γ to the driving controller 440. The body controller 210 puts the motor 20 into a startable state only when the first start permission signal α is received. The specific means to take for putting the motor 20 into the startable state include the following means (1) to (4) but other means may be taken to put the motor 20 into the startable state.

(1) To switch a switching circuit provided in a power circuit (not shown) of the motor 20 and supply power to the motor 20 only when receiving the first start permission signal α.

(2) To control ON/OFF of a starter motor (not shown) of the motor 20 or a start circuit (not shown) and put the starter motor or the start circuit into an ON state only when receiving the first start permission signal α.

(3) In the case where the automobile 1 is equipped with a start operating unit (not shown) for starting the motor 20: to control ON/OFF of the start operating unit and put the start operating unit into an ON state only when receiving the first start permission signal α.

(4) In the case where the automobile 1 is equipped with a signal receiving unit 203 that receives a second start permission signal δ for starting the motor 20 of signal output means 700, such as an immobilizer: to control ON/OFF of the signal receiving unit 203 and bring the signal receiving unit into an ON state only when receiving the first start permission signal α. In the case where the motor 20 is enabled to be started upon receiving the second start permission signal δ of the signal output means 700 such as the immobilizer in addition to one of the means (1) to (3), it is preferable that the motor 20 is put into the startable state only when both of the first start permission signal α and the second start permission signal δ are inputted.

Moreover, every time the motor 20 starts or stops, the body controller 210 processes a signal output interrupting program (not shown) to make the signal output unit 220 output the motor state signal γ.

Hereinafter, the usage of the safe-driving promotion system of the above-described configuration is described. Detailed descriptions will also be made on the first alcohol concentration determining program shown in FIG. 4 which is processed by the determination unit 320 of the breath component concentration determining means 300, and the motor driving control program shown in FIG. 5 which is processed by the driving controller 440 of the attachment preventing means. Further, the operations of the respective units and parts are also described.

First, before the motor 20 of the automobile 1 is started, the safe-driving promotion system is in a state as shown in FIGS. 2(*a*) and 3(*a*). Particularly, the lid body 410 of the attachment preventing means 400 is located in the shutting position shutting the insertion slot 12*a* of the female part 12 of the seat belt. Thereafter, in starting the motor 20 of the automobile 1, the driver turns on the breath component concentration determining means 300. In response to this, the determination unit 320 of the breath component concentration determining means 300 processes the first alcohol concentration determining program as shown in FIG. 4. Then, the determination unit 320 determines whether or not sensing data of the sensing means 310 has been inputted (i.e., whether or not the sensing means 310 has been breathed on) (s1). As a result, if it is determined that the breathing has not been performed, the processing returns to Step 1. If it is determined that the sensing data has been inputted and that the breathing has been performed, the alcohol concentration contained in the breath of the driver is measured based on the sensing data of the sensing means 310 (s2). It is then determined whether or not a value of the measurement result (i.e., a value of the alcohol concentration in the breath of the driver) is the reference value on the memory or above (s3). As a result, if it is determined that the value is the reference value or above, the warning lamp is lighted (s4), and the processing of the first alcohol concentration determining program is finished. On the other hand, if it is determined that the value of the measurement result is less than the reference value, the determination unit 320 allows the signal output unit 330 of the breath component concentration determining means 300 to output the open signal β (s5), and finishes the processing of the first alcohol concentration determining program.

The driving controller 440 of the attachment preventing means 400 constantly processes the motor driving control program shown in FIG. 5, and determines whether or not the open signal β has been inputted through the signal receiving unit 430 of the attachment preventing means 400 (s11) As a result, if it is determined that the open signal β has been inputted, the driving controller 440 activates a timer circuit, and rotationally drives the driving means 420 (s12) to move the lid body 410 from the shutting position to the opening position. Since the insertion slot 12*a* of the female part 12 is thereby opened to allow the attachment of the male part 11 to the female part 12. Once the male part 11 is attached to the female part 12, the first start permission signal α is outputted from the attachment sensing means 100. When receiving the first start-permission signal α, the start controlling means 200 puts the motor 20 into the startable state. This allows the driver to start the motor 20.

After step 12, the driving controller 440 determines in reference to a counting value of the timer circuit whether or not a predetermined time has passed after the insertion slot 12*a* of the female part 12 was opened (s13). As a result, if it is determined that the predetermined time has not passed, the processing of step 13 is repeated. On the other hand, if it is determined that the predetermined time has passed, then the driving controller 440 determines whether or not the male part 11 has been attached to the female part 12 based on the output signal of the attachment sensing means 100 (s14). As a result, if it is determined that the male part 11 has not been attached to the female part 12, the driving means 420 is rotationally driven (s15) to move the lid body 410 from the opening position to the shutting position. The lid body 410 thereby shuts the insertion slot 12*a* of the female part 12. Then, the processing returns to step 11.

If it is determined in step 14 that the male part 11 has been attached to the female part 12, then the driving controller 440 determines whether or not the male part 11 has been detached from the female part 12 based on the output signal of the attachment sensing means 100 (s16). That is, it is determined whether or not the seat belt has been detached after finishing driving. As a result, if it is determined that the seat belt has not been detached, the processing of step 16 is repeated. If it is determined that the seat belt has been detached, the driving controller 440 activates the timer circuit and determines in reference to the counting value of the timer circuit whether or not a predetermined time (e.g., about 10 minutes) has passed after the male part 11 was detached from the female part 12 (s17). As a result, if it is determined that the predetermined time has not passed, then the driving controller 440 determines whether or not the motor 20 has stopped (i.e., whether the predetermined flag on the memory of the driving controller 440 has been set) (s18). That is, whether or not the driving is actually finished is determined. As a result, if it is determined that the motor 20 has not stopped, the processing returns to step 17. That is, as the driving is considered as not having been actually finished, the insertion slot 12*a* of the female part 12 is kept in an opened state. This allows the driver to restart the driving without being subjected to the alcohol concentration determination using the breath component concentration determining means 300 until the predetermined time of step 17 has passed.

If it is determined that the predetermined time has passed in step 17, or if it is determined that the motor 20 has stopped in step 18, the driving means 420 is rotationally driven (s19) to move the lid body 410 from the opening position to the shutting position. The lid body 410 there by shuts the insertion slot 12*a* of the female part 12. Then, the processing returns to step 11.

In the above-described safe-driving promotion system, if the determination unit 320 of the breath component concentration determining means 300 determines that alcohol of the reference value or above is contained in the breath of the driver, then the open signal β is not outputted from the signal output unit 330 of the breath component concentration determining means 300. The lid body 410 of the attachment preventing means 400, therefore, is located in the shutting position to maintain the state where the insertion slot 12*a* of the female part 12 of the seat belt is shut, which disables the female part 12 of the seat belt to receive the male part 11. Thus, when the seat belt cannot be attached, the first start permission signal α is not outputted from the attachment sensing means 100 provided in the female part 12, and the start controlling means 200 does not bring the motor 20 of the automobile 1 into the startable state, so that the driver cannot start the motor 20. Thus, the drunk driving of the driver can be effectively prevented.

On the other hand, if the determination unit 320 of the breath component concentration determining means 300 determines that the alcohol of the reference value or above is not contained in the breath of the driver, the open signal β is outputted from the signal output unit 330 of the breath component concentration determining means 300. In response to the signal, the lid body 410 of the attachment preventing means 400 moves from the shutting position to the opening position to open the insertion slot 12*a* of the female part 12. This enables the female part 12 to receive the male part 11. Then, if the male part 11 of the seat belt is not attached to the female part 12, the first start permission signal α is not outputted from the attachment sensing means 100 provided in the female part 12. Since the safe-driving promotion system has such a configuration that if the first start permission signal α is not inputted, the body controller 210 of the start controlling means 200 does not bring the motor 20 of the automobile 1 into the startable state. Consequently, the safe-driving promotion system can force the driver to wear the seat belt.

EMBODIMENT 2

Figure 6:
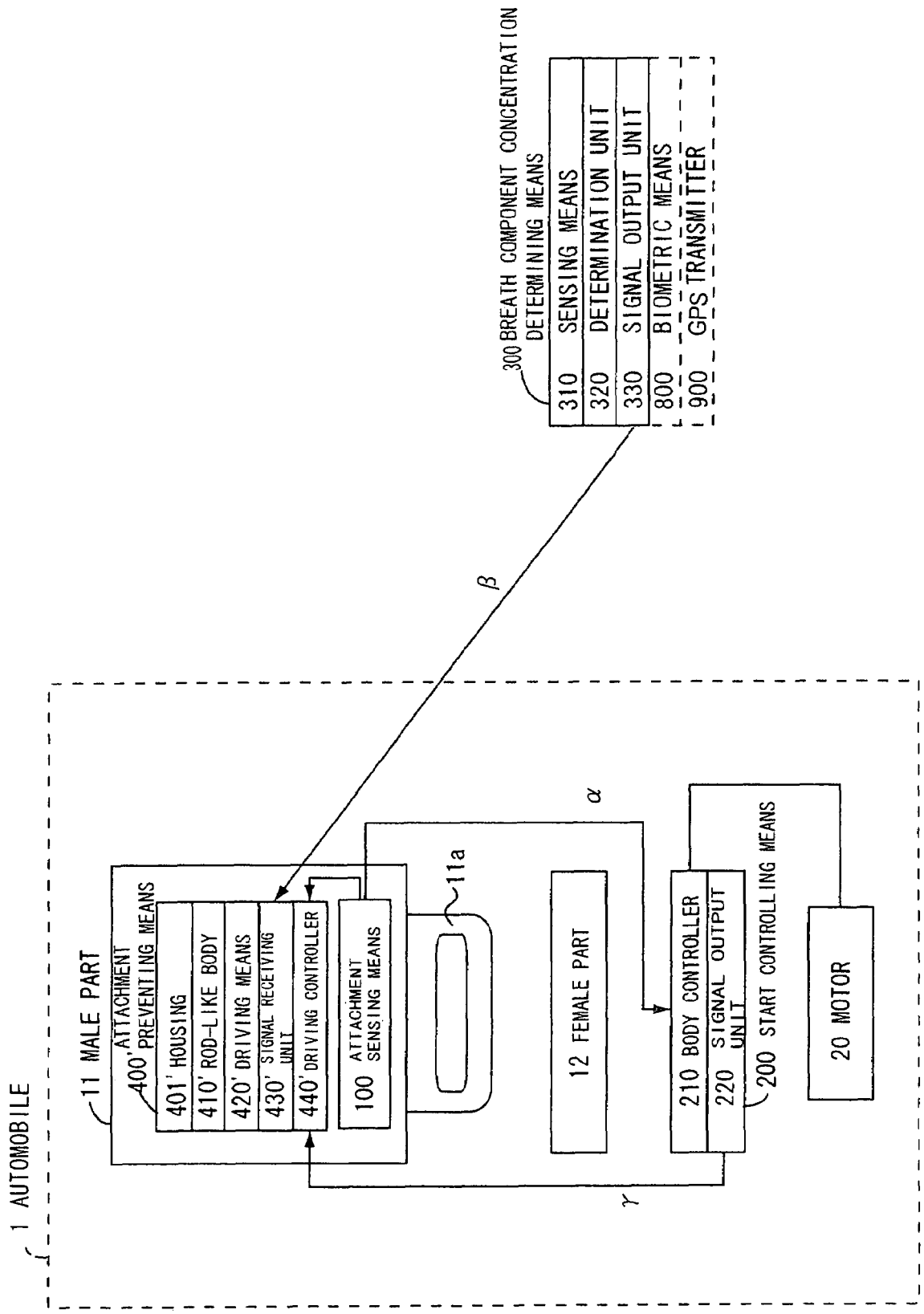
FIG. 6 is a block diagram of a safe-driving promotion system according to a second embodiment of the present invention.
Figure 7:
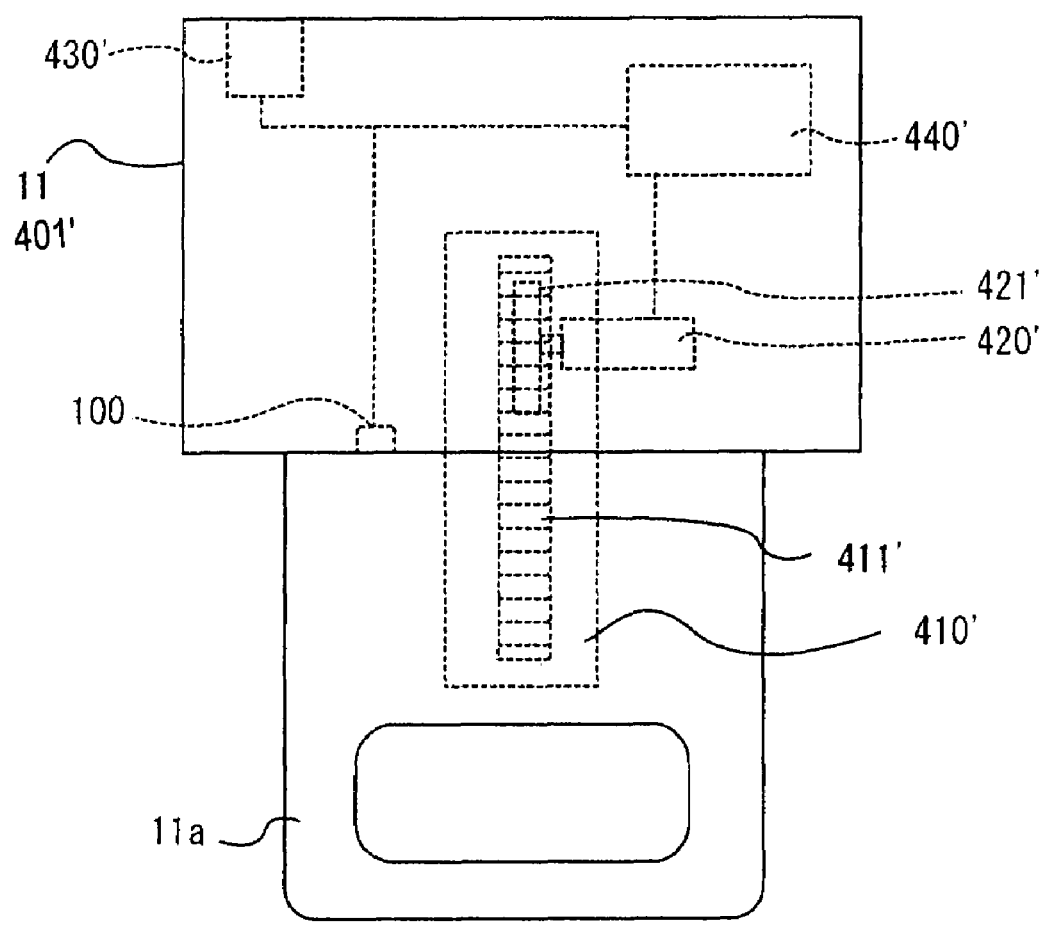
FIG. 7 is a schematic front view of a male part of a seat belt of the same system, in which an inside can be seen transparently.
Figure 8:
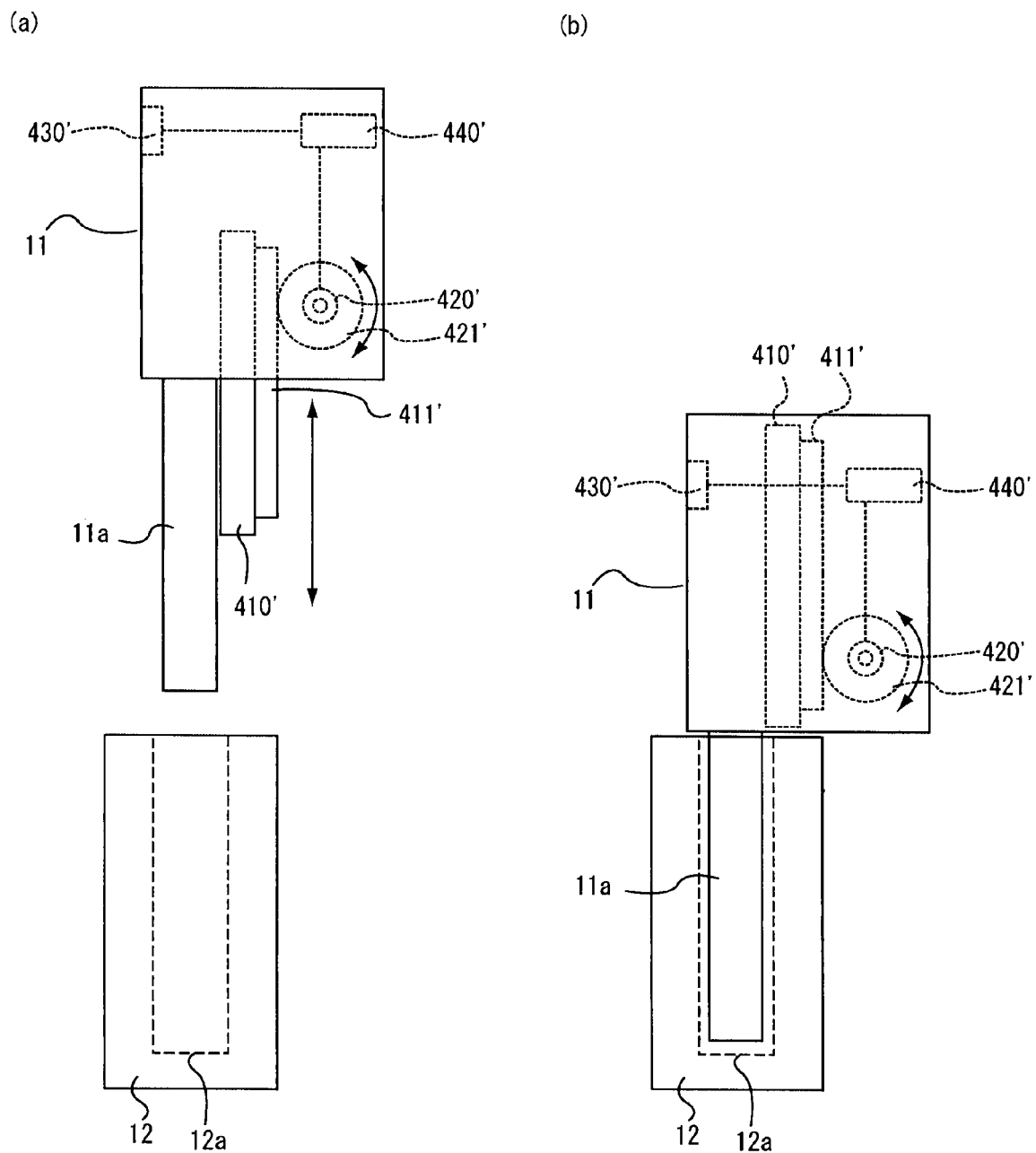
FIG. 8 is side views showing the male part and a female part of the seat belt of the same system, in which an inside can be seen transparently, (a)) being a view showing a state before attachment, (b) being a view showing an attached state.
Figure 9:
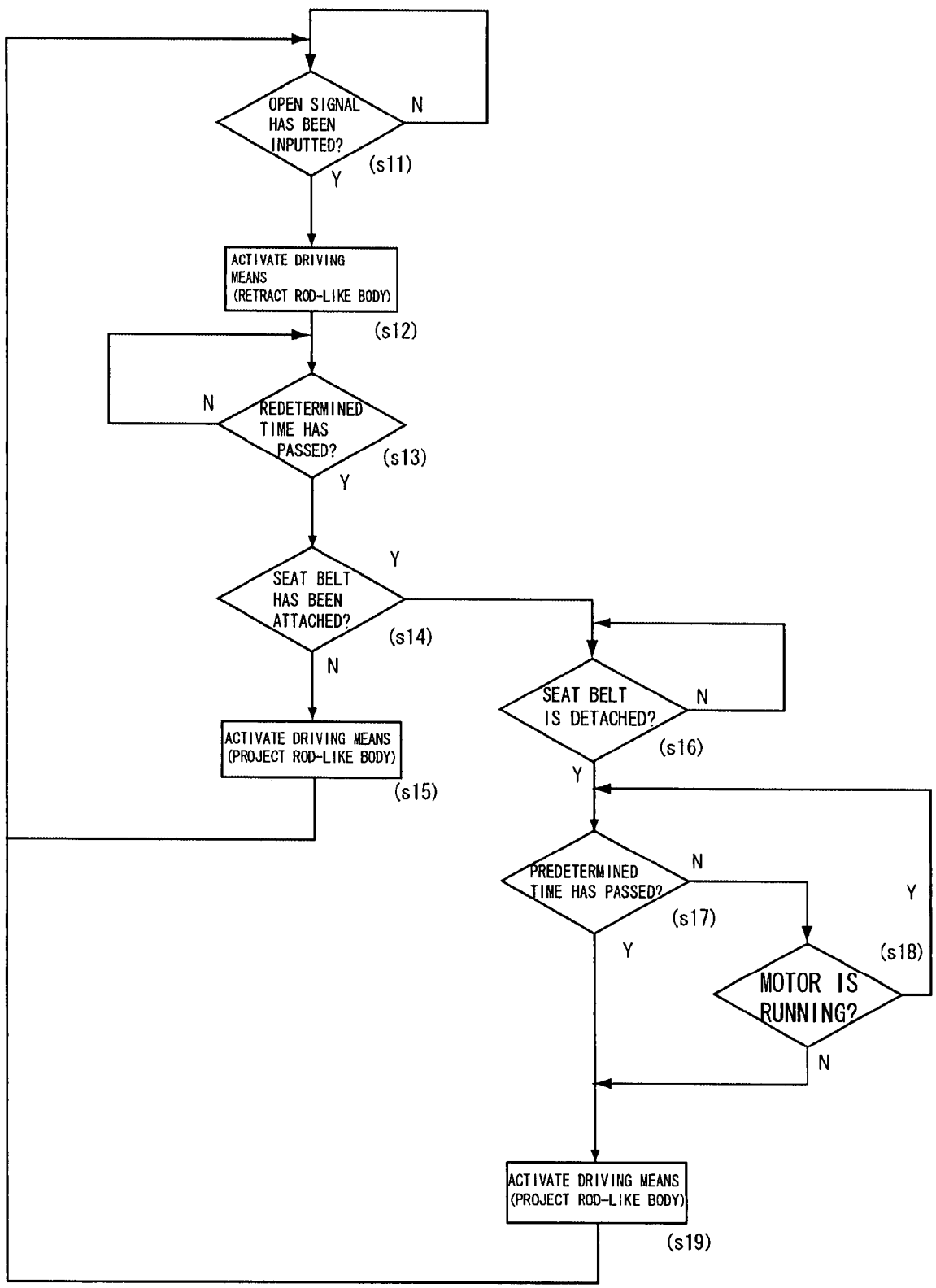
FIG. 9 is a flowchart of a motor driving control program processed by a driving controller of attachment preventing means of the same system.

Next, referring to the drawings, a safe-driving promotion system according to a second embodiment of the present invention is described. FIG. 6 is a block diagram of the safe-driving promotion system according to the second embodiment of the present invention. FIG. 7 is a schematic front view of a male part of a seat belt of the same system, in which an inside can be seen transparently. FIG. 8 is schematic side views showing the male part and a female part of the seat belt of the same system, in which an inside can be seen transparently, (a) being a view showing a state before attachment, (b) being a view showing an attached state. FIG. 9 is a flowchart of a motor driving control program processed by a driving controller of attachment preventing means of the same system.

The safe-driving promotion system shown in FIG. 6 is different from the safe-driving promotion system of Embodiment 1 in that the attachment sensing means 100 and attachment preventing means 400' are provided in the male part 11 of the seat belt. Hereinafter, the differences are described in detail, and descriptions of the overlapping are omitted. Since the attachment sensing means has the same configuration as that of Embodiment 1, the same reference numerals as those of Embodiment 1 are used. On the other hand, the reference numerals related to the attachment preventing means are apostrophized since it has a different configuration from that of Embodiment 1.

As shown in FIG. 7, the attachment sensing means 100 is a position detecting switch of the same type as in Embodiment 1. The attachment sensing means 100 senses the position of the female part 12 when the male part 11 is attached to the female part 12 and outputs the output signal to the start controlling means 200 as the first start permission signal α, while outputting the same output signal to a driving controller 440' of the attachment preventing means 400'.

The attachment preventing means 400' is configured to project and retract along the tongue 11*a* of the male part 11. More specifically, as shown in FIGS. 7 and 8, the attachment preventing means 400' has a housing 401' provided integrally with the male part 11 of the seat belt, a rod-like body 410' provided in such a manner as to move into and out of this housing 401' along the tongue 11*a*, driving means 420' for moving this rod-like body 410' from a projected position where the rod-like body 410' is projected along the tongue 11*a* (FIG. 8(*a*)) to a contained position where it is contained in the housing 401' (FIG. 8(*b*)), a signal receiving unit 430' that receives the open signal β of the signal output unit 330 of the breath component concentration determining means 300, and the driving controller 440' that controls the driving of the driving means 420'.

The rod-like body 410' is a rectangular resin-molded component, and is provided with a rack gear 411' extending in a moving direction on one surface. The driving means 420' is a motor, the head of which is provided with a pinion 421' for engagement with the rack gear 411' of the rod-like body 410'. That is, rotational motion of the driving means 420' is converted to linear motion of the rod-like body 410'.

The driving controller 440' uses a microcomputer or the like. It has an input port to connect the signal receiving unit 430', the attachment sensing means 100, and a signal output unit 220 of the start controlling means 200, and also has an output port to connect the driving means 420'. The motor driving control program shown in FIG. 9 is recorded on a memory of the driving controller 440'. That is, by processing the above-mentioned motor driving control program, the driving controller 440' rotationally drives the driving means 420' in accordance with the open signal β inputted through the signal receiving unit 430' to move the rod-like body 410' from the projected position to the contained position. Moreover, the driving controller 440' determines whether or not the male part 11 of the seat belt has been attached to the female part 12 based on the output signal of the attachment sensing means 100. If it is determined that the male part 11 has not been attached, the driving controller 440 rotationally drives the driving means 420' to move the rod-like body 410' from the contained position to the projected position. Furthermore, when the motor state signal γ of the signal output unit 220 of the start controlling means 200 is inputted, the driving controller 440' sets a predetermined flag on the memory, and when the motor state signal γ is inputted again, the predetermined flag on the memory is reset.

Hereinafter, the method of using the safe-driving promotion system of the above-described configuration is described. Detailed descriptions will also be made on the motor driving control program shown in FIG. 9 which is processed by the driving controller 440' of the attachment preventing means 400'. Further, the operations of the respective units and parts are also described.

First, before the motor 20 of the automobile 1 is started, the safe-driving promotion system is in a state as shown in FIG. 8(a). Particularly, the rod-like body 410' of the attachment preventing means 400' is located in the projected position projecting along the tongue 11a. As in Embodiment 1, in starting the motor 20 of the automobile 1, the driver is subjected to the concentration determination of the alcohol contained in his or her own breath using the breath component concentration determining means 300.

The driving controller 440' of the attachment preventing means 400' constantly processes the motor driving control program shown in FIG. 9 and determines whether or not the open signal β has been inputted through the signal receiving unit 430' of the attachment prevention means 400 (s11). As a result, if it is determined that the open signal β has been inputted, the driving controller 440' activates a timer circuit and rotationally drives the driving means 420' (s12) to move the rod-like body 410' from the projected position to the contained position (see FIG. 8(b)). Since the rod-like body 410' is moved to be contained in the housing 401', the male part 11 can be attached to the female part 12. Once the male part 11 is attached to the female part 12, the first start permission signal α is outputted from the attachment sensing means 100. When receiving this first start permission signal α, the start controlling means 200 puts the motor 20 into the startable state. This allows the driver to start the motor 20.

After step 12, the driving controller 440' determines in reference to a counting value of the timer circuit whether or not a predetermined time has passed after the rod-like body 410' was contained (s13). As a result, if it is determined that the predetermined time has not passed, the processing of step 13 is repeated. On the other hand, if it is determined that the predetermined time has passed, then the driving controller 440' determines whether or not the male part 11 has been attached to the female part 12 based on the output signal of the attachment sensing means 100 (s14). As a result, if it is determined that the male part 11 has not been attached to the female part 12, the driving means 420' is rotationally driven (s15) to move the rod-like body 410' from the contained position to the projected position. This allows the rod-like body 410' to project along the tongue 11a. Then, the processing returns to step 11.

If it is determined in step 14 that the male part 11 has been attached to the female part 12, then the driving controller 440' determines whether or not the male part 11 has been detached from the female part 12 based on the output signal of the attachment sensing means 100 (s16). That is, it is determined whether or not the seat belt has been detached after finishing driving. As a result, if it is determined that the seat belt has not been detached, the processing of step 16 is repeated. If it is determined that the seat belt has been detached, the driving controller 440' activates the timer circuit, and determines in reference to the counting value of the timer circuit whether or not a predetermined time (e.g., about 10 minutes) has passed after the male part 11 was detached from the female part 12 (s17). As a result, if it is determined that the predetermined time has not passed, then the driving controller 440' determines whether or not the motor 20 has stopped (i.e., the predetermined flag on the memory of the driving controller 440' is set) (s18). That is, whether or not the driving is actually finished is determined. As a result, if it is determined that the motor 20 has not stopped, the processing returns to step 17. That is, as the driving is considered as not having been actually finished, and the insertion slot 12a of the female part 12 is kept in the opened state (see FIGS. 2 and 3). This allows the driver to restart the driving without being subjected to the alcohol concentration determination by using the breath component concentration determining means 300 until the predetermined time of step 17 has passed.

If it is determined that the predetermined time has passed in step 17, or if it is determined that the motor 20 has stopped in step 18, then the driving means 420' is rotationally driven (s19) to move the rod-like body 410' from the contained position to the projected position. This allows the rod-like body 410' to project along the tongue 11a. Then, the processing returns to step 11.

In the above-described safe-driving promotion system, if the determination unit 320 of the breath component concentration determining means 300 determines that alcohol of the reference value or above is contained in the breath of the driver, then the open signal β is not outputted from the signal output unit 330 of the breath component concentration determining means 300. Therefore, the rod-like body 410' of the attachment preventing means 400' is kept in a projected state along the tongue 11a, which disables the female part 12 of the seat belt to receive the male part 11. Thus, when the seat belt cannot be attached, the first start permission signal α is not outputted from the attachment sensing means 100 provided in the male part 11, and the start controlling means 200 does not put the motor 20 of the automobile 1 into the startable state, so that the driver cannot start the motor 20. Thus, the drunk driving of the driver can be effectively prevented.

On the other hand, if the determination unit 320 of the breath component concentration determining means 300 determines that the alcohol of the reference value or above is not contained in the breath of the driver, the open signal β is outputted from the signal output unit 330 of the breath component concentration determining means 300. In response to the signal, the rod-like body 410' of the attachment preventing means 400' moves from the projected position to the contained position to be contained in the housing 401'. This enables the female part 12 to receive the male part 11. Then, if the male part 11 of the seat belt is not attached to the female part 12, the first start permission signal α is not outputted from the attachment sensing means 100 provided in the male part 11. Since the safe-driving promotion system has such a configuration that if the first start permission signal α is not inputted, the body controller 210 of the start controlling means 200 does not put the motor 20 of the automobile 1 into the startable state. Consequently, the safe-driving promotion system can force the driver to wear the seat belt.

It should be noted that any type of attachment preventing means may be used, as long as it prevents the attachment between the male part 11 and the female part 12 of the seat belt, and allows the attachment only when the first start permission signal α of the breath component concentration determining means 300 is inputted.

Therefore, although it is described above that the attachment preventing means 400 is configured to open and close the insertion slot 12a of the female part 12, it may also be configured to make the rod-like body project out of and retract into the insertion slot 12a of the female part 12. That is, the configuration of the attachment preventing means 400' can be provided in the female part 12.

Moreover, although it is described above that the attachment preventing means 400' is configured to make the rod-like body 410' projected in such a manner as to move in and out along the tongue 11a of the male part 11, it may also be configured such that the tongue 11a itself instead of the rod-like body 410' can move into and out of a male part main body, as will be described in detail in Embodiment 8. That is, the tongue 11a is projected only when the first start permission signal α is received, and when being inserted into the insertion slot 12a of the female part 12, the tongue 11a can be locked by a locking mechanism provided in the female part 12.

Furthermore, the locking mechanism can be an attachment sensing means. More specifically, the locking mechanism may lock the tongue 11a only when the first start permission signal α is inputted.

Although it is described above the breath component concentration determining means 300 is a mobile device, it can be obviously provided integrally with the automobile 1. Similarly, the biometric means 800 and/or the GPS transmitter 900 may also be provided integrally. However, only the GPS transmitter 900 can be separated from the breath component concentration determining means 300 to be provided in the automobile 1.

Although it is described above that the sensing means 310 of the breath component concentration determining means 300 detect the alcohol, it may be adapted to detect drug. Of course, the sensing means 310 may detect both of alcohol and drug.

EMBODIMENT 3

Figure 10:
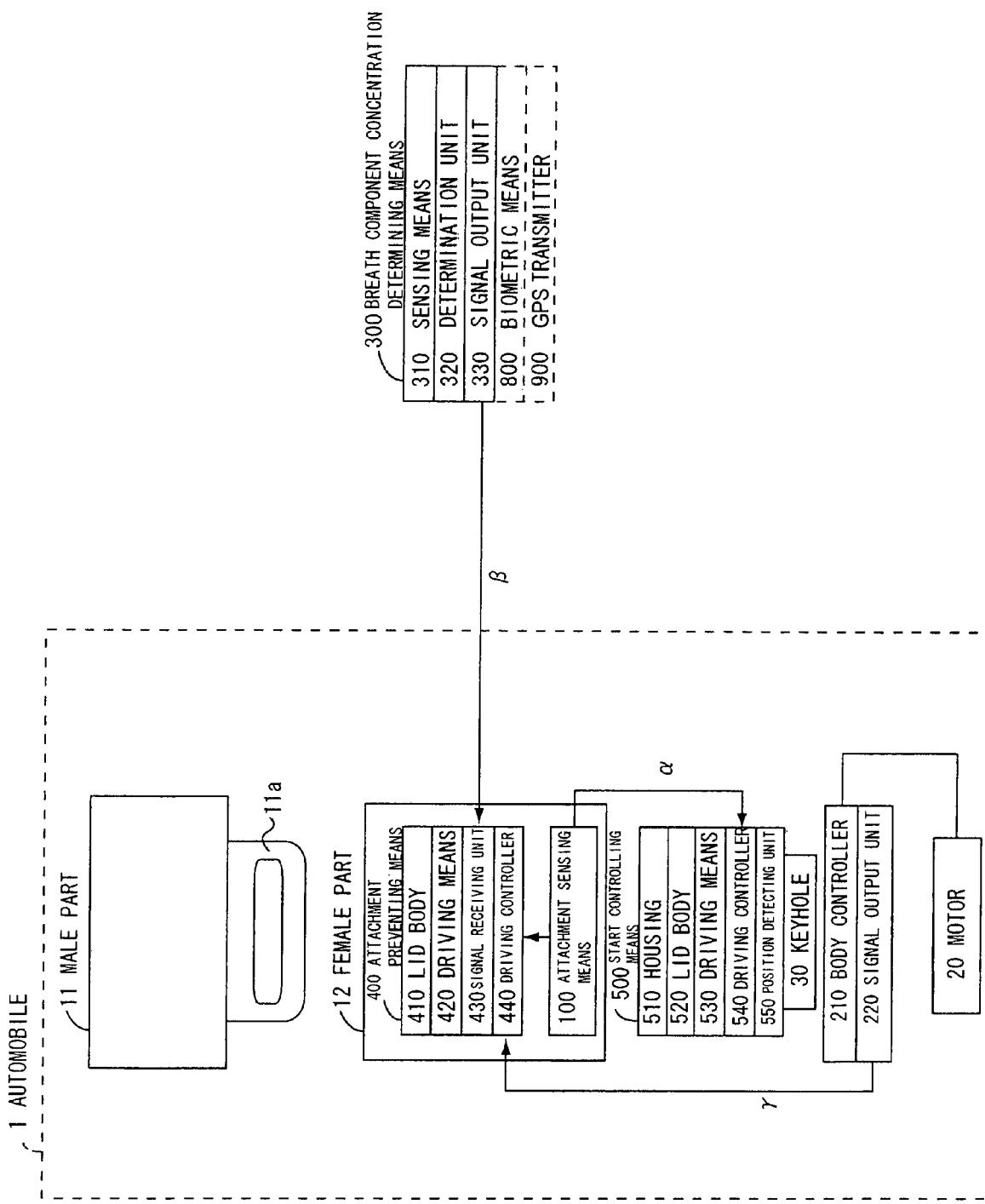
FIG. 10 is a block diagram of a safe-driving promotion system according to a third embodiment of the present invention.
Figure 11:
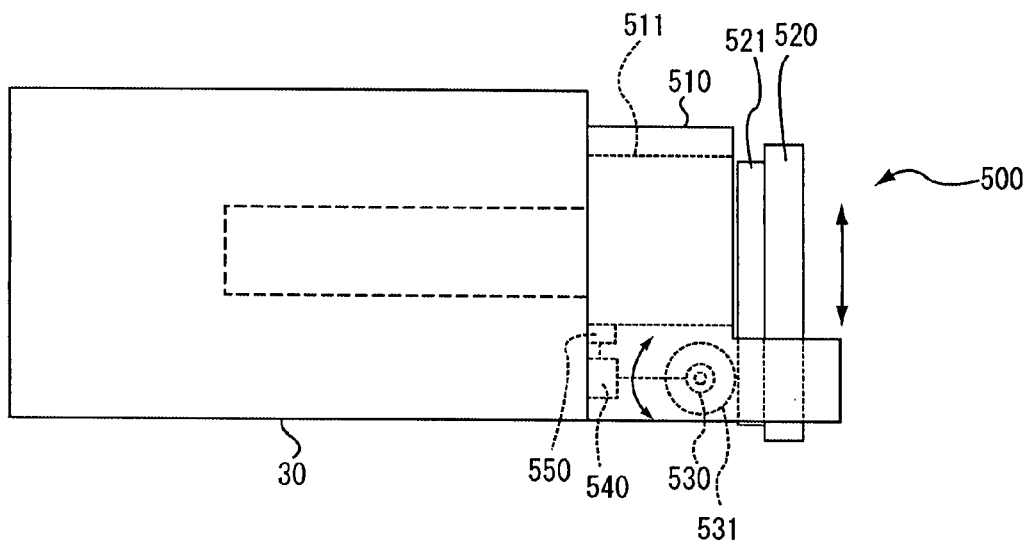
FIG. 11 is a schematic side view showing start controlling means, in which an inside of the same system can be seen transparently.
Figure 11:
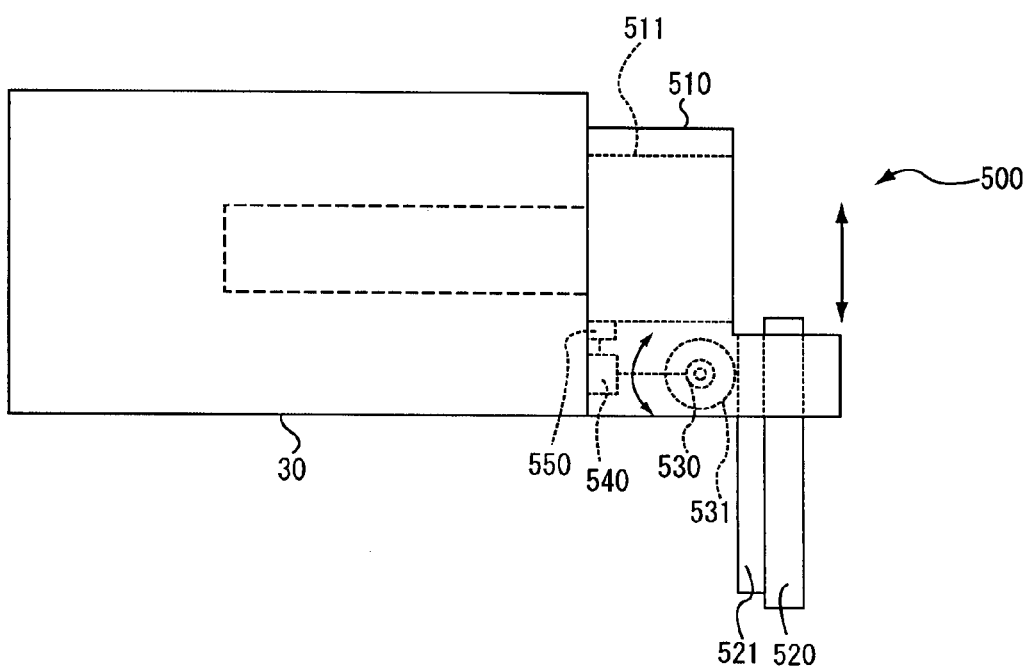
Figure 12:
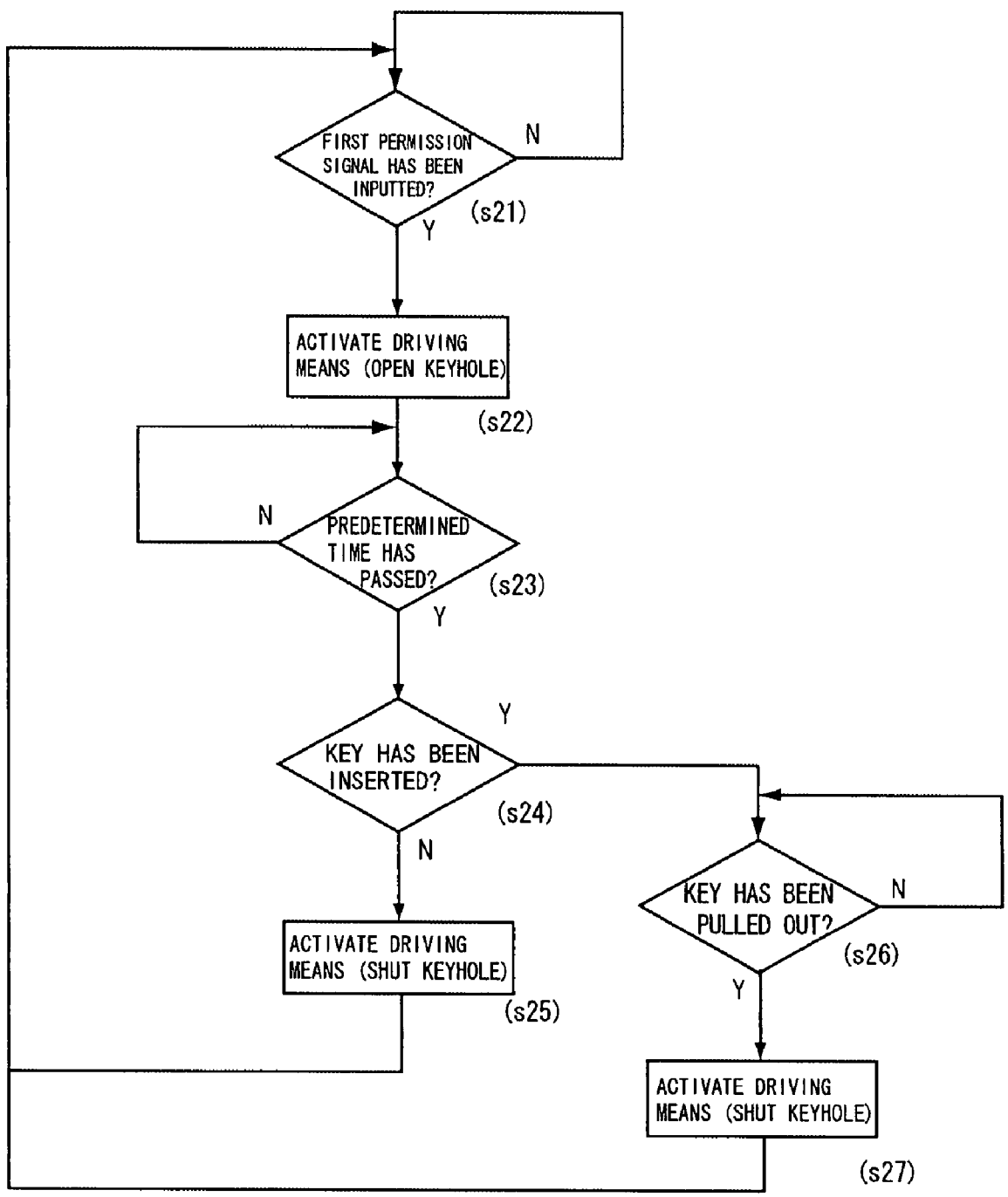
FIG. 12 is a flowchart of a keyhole opening and closing program processed by a driving controller of the start controlling means of the same system.
Figure 13:
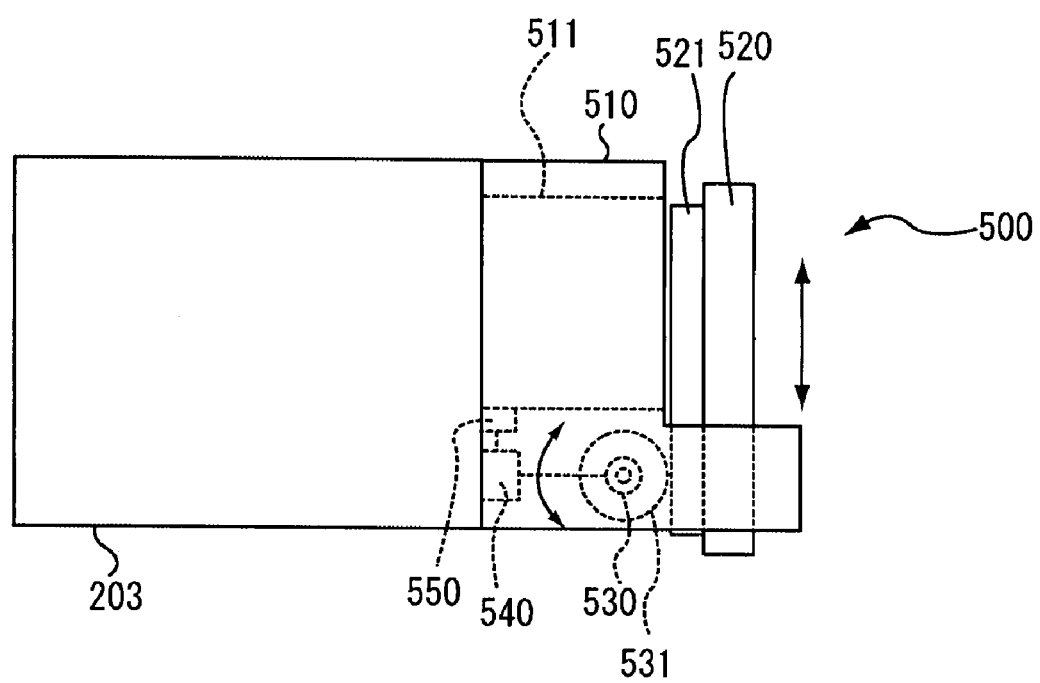
FIG. 13 is a schematic side view of the start controlling means in which an inside can be seen transparently, showing a design modification of the same system.
Figure 14:
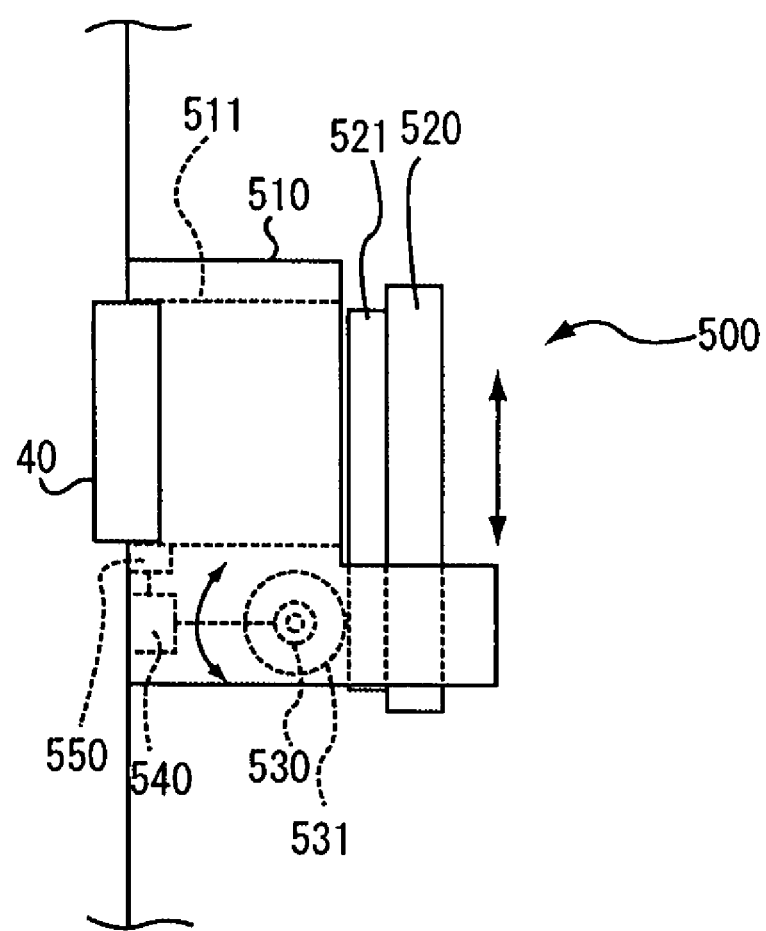
FIG. 14 is a schematic side view of the start controlling means in which an inside can be seen transparently, showing other design modification of the same system.

Next, referring to the drawings, a safe-driving promotion system according to a third embodiment of the present invention is described. FIG. 10 is a block diagram of the safe-driving promotion system according to the third embodiment of the present invention. FIG. 11 is a schematic side view showing start controlling means, in which an inside of the same system can be seen transparently. FIG. 12 is a flowchart of a keyhole opening and closing program processed by a driving controller of the start controlling means of the same system. FIG. 13 is a schematic side view of the start controlling means in which an inside can be seen transparently, showing a design modification of the same system. FIG. 14 is a schematic side view of the start controlling means in which an inside can be seen transparently, showing other design modification of the same system.

The safe-driving promotion system shown in FIG. 10 is different from the safe-driving promotion system of Embodiment 1 in a configuration of start controlling means 500. Therefore, the differences are described in detail, and the overlapping features are omitted. A reference numeral 500 is newly given to the start controlling means.

The start controlling means 500 is provided in a keyhole 30 of the automobile 1, and is configured to open and close the keyhole 30 (namely, first blocking means). More specifically, as shown in FIG. 11, the start controlling means 500 has a cylindrical housing 510 mounted on an edge portion of the keyhole 30, a lid body 520 for opening and closing an opening 511 of this housing 510, driving means 530 for moving this lid body 520 from a shutting position where the opening 511 of the housing 510 is shut (FIG. 11(a)) to an opening position where the opening 511 is opened (FIG. 11(b)), a driving controller 540 that controls the driving of the driving means 530, and a position sensing unit 550 such as a photosensor and a limit switch that senses the insertion of a key into the keyhole 30.

The lid body 520 is a resin-molded component, and is provided with a rack gear 521 extending in a moving direction on one surface. The driving means 530 is a motor, the head of which is provided a pinion 531 for engagement with the rack gear 521 of the lid body 520. That is, rotational motion of the driving means 530 is converted to linear motion of the lid body 520.

The driving controller 540 uses a microcomputer or the like. It has an input port to connect the attachment sensing means 100, and also has an output port to connect the driving means 530. A keyhole opening and closing program shown in FIG. 12 is recoded on a memory of the driving controller 540. That is, by processing the keyhole opening and closing program, the driving controller 540 rotationally drives the driving means 530 in accordance with the first start permission signal α of the attachment sensing means 100 to move the lid body 520 from the shutting position to the opening position. The driving controller 540 determines whether or not a key has been inserted into the keyhole 30 based on an output signal of the position detecting unit 550, and if it is determined that the key has not been inserted, the controller 540 rotationally drives the driving means 530 to move the lid body 520 from the opening position to the shutting position.

The body controller 210 has a basic function of generally controlling the automobile 1, such as controlling the start of the motor 20 of the automobile 1, and a function of making the signal output unit 220 output the motor state signal γ to the driving controller 440 every time the motor 20 starts and stops. That is, the function as the start controlling means is excluded.

Hereinafter, the usage of the safe-driving promotion system of the above-described configuration is described. Detailed descriptions will also be made on the keyhole opening and closing program shown in FIG. 12 which is processed by the driving controller 540 of the start controlling means 500. Further, the operations of the respective units and parts are described.

First, before the motor 20 of the automobile 1 is started, the lid body 410 of the attachment preventing means 400 covers the insertion slot 12a of the female part 12 of the seat belt (see FIGS. 2(a) and 3(a)), while the lid body 520 of the start controlling means 500 covers the keyhole 30 as shown in FIG. 11(a).

As in Embodiment 1, in starting the motor 20 of the automobile 1, the driver is subjected to the concentration determination of the alcohol contained in his or her own breath using the breath component concentration determining means 300. As a result of the determination, when the attachment preventing means 400 opens the insertion slot 12a of the female part 12 of the seat belt, the driver is allowed to attach the male part 11 of the seat belt to the female part 12. In response to the attachment, the first start permission signal α is outputted from the attachment sensing means 100.

The start controlling means 500 constantly processes the keyhole opening and closing control program shown in FIG. 12, and determines whether or not the first start permission signal α has been inputted (s21). As a result, if it is determined that the first start permission signal α has been inputted, the start controlling means 500 activates a timer circuit and rotationally drives the driving means 530 to move the lid body 520 from the shutting position to the opening position (s22). The keyhole 30 is thereby opened and the key can be inserted into the keyhole 30 to start the motor 20.

After step 22, the start controlling means 500 determines whether or not a predetermined time has passed after the keyhole 30 was opened in reference to a counting value of the timer circuit (s23). As a result, if it is determined that the predetermined time has not passed, the processing of step 23 is repeated. On the other hand, if it is determined that the predetermined time has passed, then the start controlling means 500 determines whether or not the key has been inserted into the keyhole 30 based on the output signal of the position sensing unit 550 (s24). As a result, if it is determined that the key has not been inserted into the keyhole 30, the start controlling means 500 rotationally drives the driving means 530 (s25) to move the lid body 520 from the opening position to the shutting position. The lid body 520 thereby covers the keyhole 30. Then, the processing returns to step 21.

If it is determined in step 24 that the key has been inserted into the keyhole 30, then the start controlling means 500 determines whether or not the key has been pulled out of the keyhole 30 (s26). As a result, if it is determined that the key has not been pulled out, the processing of step 26 is repeated. If it is determined that it has been pulled out, the start controlling means 500 rotationally drives the driving means 530 (s27) to move the lid body 520 from the opening position to the shutting position. The lid body 520 thereby shut the keyhole 30. Then, the processing returns to step 21.

In the above-described safe-driving promotion system, if the determination unit 320 of the breath component concentration determining means 300 determines that the breath of the driver contains alcohol of the reference value or above, then the open signal β is not outputted from the signal output unit 330 of the breath component concentration determining means 300. Therefore, because the lid body 410 of the attachment preventing means 400 is kept in the shutting position covering the insertion slot 12a of the female part 12 of the seat belt, the male part 11 of the seat belt cannot be inserted into the female part 12. Thus, when the seat belt cannot be fastened, the first start permission signal α is not outputted from the attachment sensing means 100 provided in the female part 12, the start controlling means 500 will not open the keyhole 30 of the automobile 1, so that the driver cannot start the motor 20. Thus, the drunk driving of the driver can be effectively prevented.

On the other hand, if the determination unit 320 of the breath component concentration determining means 300 determines that the breath of the driver contains the alcohol of the reference value or above, the open signal β is outputted from the signal output unit 330 of the breath component concentration determining means 300. In response to the signal, the lid body 410 of the attachment preventing means 400 moves from the shutting position to the opening position to open the insertion slot 12a of the female part 12. This enables the male part 11 to be inserted into the female part 12. Then, if the male part 11 of the seat belt is not attached to the female part 12, the first start permission signal α is not outputted from the attachment sensing means 100 provided in the female part 12. Since the driving controller 540 of the start controlling means 500 opens the keyhole 30 of the automobile 1 only when receiving the first start permission signal α, the driver can be forced to wear the seat belt.

Additionally, since the start controlling means 500 is simply mounted on the keyhole 30, the automobile 1 does not need to be largely modified in design. Therefore, the system can be realized in reduced cost.

Although it is described above that the start controlling means 500 is adapted to open and close the keyhole 30, a rod-like body may project and retract within the keyhole 30. That is, a configuration like the attachment preventing means 400' can be employed.

Moreover, the start controlling means 500 may be mounted on other locations than the keyhole 30. Particularly, as shown in FIG. 13, it can also be mounted as second blocking means on the signal receiving unit 203 (receiving means) that receives the second start permission signal δ. The signal receiving unit 203 is outputted from the signal output means 700 (see FIG. 1) such as an immobilizer so as to put the motor 20 of the automobile 1 into the startable state. Alternatively, as shown in FIG. 14, the start controlling means 500 can be mounted as third blocking means in a start operating unit 40 operated for starting the motor 20 of the automobile 1.

Furthermore, the start controlling means 500 can obviously be applied to the safe-driving promotion system of Embodiment 2. In this case, the body controller 210 is modified in design as described above.

EMBODIMENT 4

Figure 15:
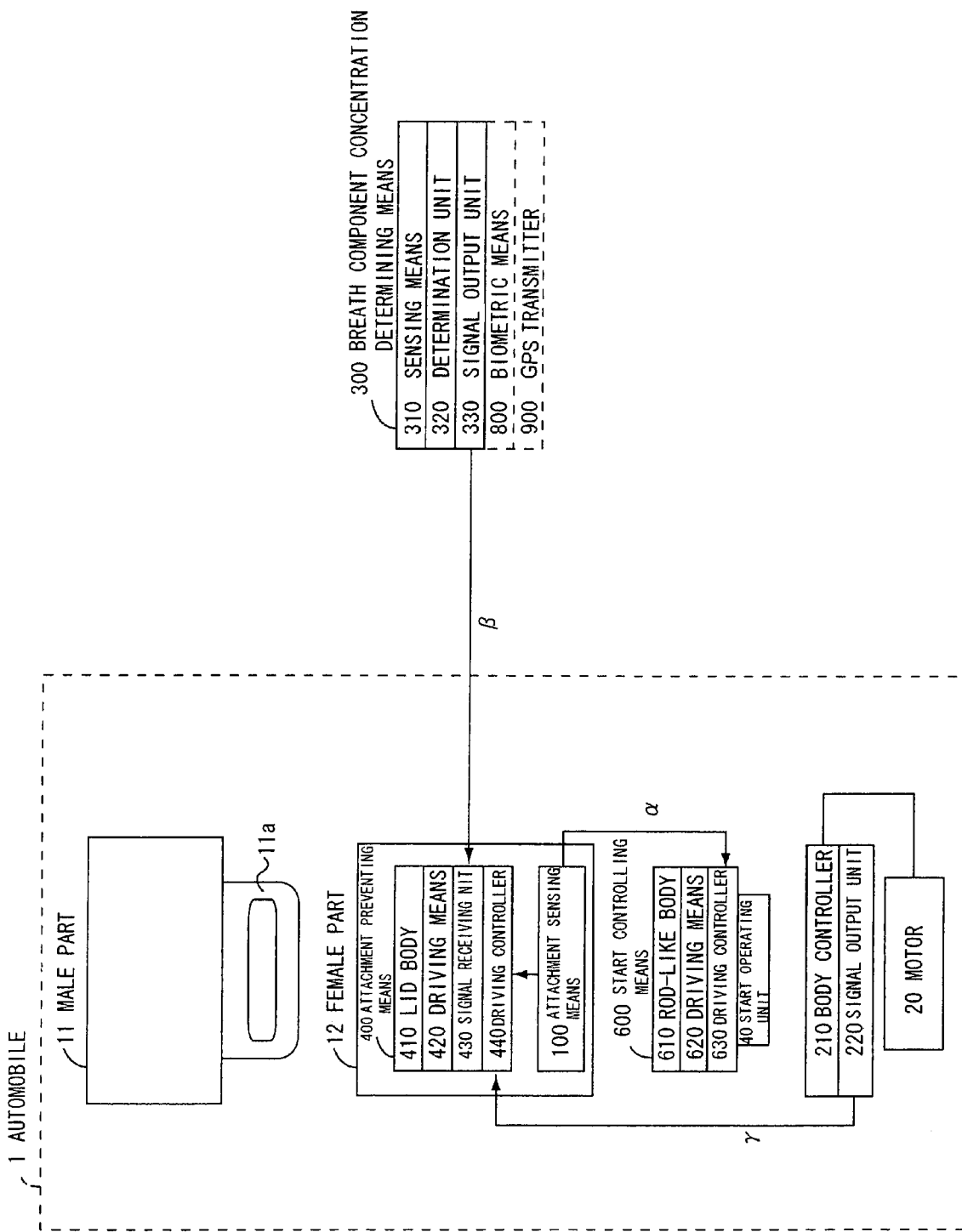
FIG. 15 is a block diagram of a safe-driving promotion system according to a fourth embodiment of the present invention.
Figure 16:
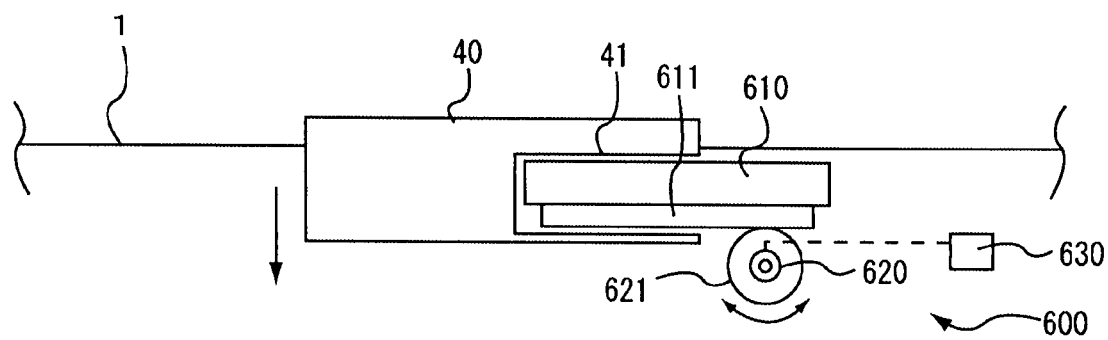
FIG. 16 is a schematic side view showing start controlling means, in which an inside of the same system can be seen transparently.
Figure 16:
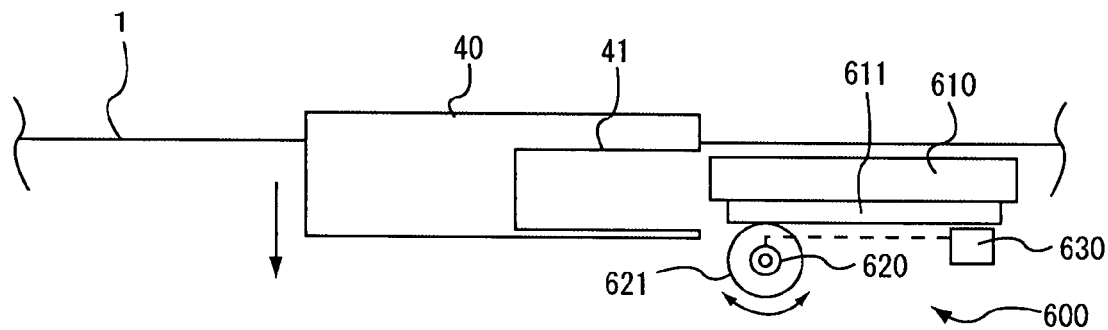
Figure 17:
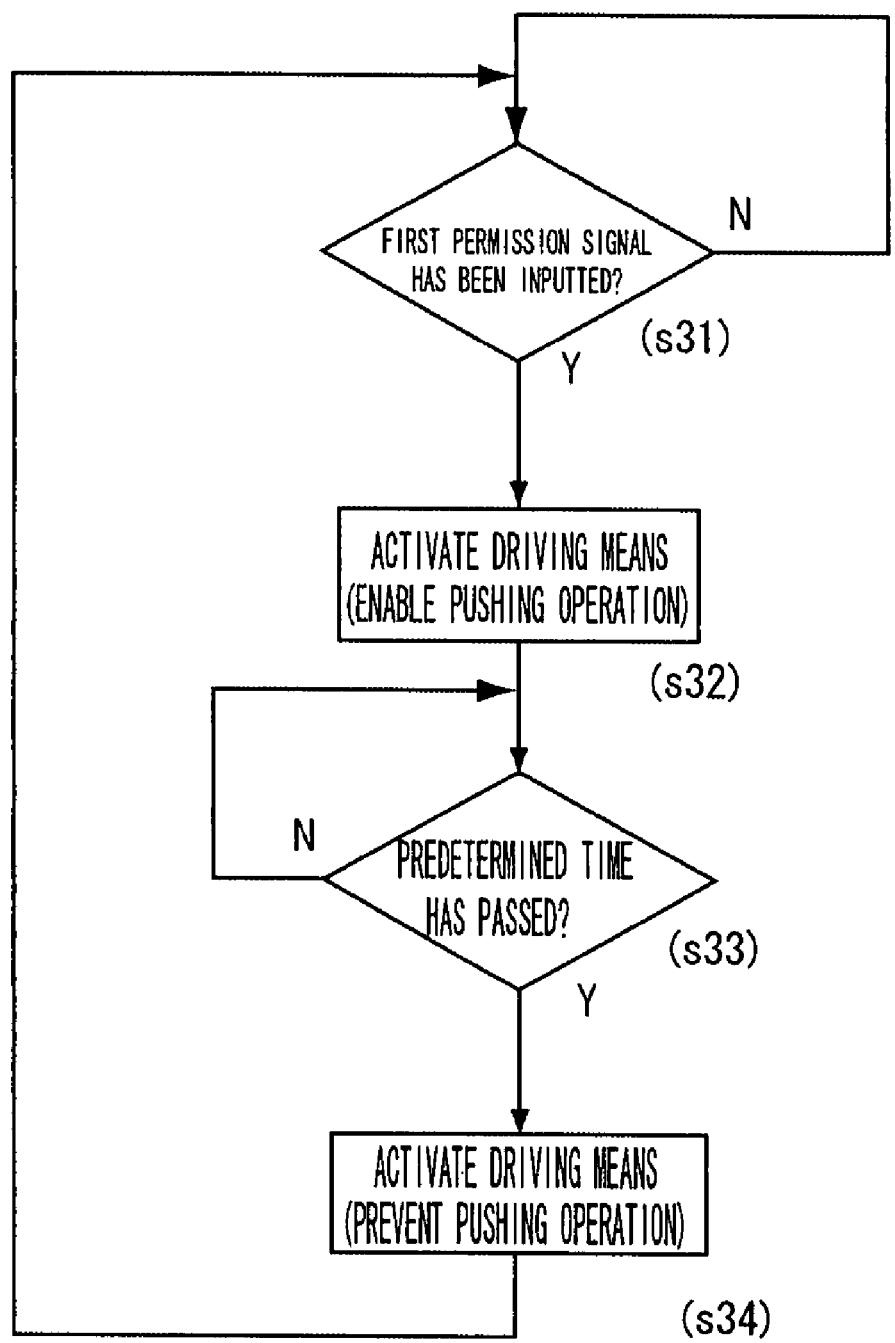
FIG. 17 is a flowchart of a start operation preventing program processed by a driving controller of the start controlling means of the same system.

Next, referring to the drawings, a safe-driving promotion system according to a fourth embodiment of the present invention is described. FIG. 15 is a block diagram of the safe-driving promotion system according to the fourth embodiment of the present invention. FIG. 16 is a schematic side view showing start controlling means, in which an inside of the same system can be seen transparently. FIG. 17 is a flowchart of a start operation preventing program processed by a driving controller of the start controlling means of the same system.

The safe-driving promotion system shown in FIG. 15 is different from the safe-driving promotion system of Embodiment 1 in that the automobile 1 has the start operating unit 40 operated to start the motor 20 of the automobile 1, and that start controlling means 600 serves as operation preventing means for preventing the operation of the start operating unit 40. Therefore, the differences are described in detail, and descriptions of the overlapping are omitted. A reference numeral 600 is newly given to the start controlling means.

The start operating unit 40 is a push switch provided in the automobile 1. An edge portion of the start operating unit 40 is provided with an engagement part 41 which is a recess for engagement with a rod-like body 610 of the start controlling means 600. After pushing operation, the start operating unit 40 automatically recovers by a spring not shown.

The start controlling means 600 is provided in the automobile 1, and is engagement means for engaging with the start operating unit 40 to prevent the pushing operation of the start operating unit 40. More specifically, as shown in FIG. 16, the start controlling means 600 has the rod-like body 610 for engagement with the engagement part 41 of the start operating unit 40, driving means 620 for moving the rod-like body 610 from an engaged position where the rod-like body 610 is engaged with the engagement part 41 (see FIG. 16(*a*)) to a retracted position where it is not engaged with the engagement part 41 (see FIG. 16(*b*)), and a driving controller 630 that controls the driving of the driving means 620.

The rod-like body 610 is a rectangular resin-molded component, and is provided with a rack gear 611 extending in a moving direction on one surface. The driving means 620 is a motor, the head of which is provided with a pinion 621 for engagement with the rack gear 611 of the rod-like body. That is, rotational motion of the driving means 620 is converted to linear motion of the rod-like body 610.

The driving controller 630 uses a microcomputer or the like. It has an input port to connect the attachment sensing means 100, and also has an output port to connect the driving means 620. A start operation preventing program shown in FIG. 17 is recoded on a memory of the driving controller 630. That is, by processing the start operation preventing program, the driving controller 630 rotationally drives the driving means 620 in accordance with the first start permission signal $\alpha$ of the attachment sensing means 100 to move the rod-like body 610 from the engaged position to the retracted position.

The body controller 210 has a basic function of generally controlling the automobile 1, such as controlling the start of the motor 20 of the automobile 1, and a function of making the signal output unit 220 output the motor state signal $\gamma$ to the driving controller 440 every time the motor 20 starts and stops. That is, the function as the start controlling means is excluded.

Hereinafter, the usage of the safe-driving promotion system of the above-described configuration is described. Detailed descriptions will also be made on the start operation preventing program shown in FIG. 17 which is processed by the driving controller 630 of the start controlling means 600. Further, the operations of the respective units and parts are described.

First, before the motor 20 of the automobile 1 is started, the lid body 410 of the attachment preventing means 400 covers the insertion slot 12a of the female part 12 of the seat belt (see FIGS. 2(a) and 3(a)), while the rod-like body 610 of the start controlling means 600 is engaged with the engagement part 41 of the start operating unit 40, as shown in FIG. 16(a).

In starting the motor 20 of the automobile 1, the driver is subjected to the concentration determination of the alcohol contained in his or her own breath by using the breath component concentration determining means 300 as in Embodiment 1. As a result of the determination, when the insertion slot 12a of the female part 12 of the seat belt is opened by the attachment preventing means 400, the driver is allowed to attach the male part 11 of the seat belt to the female part 12. In response to the attachment, the first start permission signal $\alpha$ is outputted from the attachment sensing means 100.

The start controlling means 600 constantly processes a start controlling preventing program shown in FIG. 17, and determines whether or not the first start permission signal $\alpha$ has been inputted (s31). As a result, if it is determined that the first start permission signal $\alpha$ has been inputted, the start controlling means 600 activates a timer circuit and rotationally drives the driving means 620 to move the rod-like body 610 from the engaged position to the retracted position (s32). Since the movement enables the start operating unit 40 to be pushed down, the driver can start the motor 20.

After step 32, the start controlling means 600 determines, in reference to a counting value of the timer circuit, whether or not a predetermined time has passed after the start operating unit 40 was enabled to be pushed down (s33). As a result, if it is determined that the predetermined time has passed, the driving means 620 is rotationally driven (s34) to move the rod-like body 610 from the retracted position to the engaged position. The moved rod-like body 610 is engaged with the engagement part 41 and prevents the start operating unit 40 to be pushed down. Then, the processing returns to step 31.

In the above-described safe-driving promotion system, if the determination unit 320 of the breath component concentration determining means 300 determines that the breath of the driver contains alcohol of the reference value or above, then the open signal $\beta$ is not outputted from the signal output unit 330 of the breath component concentration determining means 300. Therefore, because the lid body 410 of the attachment preventing means 400 is kept in the shutting position covering the insertion slot 12a of the female part 12 of the seat belt, the male part 11 of the seat belt cannot be inserted into the female part 12. Thus, when the seat belt cannot be fastened, the first start permission signal $\alpha$ is not outputted from the attachment sensing means 100 provided in the female part 12, and the start controlling means 600 will not enable the start operating unit 40 to be pushed, so that the driver cannot start the motor 20. Thus, the drunk driving of the driver can be effectively prevented.

On the other hand, if the determination unit 320 of the breath component concentration determining means 300 determines that the breath of the driver contains the alcohol of the reference value or above, the open signal $\beta$ is outputted from the signal output unit 330 of the breath component concentration determining means 300. In response to the signal, the lid body 410 of the attachment preventing means 400 moves from the shutting position to the opening position to open the insertion slot 12a of the female part 12. This enables the male part 11 to be inserted into the female part 12. Then, if the male part 11 of the seat belt is not attached to the female part 12, the first start permission signal $\alpha$ is not outputted from the attachment sensing means 100 provided in the female part 12. Since the driving controller 630 of the start controlling means 600 enables the start operating unit 40 to be pushed down only when receiving the first start permission signal $\alpha$, the driver can be forced to wear the seat belt.

Additionally, since the start controlling means 600 is simply engaged with the start operating unit 40, the automobile 1 does not need to be largely modified in design. Therefore, the system can be realized in reduced cost.

Any type of start controlling means 600 may be used as long as it serves as the operation preventing means for preventing the operation of the start operating unit. Although it is described in the above Embodiment 4 that the rod-like body 610 is engageable with the engagement part 41 of the start operating unit 40, the start controlling means 600 can also be provided within the start operating unit 40 so that the rod-like body 610 is engaged with an engagement part provided in a housing part of the automobile 1 where the start operating unit 40 is provided. Also, the operation preventing means can be configured such that a shift lever of the automobile is locked by a rod-like body not to operate the automobile.

The start controlling means 600 can obviously be applied to the safe-driving promotion system of Embodiment 2. In this case, the body controller 210 is modified in design as described above.

Any kind of the attachment sensing means 100 may be used as long as it is provided in the male part 11 or the female part 12 of the seat belt and can sense the attachment between the male part 11 and the female part 12. For example, the attachment sensing means 100 can be connected electrically or magnetically at the time of the attachment between the male part 11 and the female part 12 of the seat belt, and this connection allows the first start permission signal $\alpha$ to be outputted. Moreover, the male part 11 and the female part 12 of the seat belt can be connecting terminals connected electrically or magnetically at the time of the attachment between the male part 11 and the female part 12 of the seat belt, and the connection is recognized by the start controlling means as the first start permission signal α. In this case, the male part 11 and the female part 12 of the seat belt compose the attachment sensing means 100.

EMBODIMENT 5

Figure 18:
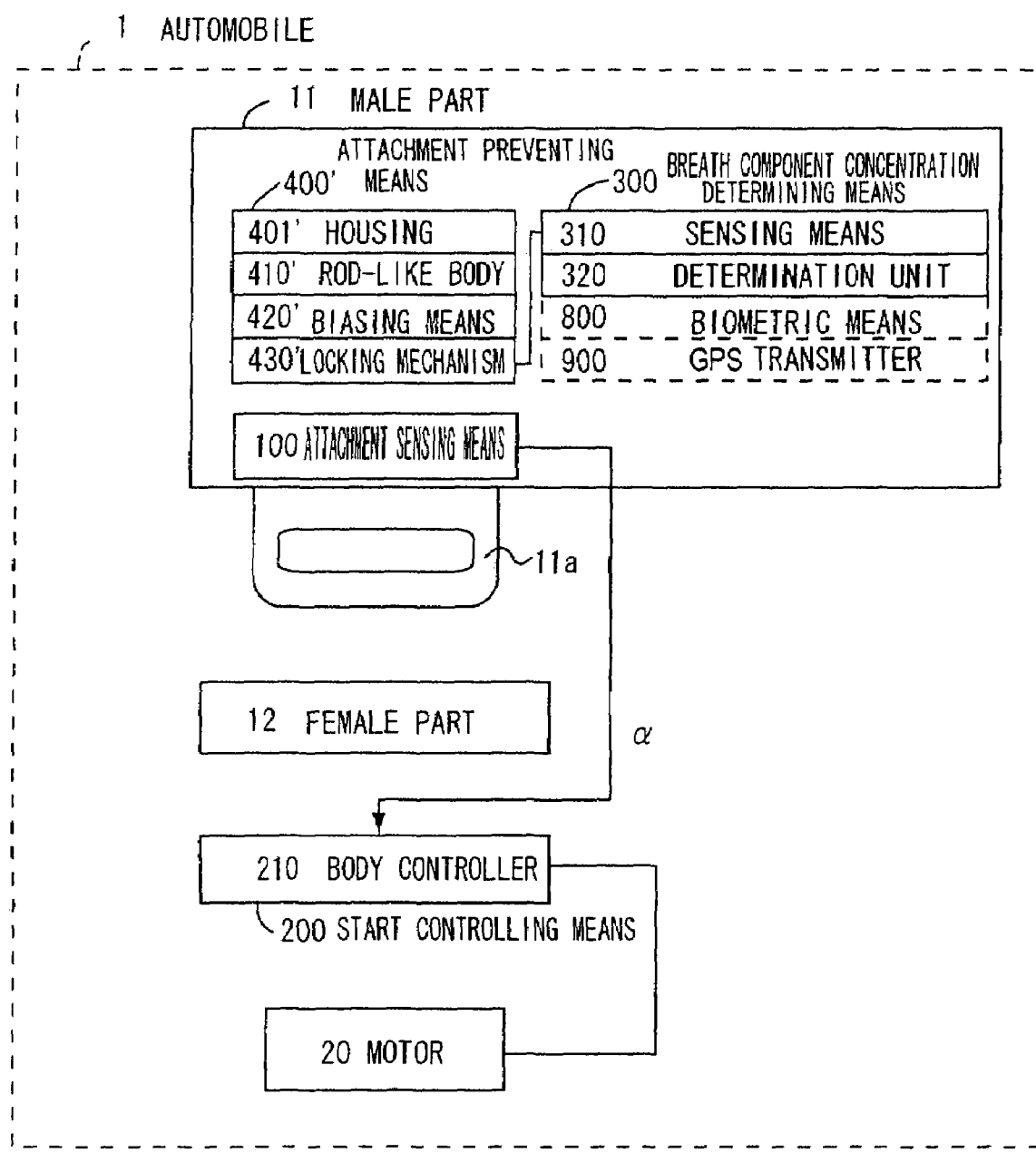
FIG. 18 is a block diagram of a safe-driving promotion system according to a fifth embodiment of the present invention.
Figure 19:
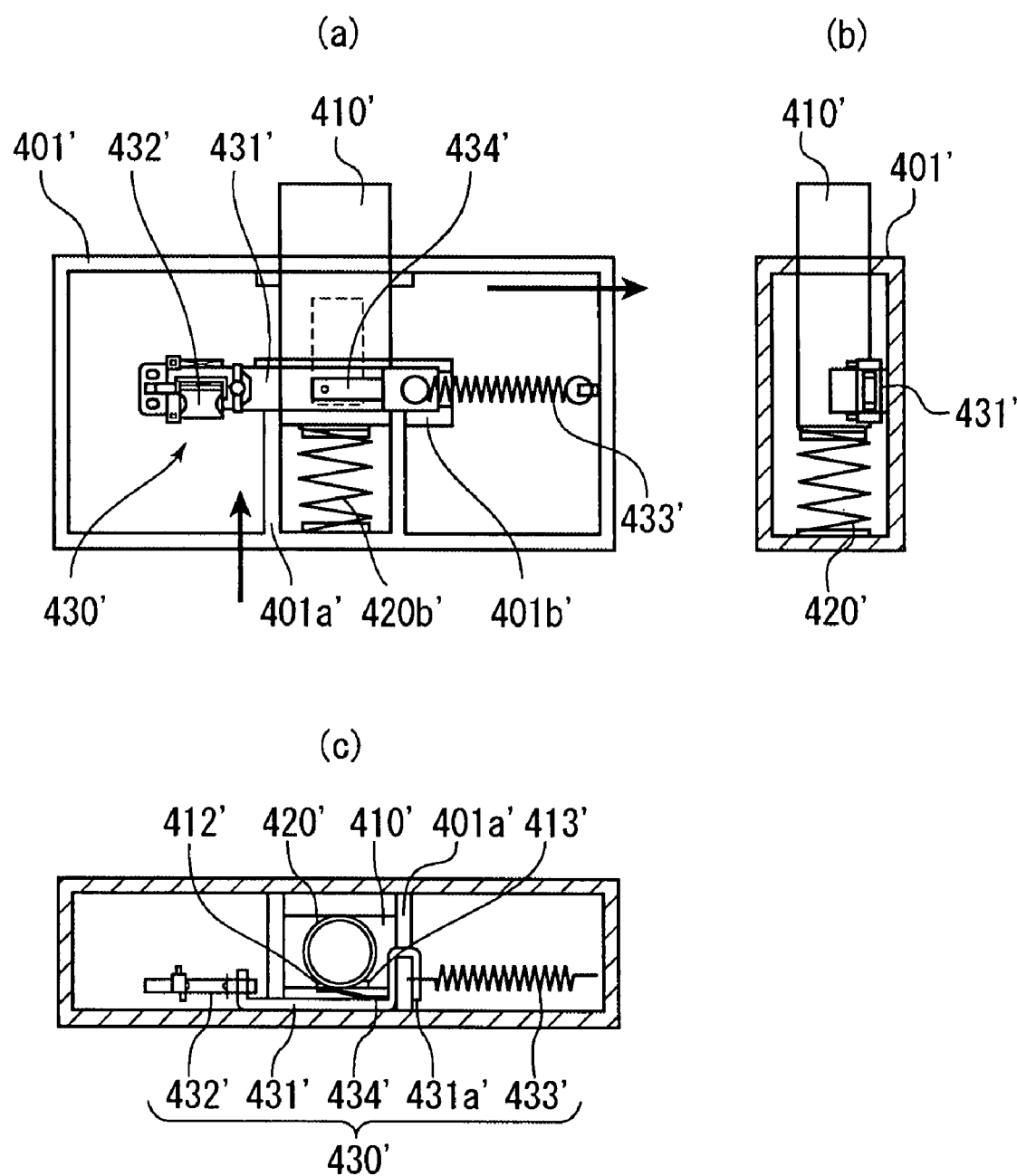
FIG. 19 is schematic views showing an internal structure in a state where a rod-like body of attachment preventing means of the same system is projected, (a) being a plane view in which an inside can be seen transparently, (b) being a vertical cross-sectional view, (c) being a traverse cross-sectional view.
Figure 20:
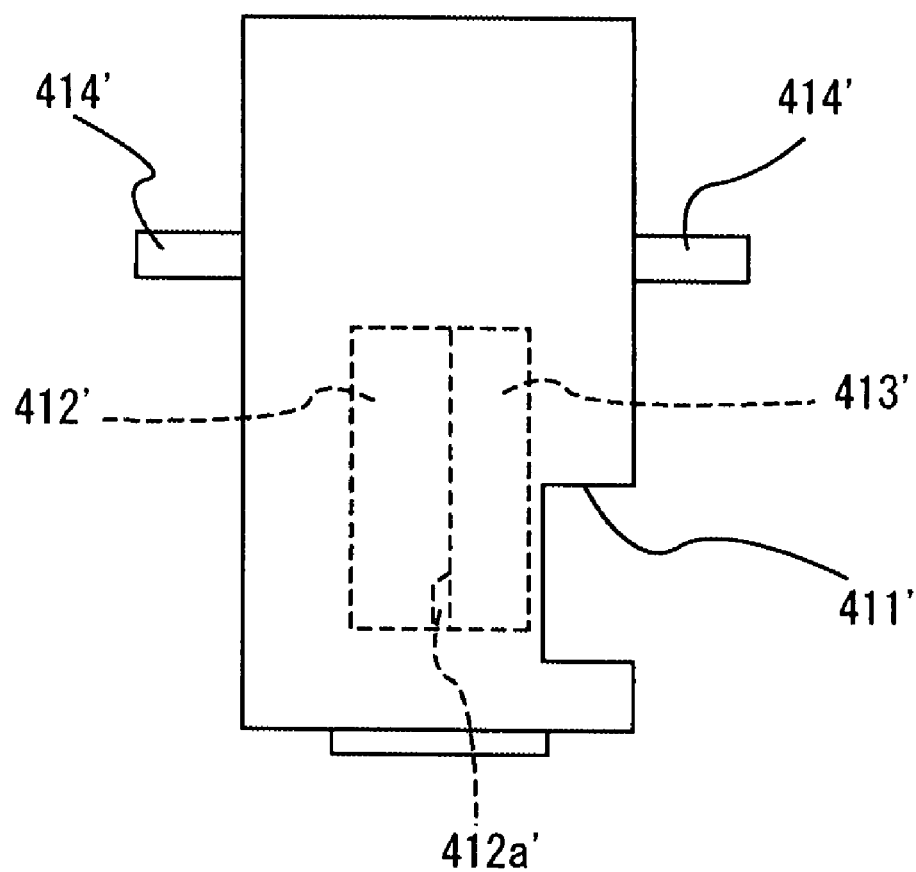
FIG. 20 is a schematic plane view of the rod-like body of the same attachment preventing means.
Figure 21:
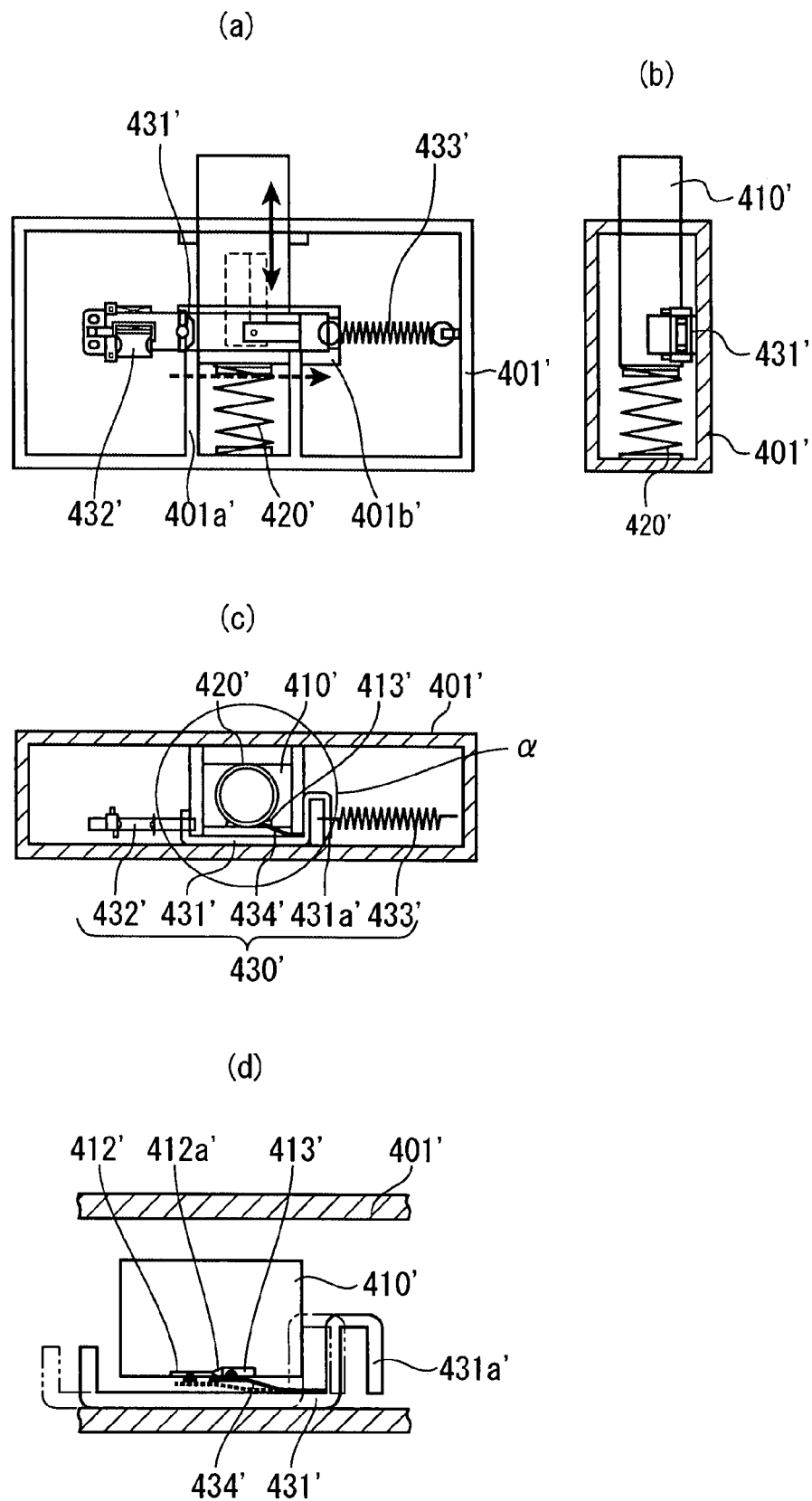
FIG. 21 is schematic views showing the internal structure in a containable state of the rod-like body of the same attachment preventing means, (a) being a plane view in which an inside can be seen transparently, (b) being a vertical cross-sectional view, (c) being a traverse cross-sectional view, (d) being an enlarged view of an α portion with biasing means excluded.
Figure 22:
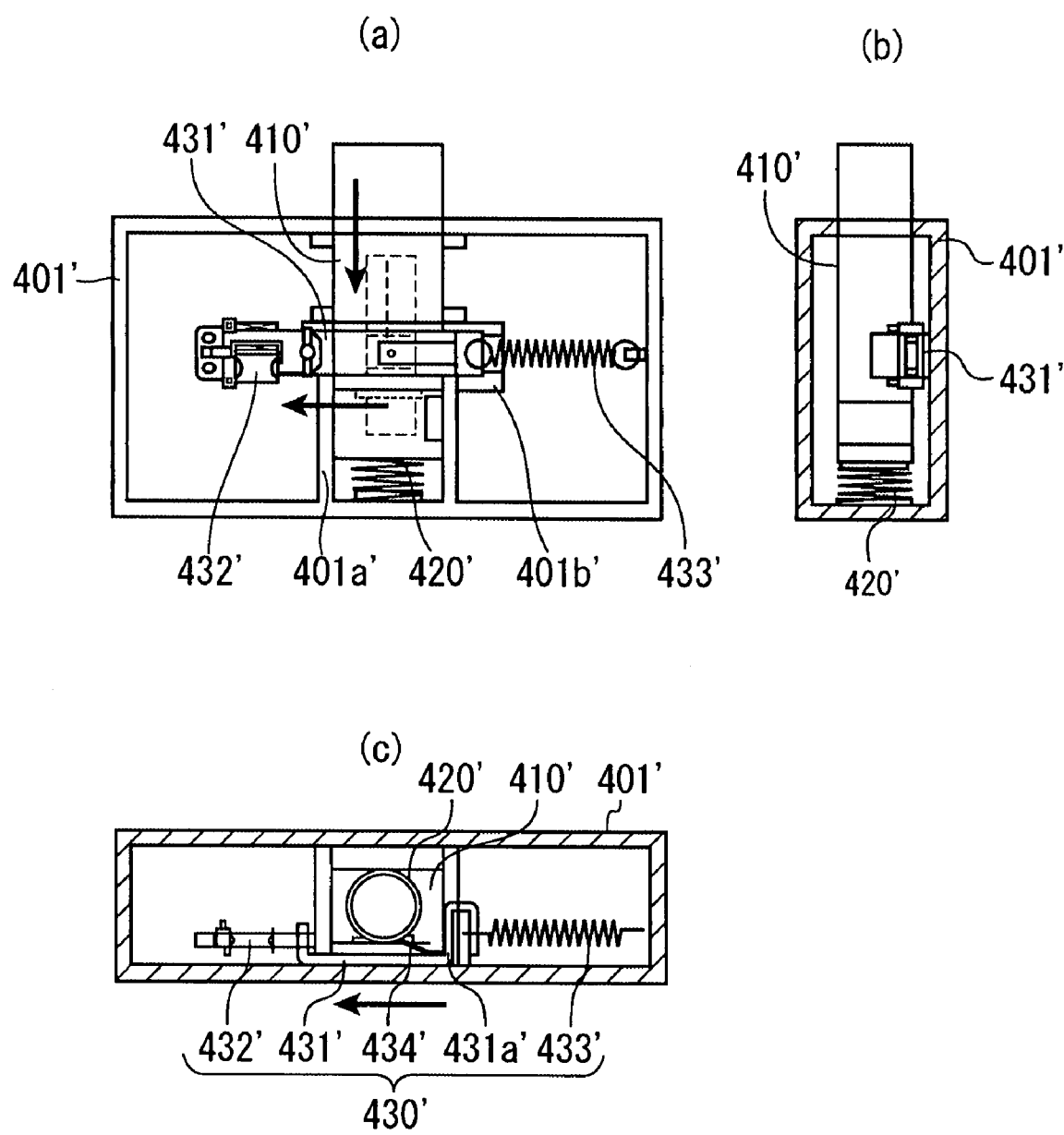
FIG. 22 is schematic views showing the internal structure in a contained state of the rod-like body of the same attachment preventing means, (a) being a plane view in which an inside can be seen transparently, (b) being a vertical cross-sectional view, (c) being a traverse cross-sectional view.
Figure 23:
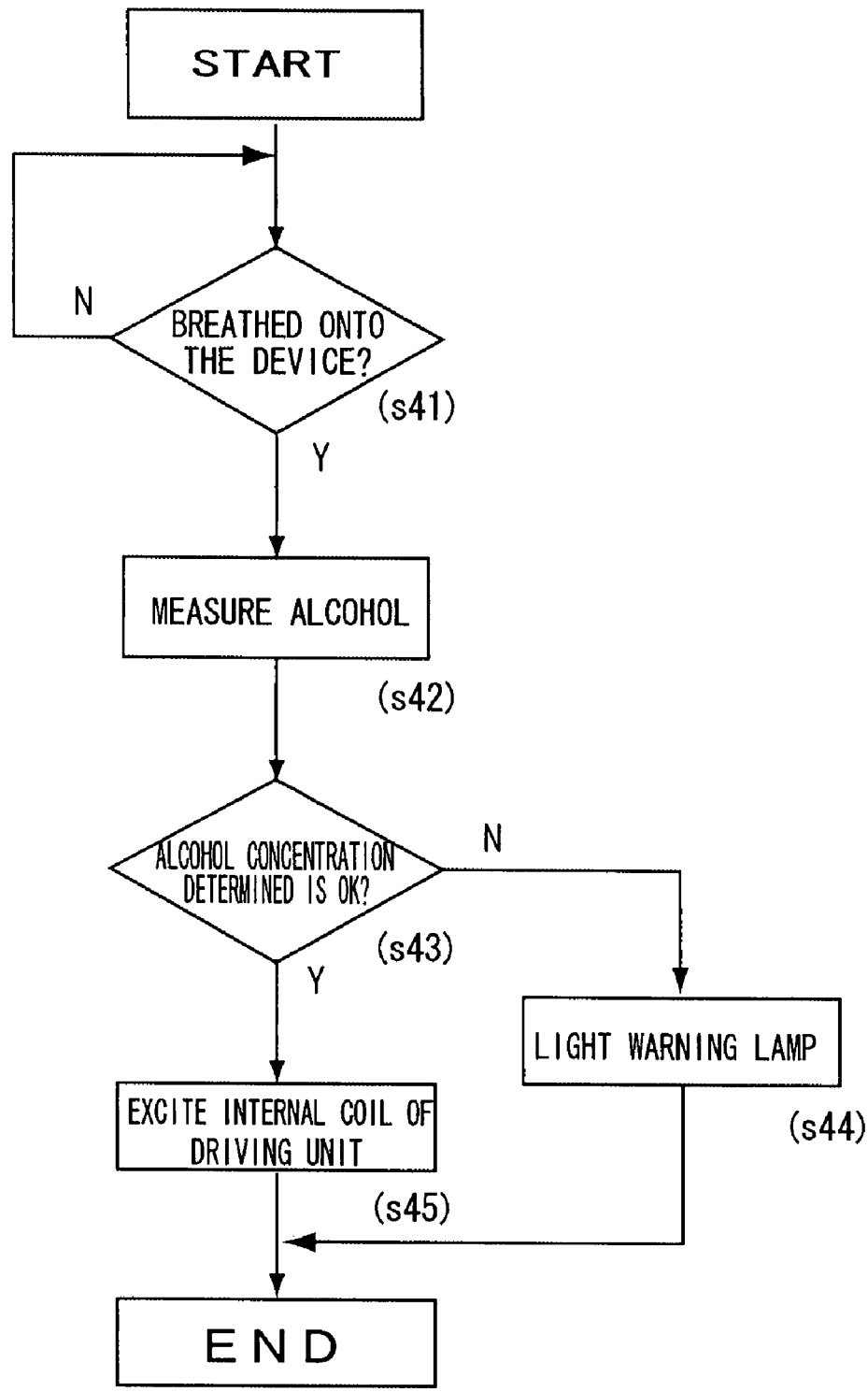
FIG. 23 shows a second alcohol concentration determining program processed by a determination unit of breath component concentration determining means of the same safe-driving promotion system.

Next, referring to the drawings, a safe-driving promotion system according to a fifth embodiment of the present invention is described. FIG. 18 is a block diagram of the safe-driving promotion system according to the fifth embodiment of the present invention. FIG. 19 is schematic views showing an internal structure in a state where a rod-like body of attachment preventing means of the same system is projected, (a) being a plane view in which an inside can be seen transparently, (b) being a vertical cross-sectional view, (c) being a traverse cross-sectional view. FIG. 20 is a schematic plane view of the rod-like body of the same attachment preventing means. FIG. 21 is schematic views showing the internal structure in a containable state of the rod-like body of the same attachment preventing means, (a) being a plane view in which an inside can be seen transparently, (b) being a vertical cross-sectional view, (c) being a traverse cross-sectional view, (d) being an enlarged view of an α portion with biasing means excluded. FIG. 22 is schematic views showing the internal structure in a contained state of the rod-like body of the same attachment preventing means, (a) being a plane view in which an inside can be seen transparently, (b) being a vertical cross-sectional view, (c) being a traverse cross-sectional view. FIG. 23 shows a second alcohol concentration determining program processed by a determination unit of breath component concentration determining means of the same safe-driving promotion system.

The safe-driving promotion system shown in FIG. 18 is different from the safe-driving promotion system of Embodiment 2 in that the breath component concentration determining means 300 is provided in the male part 11 of the seat belt, and in the configuration of the breath component concentration determining means 300 and the configuration of the attachment preventing means 400'. Hereinafter, the differences are described in detail, and the overlapping features are omitted. The same reference numerals as those of Embodiment 2 are given.

The attachment preventing means 400', as shown in FIG. 18, has a housing 401' provided integrally with the male part 11 of the seat belt, a rod-like body 410' provided in such a manner as to move into and out of this housing 401' along the tongue 11*a*, biasing means 420' interposed between the rod-like body 410' and the housing 401' for biasing the rod-like body 410' in a projecting direction, and a locking mechanism 430' for locking the rod-like body 410' in a projected state from the housing 401'.

As shown in FIGS. 19, 21 and 22, inside of the housing 401' there is provided a first container 401*a'* in the center, on one end side of the projecting direction of the rod-like body 410'. Also, inside of this housing 401' there is provided a second container 401*b'* extending perpendicularly to a tip end of the first container 401*a'*. The first container 401*a'* contains the biasing means 420' and the rod-like body 410' to guide the rod-like body 410' movably in the projecting direction. The second container 401*b'* has a height dimension that does not interfere with the rod-like body 410' so as to movably contain a locking bar 431' of the locking mechanism 430'.

As shown in FIGS. 19 and 20, the rod-like body 410' is a rectangular resin-molded component and has a recessed part 411' in one surface in a width direction. The locking bar 431' of the locking mechanism 430' is fitted into this recessed part 411' to lock the rod-like body 410' in the projected state. That is, when the locking bar 431' of the locking mechanism 430' is out of engagement with the recessed part 411', the rod-like body 410' is in a containable state.

Furthermore, a lower surface of the rod-like body 410' has a guiding groove 412', which is a long groove extending in the projecting direction, and a locking groove 413', which is a long groove also extending in the projecting direction and having a depth deeper than the guiding groove 412'. The guiding groove 412' and locking groove 413' are provided continuously as shown on the left and right in the figure. At a longitudinal end portion of the guiding groove 412', there is provided an inclined portion 412*a'*, which is inclined from the locking groove 413' to the guiding groove 412'. The guiding groove 412' and the locking groove 413' accommodate a locking spring 434' of the locking mechanism 430'.

Furthermore, opposite widthwise end portions are provided with a pair of projected parts 414'. The pair of projected parts 414' abuts against the tip end portion of the first container 401*a'* to prevent the rod-like body 410' from entering the first container 401*a'* further than a predetermined position.

The basing means 420' is a coil spring. The biasing means 420' is contained in the first container 401*a'* of the housing 401' to bias the rod-like-body 410' toward the projecting direction.

As shown in FIGS. 19, 21 and 22, the locking mechanism 430' has the locking bar 431', a driving unit 432' mounted on one end portion of the locking bar 431', a coil spring 433' mounted on the other end portion of the locking bar 431', and the locking spring 434' provided in an upper surface of the locking bar 431'.

The driving unit 432' uses a well-known magnetic latch, a movable body of which is projected from an initial position to a projected position (in the right direction in the figures) by exciting an internal coil. The movable body of the driving unit 432' is mounted on the one end portion of the locking bar 431'. That is, the movement of the movable body of the driving unit 432' allows the locking bar 431' to move in the right direction in the figures.

One end of the coil spring 433' is attached to the other end portion of the locking bar 431', while the other end thereof is attached to an inner wall surface in the direction perpendicular to the projecting direction inside the housing 401'. In such arrangement the coil spring 433' pulls the locking bar 431' to the right in the figures and to apply moving force to the locking bar 431' during movement.

The locking bar 431' is a plate-like body, with one end portion bent into a substantially L shape and the other end portion bent into a substantially Ω shape. The locking bar 431' is movably contained in the second container 401*b'* of the housing 401' and arranged under the rod-like body 410'. When the movable body of the driving unit 432' is located in the initial position, the other end portion of the locking bar 431' is fitted into the recessed part 411' of the rod-like body 410' to lock the rod-like body 410' in the projected state. On the other hand, when the movable body of the driving unit 432' is located in the projected position, the locking bar 431' is brought out of engagement (i.e., the locking is released). That is, the other end portion of the locking bar 431' forms a fitting part 431*a'* for fitting into the recessed part 411' of the rod-like body 410'.

The locking spring 434' is a plate spring, whose base end portion is attached to the center of the upper surface of the locking bar 431'. The tip end portion of the locking spring 434' is fitted into the guiding groove 412' of the rod-like body 410' when the locking bar 431' is located in a locking position (see FIG. 19(*c*)), and is fitted into the locking groove 413' of the rod-like body 410' when the locking bar 431' is located in a locking released position (see FIG. 21(d)). The tip end portion of the locking spring 434' is locked in the locking grooved 413' so as to prevent the locking bar 431' from returning to the locking position and hold the rod-like body 410' in the containable state.

Moreover, during the shift of the rod-like body 410' from the containable state (see FIG. 21(d)) to the contained state (see FIG. 22(c)), the tip end portion of the locking spring 434' is guided by the inclined portion 412a' of the guiding groove 412' of the rod-like body 410' to move from the locking groove 413' to the guiding groove 412'. This releases the holding of the rod-like-body 410' in the containable state.

The breath component concentration means 300 has the sensing means 310 and the determination unit 320. A part of functions of "the driving controller 440' of the attachment preventing means 400'" in Embodiment 2 are added to the determination unit 320, as will be described in detail later. Moreover, the driving unit 432' of the attachment preventing means 400' is connected to the output port of the determination unit 320.

That is, the determination unit 320, by processes the second alcohol concentration determining program shown in FIG. 23, which is recorded on a memory not shown, measures the alcohol concentration in breath of the driver based on the sensing data of the sensing means 310, and compares a value of the measurement result with the reference value on the memory to determine whether or not the value of the measurement result (i.e., value of the alcohol concentration in the breath of the driver) is the reference value or above. At this time, if the determination unit 320 determines that the value of the measurement result is less than the reference value, then it excites the internal coil of the driving unit 432' of the attachment preventing means 400' to project the movable body of the driving unit 432', while if the value is the reference value or above, the determination unit 320 lights a warning lamp (not shown).

The breath component concentration determining means 300, as in Embodiment 2, can be provided with the biometric means 800 for reading physical characteristics of the driver to authenticate the driver and/or the GPS transmitter 900.

Hereinafter, the usage of the safe-driving promotion system of the above-described configuration is described. Described also in detail are the contents of the second alcohol concentration determining program shown in FIG. 23 which is processed by the determination unit 320 of the breath component concentration determining means 300. Also, the operations of the respective units and parts are described.

First, when the seat belt of the automobile 1 has not been fastened, as shown in FIG. 19, the fitting part 431a' of the locking bar 431' of the locking mechanism 430' is fitted into the recessed part 411' of the rod-like body 410', so that the rod-like body 410' is locked in the projected state. At this time, the locking spring 434' of the locking mechanism 430' is fitted into the guiding groove 412' of the rod-like body 410'.

In starting the motor 20 of the automobile 1, the driver turns on the breath component concentration determining means 300. In response to this, the determination unit 320 of the breath component concentration determining means 300 processes the second alcohol concentration determining program as shown in FIG. 23.

Then, the determination unit 320 determines whether or not sensing data of the sensing means 310 has been inputted (i.e., whether or not the sensing means 310 has been breathed on) (s41). As a result, if it is determined that the breathing has not been performed, the processing returns to step 41. On the other hand, if it is determined that the sensing data has been inputted and that the breathing has been performed, the determination unit 320 measures the alcohol concentration contained in the breath of the driver based on the sensing data of the sensing means 310 (s42). It is determined whether or not a value of the measurement result (i.e., value of the alcohol concentration in the breath of the driver) is the reference value on the memory or above (s43). As a result, if it is determined that the value is the reference value or above, the determination unit 320 lights the warning lamp (s44) and finishes the processing of the second alcohol concentration determining. On the other hand, if it is determined that the value of the measurement result is less than the reference value, the determination unit 320 excites the internal coil of the driving unit 432' of the attachment preventing means 400' for a predetermined time (s45), and finishes the processing of the second alcohol concentration determining program.

When the internal coil of the driving unit 432' of the attachment preventing means 400' is excited, the movable body of the driving unit 432' moves from the initial position to the projected position, as shown in FIG. 21. The movement causes the locking bar 431' of the locking mechanism 430' to move in the right direction in the figure. At this time, the coil spring 433' of the locking mechanism 430' gives the moving force to the movement of the movable body and the locking bar 431'.

Once the movable body of the driving unit 432' and the locking bar 431' of the locking mechanism 430' move, the fitting part 431a' of the locking bar 431' is brought out of engagement with the recessed part 411' of the rod-like body 410' (i.e., the locking is released). Then, when the excitation of the internal coil of the driving unit 432' is stopped, the movable body returns from the projected position to the initial position. At this time, the tip end portion of the locking spring 434' of the locking mechanism 430' is fitted into the locking groove 413' of the rod-like body 410' to be locked. The locking bar 431' is thus held in the state where the fitting part 431a' thereof is not fitted into the recessed part 411' of the rod-like body 410'. That is, the rod-like body 410' is held in the containable state in the housing 401'. In the meantime, the movable body of the driving unit 432' is at rest in the process of returning to the initial position since the locking bar 431' is held as described above.

Thereafter, when the driver attaches the male part 11 to the female part 12, as shown in FIG. 22, the rod-like body 410' abuts against the female part 12 and is contained in the housing 401' against the biasing force of the biasing means 420' In this process, the tip end portion of the locking spring 434' of the locking mechanism 430' is guided by the inclined portion 412a' of the guiding groove 412' of the rod-like body 410' to move from the locking groove 413' to the guiding groove 412'. This releases the holding of the rod-like body 410' in the containable state.

Once the male part 11 is attached to the female part 12, the first start permission signal α is outputted from the attachment sensing means 100 to the start controlling means 200. When the first start permission signal α is inputted, the body controller 210 of the start controlling means 200 puts the motor 20 into the startable state. This allows the driver to start the motor 20.

Thereafter, when the driver detaches the male part 11 from the female part 12, the rod-like body 410' is projected from the housing 401' along the tongue 11a of the male part 11 by the biasing force of the biasing means 420'. In response to this, by the recovery force to the initial position of the movable body of the driving unit 432', the locking bar 431' moves in the left direction in the figure, so that the fitting part 431a' is fitted into the recessed part 411' of the rod-like body 410'. The rod-like body 410' is thereby locked in the projected state again.

In the above-described safe-driving promotion system, if the determination unit 320 of the breath component concentration determining means 300 determines that the breath of the driver contains alcohol of the reference value or above, then the determination unit 320 does not excite the internal coil of the driving unit 432' of the attachment preventing means 400'. Therefore, the rod-like body 410' of the attachment preventing means 400' remains projected along the tongue 11a, which disables the male part 11 of the seat belt to be inserted into the female part 12. Thus, when the seat belt cannot be attached, the first start permission signal α is not outputted from the attachment sensing means 100 provided in the male part 11, and the start controlling means 200 does not put the motor 20 of the automobile 1 into the startable state, so that the driver cannot start the motor 20. Thus, the drunk driving of the driver can be effectively prevented.

On the other hand, if the determination unit 320 of the breath component concentration determining means 300 determines that the breath of the driver contains the alcohol below the reference value, the internal coil of the driving unit 432' of the locking mechanism 430' is excited, so that the locking in the projected state of the rod-like body 410' by the locking mechanism 430' is released. This enables the male part 11 to be inserted into the female part 12. Then, if the male part 11 of the seat belt is not attached to the female part 12, the first start permission signal α is not outputted from the attachment sensing means 100 provided in the male part 11. Since the configuration is such that the body controller 210 of the start controlling means 200 puts the motor 20 of the automobile 1 into the startable state only when the first start permission signal α is inputted, the driver can be forced to fasten the seat belt.

Additionally, since the determination unit 320 of the breath component concentration determining means 300 functions as the driving controller 440' of the attachment preventing means 400', the number of parts can be reduced, thereby achieving cost reduction.

EMBODIMENT 6

Figure 24:
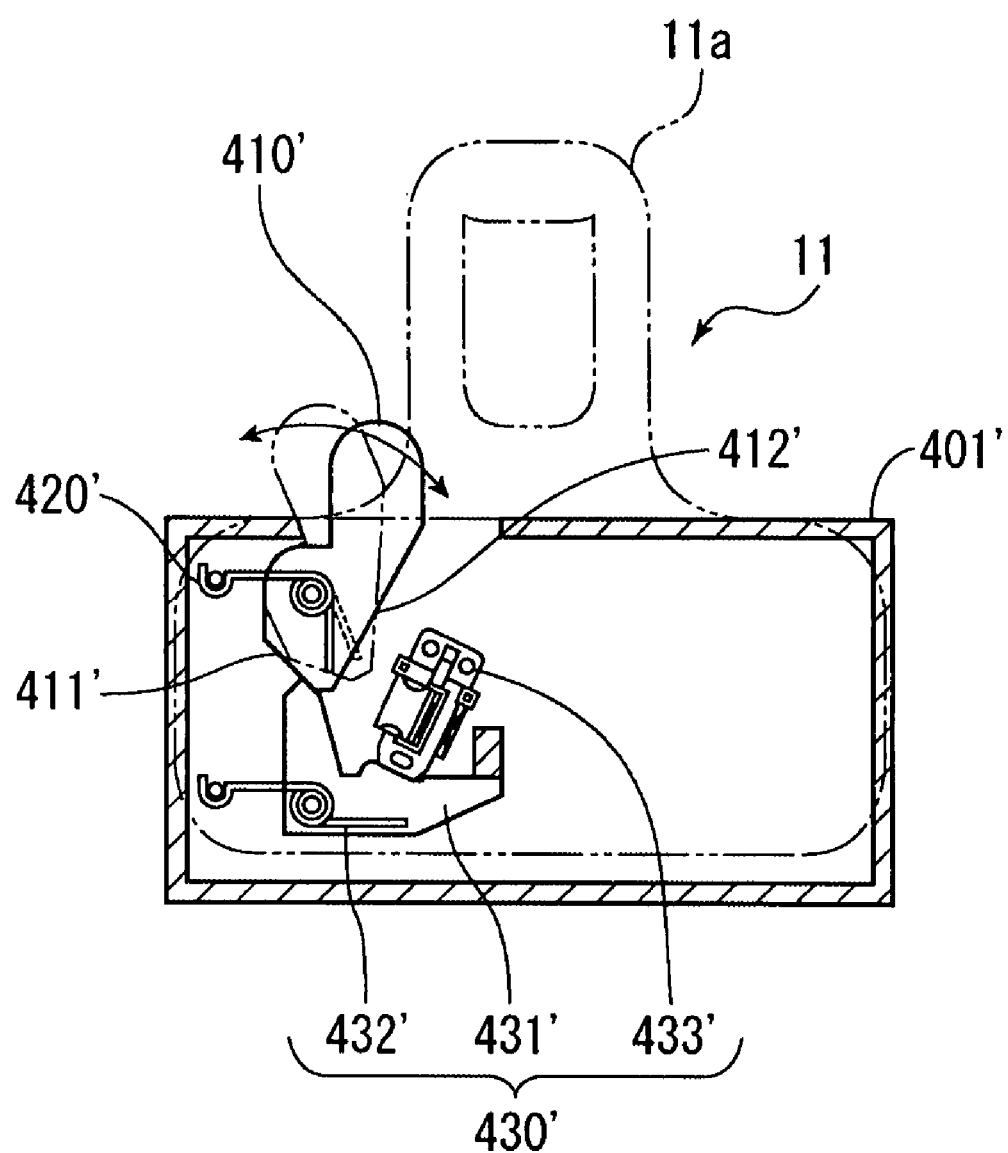
FIG. 24 is a schematic plane view in which an inside can be seen transparently, showing a state where a rod-like body of attachment preventing means of a safe-driving promotion system according to a sixth embodiment of the present invention is projected.
Figure 25:
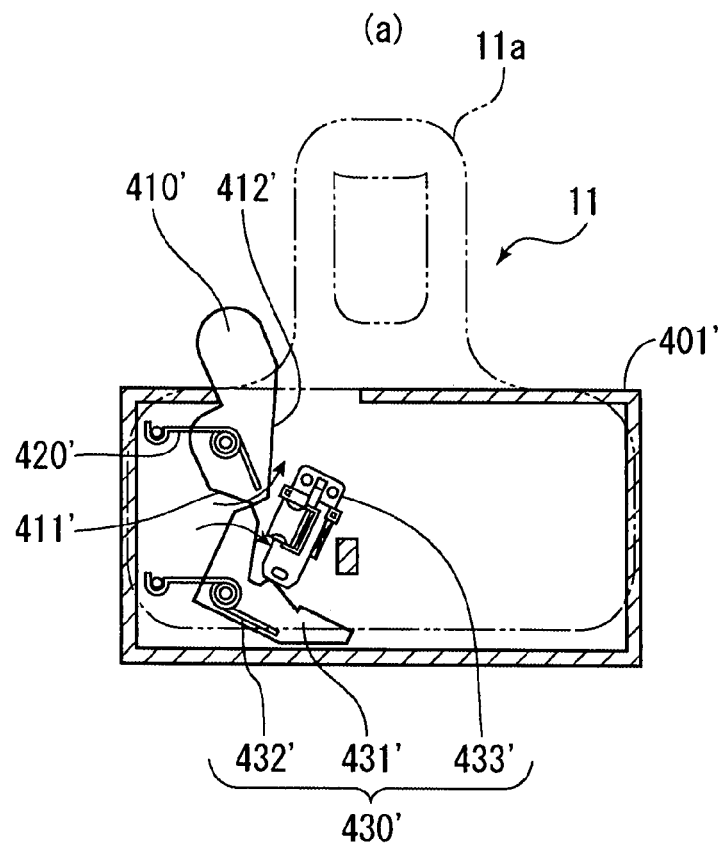
FIG. 25 is schematic plane views of the same attachment preventing means in which an inside can be seen transparently, (a) being a view showing the attachment preventing means during operation of a locking mechanism, (b) being a view showing the attachment preventing means when the locking mechanism operation is finished.
Figure 25:
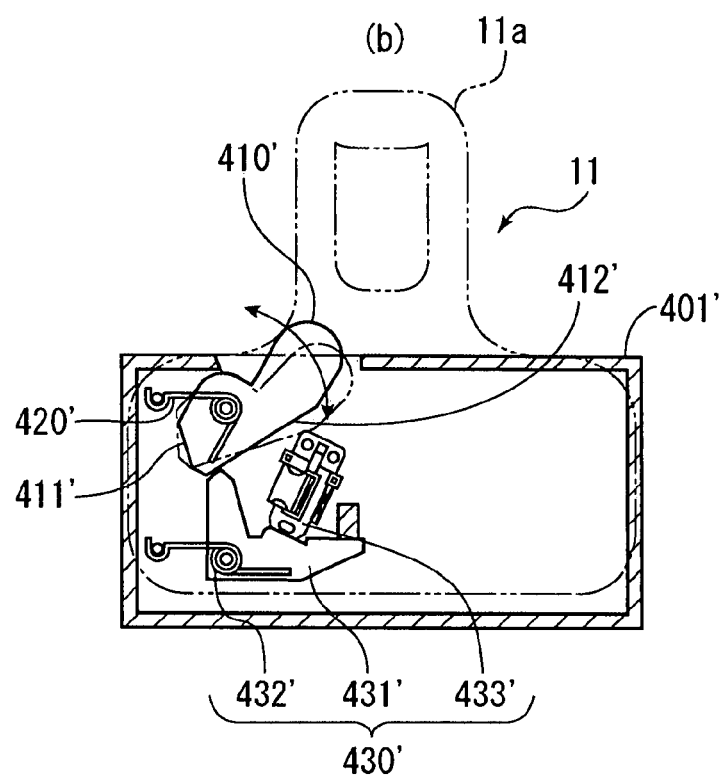
Figure 26:
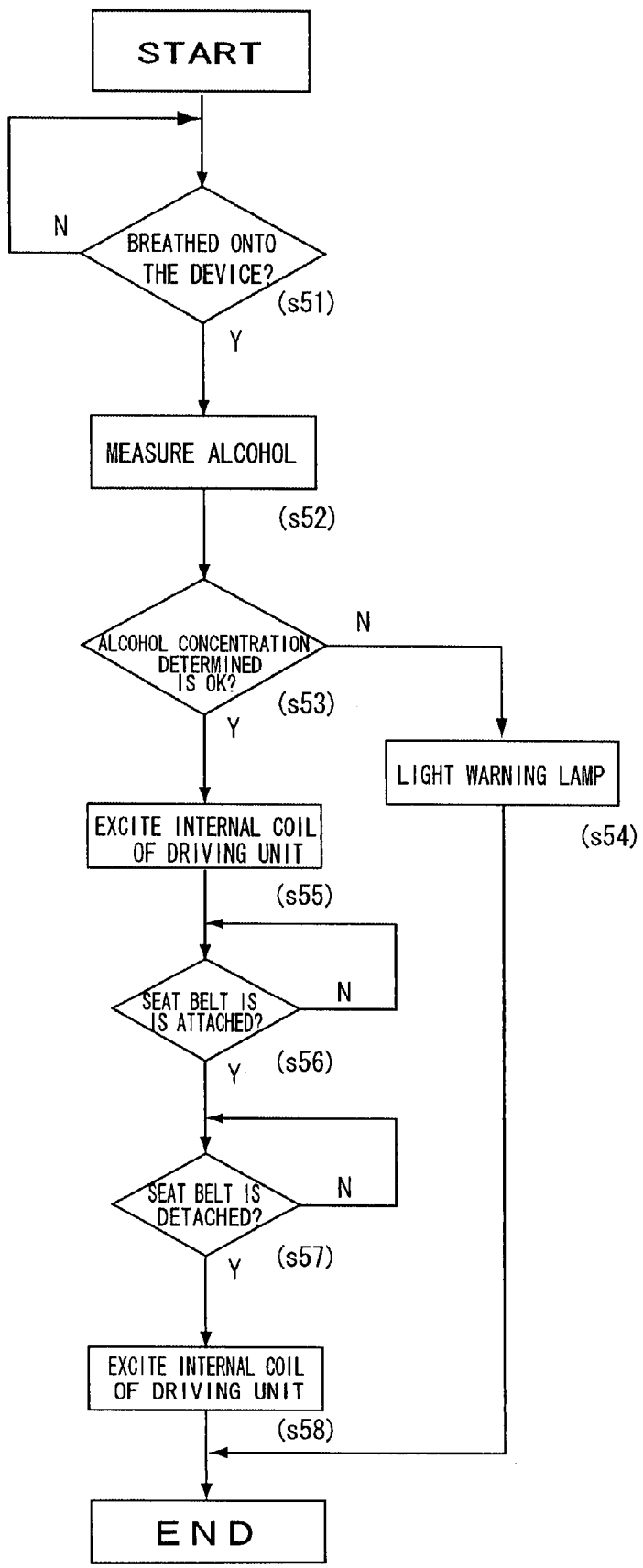
FIG. 26 is a flowchart of a third alcohol concentration determining program processed by a determination unit of breath component concentration determining means of the same system.

Next, referring to the drawings, a safe-driving promotion system according to a sixth embodiment of the present invention is described. FIG. 24 is a schematic plane view in which an inside can be seen transparently, showing a state where a rod-like body of attachment preventing means of the safe-driving promotion system according to the sixth embodiment of the present invention is projected. FIG. 25 is schematic plane views of the same attachment preventing means in which an inside can be seen transparently, (a) being a view showing the attachment preventing means during operation of a locking mechanism, (b) being a view showing the attachment preventing means when the locking mechanism operation is finished. FIG. 26 is a flowchart of a third alcohol concentration determining program which is processed by a determination unit of breath component concentration determining means of the same system.

The safe-driving promotion system described here is different from the safe-driving promotion system of Embodiment 5 in the configuration of the attachment preventing means 400'. Hereinafter, the different points are described in detail, and overlapping descriptions are omitted. The same reference numerals as those of Embodiment 5 are given.

The attachment preventing means 400', as shown in FIG. 24, has a housing 401' provided integrally with the male part 11 of the seat belt, a rod-like body 410' provided rotatably in the housing 401' in such a manner as to move in and out along the tongue 11a, biasing means 420' for biasing the rod-like body 410', and a locking mechanism 430' for locking the rod-like body 410' in a projected state.

In the rod-like body 410', a base end portion thereof is pivotably and rotatably supported by the housing 401', while a tip end portion thereof moves from a projected position where it is projected along the tongue 11a from the housing 401' to a contained position where it is contained in the housing 401'. In the base end portion of the rod-like body 410', both widthwise side surfaces are cut to make up first and second abutting surfaces 411', 412' against which the locking bar 431' of the locking mechanism 430' abuts.

The biasing means 420' is a torsion coil spring whose coil part is mounted on a rotating shaft of the rod-like body 410. One end portion of the biasing means 420' is attached to the housing 401', while the other end portion is attached to the base end portion of the rod-like body 410'. The biasing means 420' is compressed in a state where the tip end portion of the rod-like body 410' is located in the projected position, and biases the rod-like body 410' in a right rotation direction in the figure (i.e., the direction in which the tip end portion of the rod-like body 410' is contained in the housing 401'). On the other hand, in a state where the tip end portion of the rod-like body 410' is located in the contained position, the biasing means 420' is compressed and biases the rod-like body 410' in a left rotation direction in the figure (i.e., the direction where the tip end portion of the rod-like body 410' is projected from the housing 401').

The locking mechanism 430' has a substantially L-shaped locking bar 431', whose central portion is supported pivotably and rotatably by the housing 401', and whose one end portion abuts the first abutting surface 411' or the second abutting surface 412' of the rod-like body 410', a torsion coil spring 432' that biases the locking bar 431' in the right rotation direction in the figure, and a driving unit 433' that presses the locking bar 431'.

The locking bar 431', by abutting the one end portion thereof against the first abutting surface 411' of the rod-like body 410' as shown in FIG. 24, holds the rod-like body 410' in the state of being located in the projected position. On the other hand, as shown in FIG. 25(b), it holds the rod-like body 410' in the containable state by abutting the one end portion thereof against the second abutting surface 412' of the rod-like body 410'. The locking bar 431' is prevented from rotating beyond a predetermined position by abutting the other end thereof against a stop portion provided in the housing 401'.

The driving unit 433' is a well-known solenoid in which a movable body is moved from the initial position to the projected position by the excitation of an internal coil. The movable body of the driving unit 433' presses the locking bar 431', particularly the inner side of the other end portion for abutting the above mentioned stop portion. The pressing causes the locking bar 431' to rotate the right rotation direction in the figure.

The torsion coil spring 432' has a coil part mounted on a rotating shaft of the locking bar 431'. One end portion of the torsion coil spring 432' is attached to the housing body 401' and the other end portion is attached to the base end portion of the locking bar 431'. This torsion coil spring 432' is compressed by the locking bar 431' being pressed by the movable body of the driving unit 433'.

The breath component concentration determining means 300 is different from that of Embodiment 5 in that the attachment sensing means 100 is connected to the input port of the determination unit 320 and in the contents of the alcohol concentration determining program processed by the determination unit 320, but the others are the same.

Hereinafter, the usage of the safe-driving promotion system of the above-described configuration is described. Described also in detail are the contents of the third alcohol concentration determining program shown in FIG. 26 which is processed by the determination unit 320 of the breath component concentration determining means 300. Also, the operations of the respective units and parts are described.

First, when the seat belt of the automobile 1 has not been fastened, as shown in FIG. 24, the one end portion of the locking bar 431' of the locking mechanism 430' abuts the first abutting surface 411' of the rod-like body 410', so that the tip end portion of the rod-like body 410' is locked in the state of being located in the projected position.

In starting the motor 20 of the automobile 1, the driver turns on the breath component concentration determining means 300. In response to this, the determination unit 320 of the breath component concentration determining means 300 processes the third alcohol concentration determining program as shown in FIG. 26.

Then, the determination unit 320 determines whether or not sensing data of the sensing means 310 has been inputted (i.e., whether or not the sensing means 310 has been breathed on) (s51). As a result, if it is determined that the breathing has not been performed, the processing returns to step 51. On the other hand, if it is determined that the sensing data has been inputted and that the breathing has been performed, the determination unit 320 measures the alcohol concentration contained in the breath of the driver based on the sensing data of the sensing means 310 (s52). It is determined whether or not a value of the measurement result (i.e., value of the alcohol concentration in the breath of the driver) is the reference value on the memory or above (s53). As a result, if it is determined that the value is the reference value or above, the determination unit 320 lights the warning lamp (s54) finishes the processing of the third alcohol concentration determining program. On the other hand, if it is determined that the value of the measurement result is less than the reference value, the determination unit 320 excites the internal coil of the driving unit 433' of the attachment preventing means 400' for a predetermined time (s55).

When the internal coil of the driving unit 433' of the attachment preventing means 400' is excited, the movable body of the driving unit 433' moves from the initial position to the projecting position to press and rotate the locking bar 431' in the right rotation direction in the figure, as shown in FIG. 25(a). At this time, the torsion coil spring 432' is compressed. In response to this, the one end portion of the locking bar 431' presses the first abutting surface 411' of the rod-like body 410'. This causes the rod-like body 410' to rotate in the left rotation direction in the figure. Then, when the one end portion of the locking bar 431' is brought out of abutment against the first abutting surface 411' of the rod-like body 410', the rod-like-body 410' is rotated in the right rotation direction in the figure by the biasing force of the biasing means 420'.

During the rotation of the rod-like body 410', the excitation of the internal coil of the driving unit 433' of the attachment preventing means 400' is stopped, and as shown in FIG. 25(b), the movable body of the driving unit 433' returns to the initial position from the projected position. In response to this, the locking bar 431' rotates in the left rotation direction in the figure by the biasing force of the torsion coil spring 432'. The other end portion of the locking bar 431' abuts the stop portion of the housing 401', while the one end portion of the locking bar 431' abuts the second abutting surface 412' of the rod-like body 410'. This allows the rod-like body 410' to be held in the housing 401' in the containable state. That is, the locking mechanism 430' releases the locking of the rod-like body 410'.

Thereafter, when the driver attaches the male part 11 to the female part 12, the rod-like body 410' abuts the female part 12, and is contained in the housing 401' against the biasing force of the biasing means 420'. At this time, the biasing means 420' is compressed.

Once the male part 11 is attached to the female part 12, the first start permission signal α is outputted from the attachment sensing means 100 to the start controlling means 200 and the determination unit 320 of the breath component concentration determining means 300. When the first start permission signal α is inputted, the body controller 210 of the start controlling means 200 puts the motor 20 into the startable state. This allows the driver to start the motor 20.

After step s55, if the determination unit 320 determines that the first start permission signal a of the attachment sensing means 100 has been inputted, and that the male part 11 has been attached to the female part 12 (s56). Then, the determination unit 320 determines whether or not the male part 11 has been detached from the female part 12 based on the output signal of the attachment sensing means 100. That is, it is determined whether or not the drive has detached the male part 11 from the female part 12 (s57). As a result, if it is determined that the male part 11 have not been detached from and the female part 12, the processing of step 57 is repeated. On the other hand, if it is determined that the male part 11 and the female part 12 have been detached, the determination unit 320 excites the internal coil of the driving unit 433' of the attachment preventing means 400' for the predetermined time (s58). Thereafter, the determination unit 320 finishes the processing of the third alcohol concentration determining program.

When the internal coil of the driving unit 433' of the attachment preventing means 400' is excited, the movable body of the driving unit 433' moves from the initial position to the projected position to press and rotate the locking bar 431' in the right rotation direction in the figure. At this time, the torsion coil spring 432' is compressed. In response to this, the one end portion of the locking bar 431' is brought out of abutment against the second abutting surface 412' of the rod-like body 410', and the rod-like-body 410' is rotated in the left rotation direction in the figure by the biasing force of the biasing means 420'.

During the rotation of this rod-like body 410', when the excitation of the internal coil of the driving unit 433' of the attachment preventing means 400' is stopped, the locking bar 431' is rotated in the left rotation direction in the figure by the biasing force of the torsion coil spring 432'. While the other end portion of the locking bar 431' abuts the stop portion of the housing 401', the one end portion of the locking bar 431' abuts the first abutting surface 411' of the rod-like body 410'. This causes the rod-like body 410' to be again locked in the state where the tip end portion thereof is located in the projected position.

In the above-described safe-driving promotion system, if the determination unit 320 of the breath component concentration determining means 300 determines that the breath of the driver contains alcohol of the reference value or above then the determination unit 320 does not excites the internal coil of the driving unit 433' of the attachment preventing means 400'. Therefore, the rod-like body 410' of the attachment preventing means 400' remains projected along the tongue 11a which disables the male part 11 of the seat belt to be inserted into the female part 12. Thus, when the seat belt cannot be fastened, the first start permission signal α is not outputted from the attachment sensing means 100 provided in the male part 11, and the start controlling means 200 does not put the motor 20 of the automobile 1 into the startable state, so that the driver cannot start the motor 20. Thus, the drunk driving of the driver can be effectively prevented.

On the other hand, if the determination unit 320 of the breath component concentration determining means 300 determines that the breath of the driver contains the alcohol below the reference value, the internal coil of the driving unit 433' of the locking mechanism 430' is excited, so that the locking mechanism 430' releases the locking of the rod-like body 410'. This enables the rod-like body 410' to be contained in the housing 401', so that the male part 11 can be inserted into the female part 12. Then, if the male part 11 of the seat belt is not attached to the female part 12, the first start permission signal α is not outputted from the attachment sensing means 100 provided in the male part 11. Since the configuration is such that the body controller 210 of the start controlling means 200 does puts the motor 20 of the automobile 1 into the startable state only when the first start permission signal α not inputted, the driver can be forced to wear the seat belt.

Further, since the determination unit 320 of the breath component concentration determining means 300 functions as the driving controller 440' of the attachment preventing means 400', the number of parts can be reduced, thereby achieving cost reduction.

EMBODIMENT 7

Figure 27:
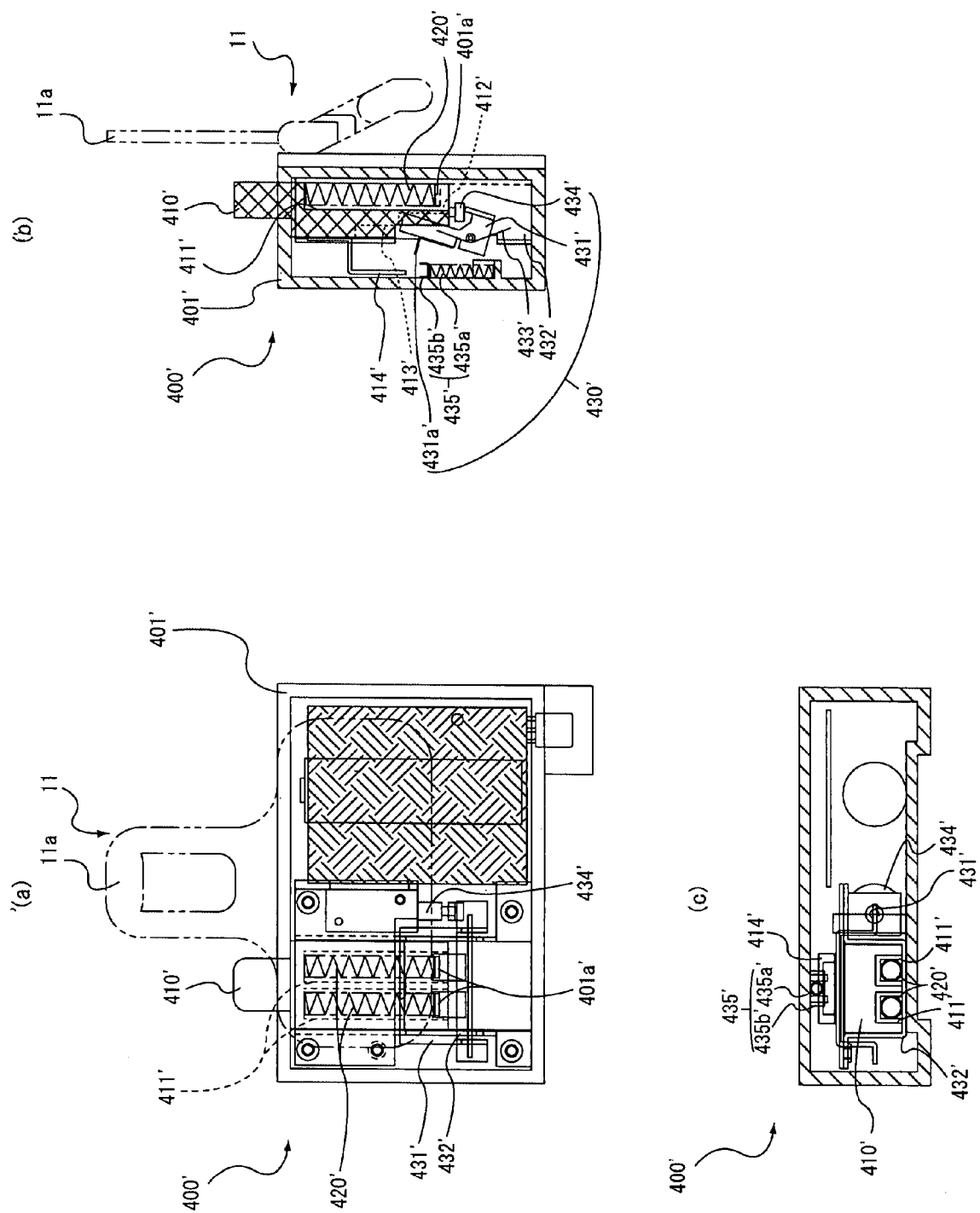
FIG. 27 is schematic views showing an internal structure of attachment preventing means of a safe-driving promotion system according to a seventh embodiment of the present invention, (a) being a bottom view in which an inside can be seen transparently, (b) being a vertical cross-sectional view, (c) being a traverse cross-sectional view.
Figure 28:
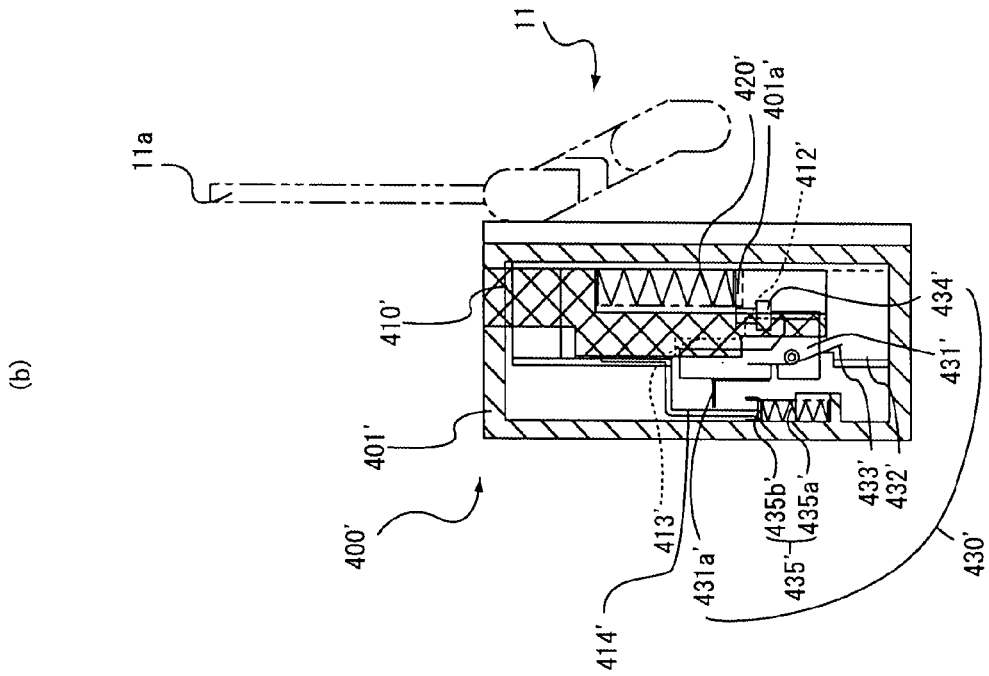
FIG. 28 is schematic views showing the internal structure of the same attachment preventing means, (a) being a vertical cross-sectional view showing a containable state of a rod-like body, (b) being a vertical cross-sectional view showing a contained state of the rod-like body.
Figure 28:
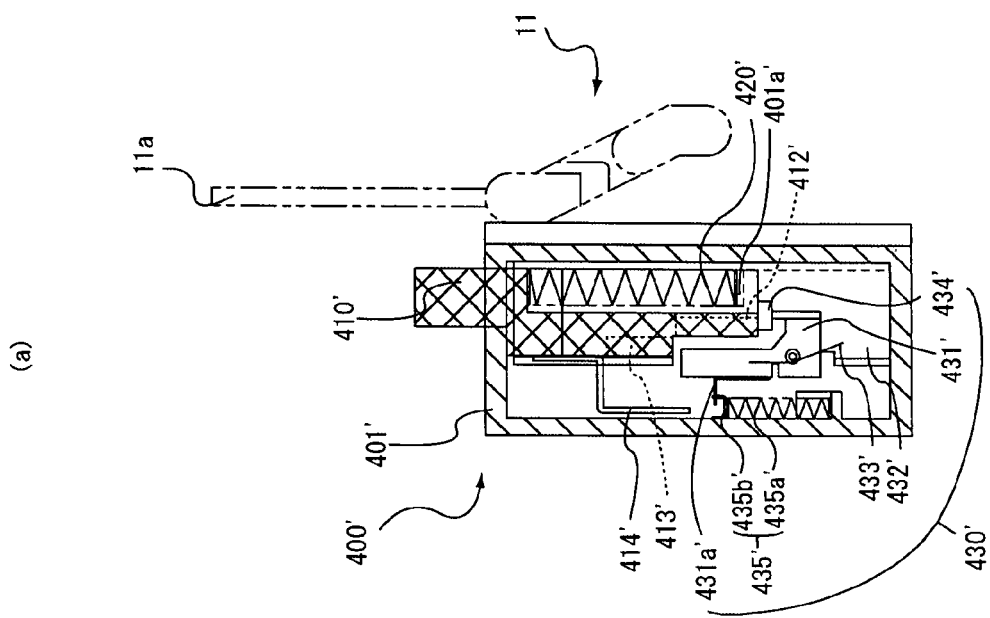
Figure 29:
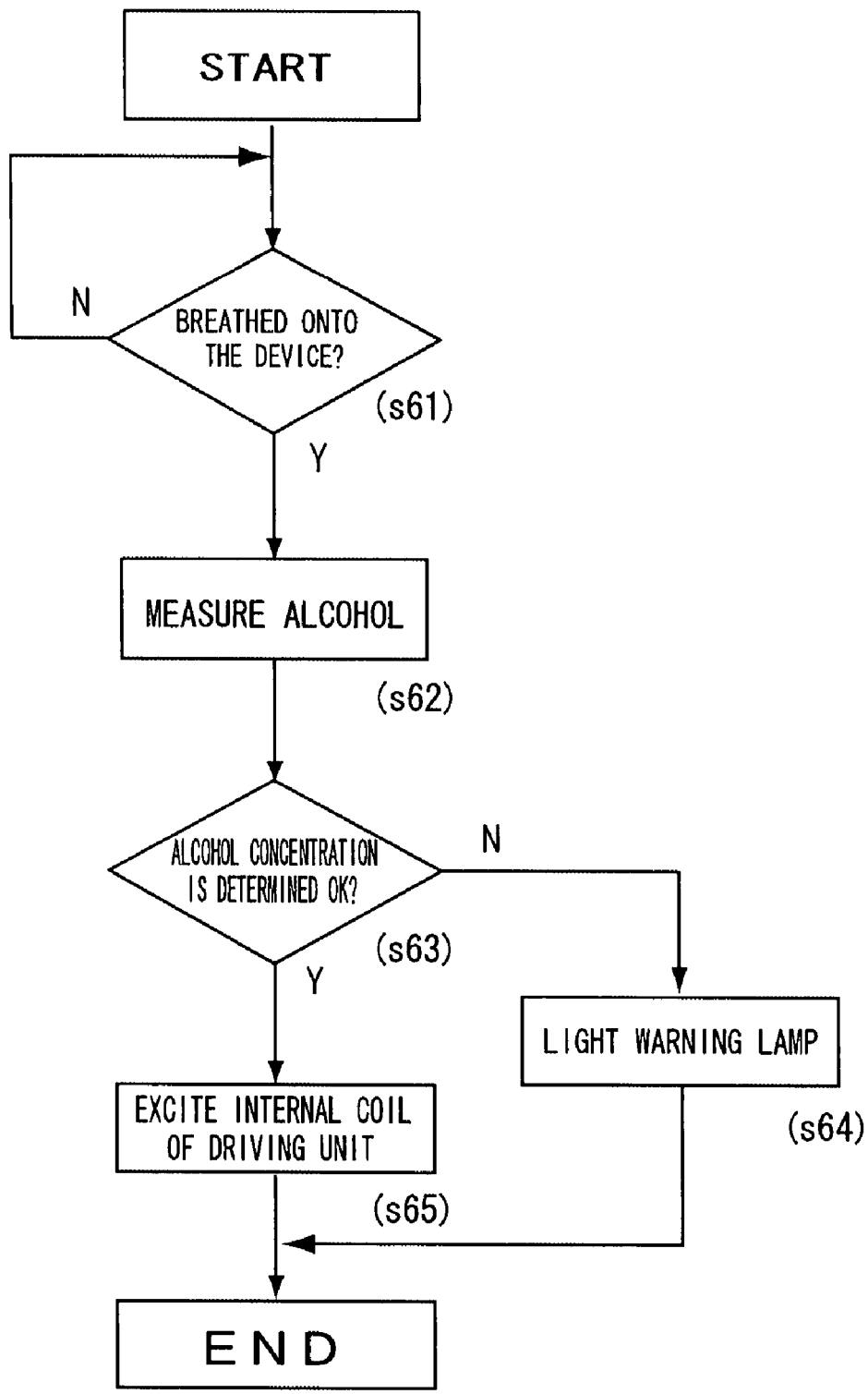
FIG. 29 is a flowchart of a fourth alcohol concentration determining program processed by a determination unit of breath component concentration determining means of the same system.

Next, referring to the drawings, a safe-driving promotion system according to a seventh embodiment of the present invention is described. FIG. 27 is schematic views showing an internal structure of attachment preventing means of the safe-driving promotion system according to the seventh embodiment of the present invention, (a) being a bottom view in which an inside can be seen transparently, (b) being a vertical cross-sectional view, (c) being a traverse cross-sectional view. FIG. 28 is schematic views showing the internal structure of the same attachment preventing means, (a) being a vertical cross-sectional view showing a containable state of a rod-like body, (b) being a vertical cross-sectional view showing a contained state of the rod-like body. FIG. 29 is a flowchart of a fourth alcohol concentration determining program processed by a determination unit of breath component concentration determining means of the same system.

The safe-driving promotion system described here is different from the safe-driving promotion system of Embodiment 5 in the configuration of the attachment preventing means 400'. Hereinafter, the different points are described in detail, and the overlapping descriptions are omitted. The same reference numerals as those of Embodiment 5 are given.

The attachment preventing means 400', as shown in FIG. 27, has a housing 401' provided integrally with the male part 11 of the seat belt, a rod-like body 410' provided in such a manner as to move into and out of the housing 401' along the tongue 11a, a pair of biasing means 420' for biasing this rod-like body 410', and a locking mechanism 430' for locking the rod-like body 410' in a projected state.

As shown in FIG. 27, the rod-like body 410' is a rectangular resin-molded component. Its lower surface is provided with a pair of long recesses 411' oriented in the projecting direction of the rod-like body 410'. The pair of recesses 411' accommodates the pair of biasing means 420' and a pair of projected parts 401a' of the housing 401'.

Moreover, an upper surface of the rod-like body 410' is cut away toward the rear end in the projecting direction of the rod-like body 410', as shown in FIG. 27(b). This cutaway portion is provided with a recessed groove 412' for engagement with the locking bar 431' of the locking mechanism 430'. Also, a front portion of the cutaway portion of the upper surface of the rod-like body 410' is provided with a groove part 413' for avoiding the interference with the locking bar 431' of the locking mechanism 430' in a state where the rod-like body 410' is contained in the housing 401' (hereinafter, the contained state). Furthermore, forward of the groove part 413' in the upper surface of the rod-like body 410', there is provided a piece member 414' for releasing the holding of the locking bar 431' of the locking mechanism 430' and a holding mechanism 435'.

The bottom surface of the housing 401' is provided with a pair of projected parts 401a' to be contained in the pair of recessed parts 411' of the rod-like body 410'.

The biasing means 420' are coil springs, interposed between an inner wall surface in the projecting direction of the recesses 411' of the rod-like body 410' and the projected parts 401a'. The interposed biasing means 420' urge the rod-like body 410' in the projecting direction.

The locking mechanism 430' has a locking bar 431' for locking the rod-like body 410' in the projected state, a supporting plate 432' that is mounted on the housing 401' and supports the locking bar 431' rotatably from a locked position to a locking released position, a torsion coil spring 433' for biasing the locking bar 431', a driving unit 434' for holding the locking bar 431' in the locked position, and the holding mechanism 435' for holding the locking bar 431' in the locking released position.

The locking bar 431', as shown in FIG. 27(a), is a substantially Ω-shaped member in plane view, whose central portion is pivotably supported by the supporting plate 432'. The tip end portion of this locking bar 431' is locked in the recessed groove 412' of the rod-like body 410' when the rod-like body 410' is in the projected state as shown in FIG. 27(b), while the same tip end is contained in the groove part 413' of the rod-like body 410' when the rod-like body 410' is in the contained state as shown in FIG. 28(b). Moreover, one of base end portions of the locking bar 431' is a portion which a movable body of the driving unit 434' abuts. Moreover, on an upper surface of the locking bar 431', there is provided a locking piece 431a' to be held by the holding mechanism 435', as shown in FIG. 27(b). The locking bar 431' may be located at the locked position where the tip end portion of the locking bar 431' is locked in the recessed groove 412' of the rod-like body 410'; a locking standby position where the tip end portion of the locking bar 431' is contained in the groove part 413' of the rod-like body 410' is; and the locking released position where the locking piece 431a' of the locking bar 431' is held by the holding mechanism 435'.

The torsion coil spring 433' has a coil part mounted on a rotating shaft of the locking bar 431'. The one end portion of the spring 433' is attached to the supporting plate 432', while the other end portion is attached to the tip end portion of the locking bar 431'. The torsion coil spring 433' is compressed in a state where the locking bar 431' is located in the locked position, and biases the tip end portion of the locking bar 431' upward (i.e., in the direction of the locking released position), while the locking bar 431' is compressed in the state where the locking bar 431' is located in the locking standby position and the locking released position, and biases the tip end portion of the locking bar 431' downward (i.e., in the direction of the locked position).

The driving unit 434' is a well-known solenoid in which by the excitation of an internal coil, the movable body is moved from a projected position to a retracted position. The driving unit 434' abuts the base end portion of the locking bar 431' in the state where the movable body is located in the projected position to hold the locking bar 431' in the locked position against the biasing force of the torsion coil spring 433'.

The holding mechanism 435' has a coil spring 435a' mounted on an upper surface of the housing 401', and a hook 435b' mounted on a tip end portion of the coil spring 435a'. This hook 435b' locks the locking piece 431a' of the locking bar 431' to hold the locking bar 431' in the locking released position. Moreover, the hook 435b' is pressed by the piece member 414' of the rod-like body 410' when the rod-like body 410' is in the contained state. The coil spring 435a' is thereby compressed to release the locking between the hook 435b' and the locking piece 431a'.

The breath component concentration determining means 300 is the same as in that of Embodiment 5 in the configuration, but the contents of the alcohol concentration determining program that the determination unit 320 processes are slightly different.

Hereinafter, the usage of the safe-driving promotion system of the above-described configuration is described, and the contents of the fourth alcohol concentration determining program shown in FIG. 29 which is processed by the determination unit 320 of the breath component concentration determining means 300 are described in detail. Also, the operations of the respective units and parts are described.

First, when the seat belt of the automobile 1 has not been fastened, as shown in FIG. 27, the movable body of the driving unit 434' of the locking mechanism 430' is located in the projected position to abut the base end portion of the locking bar 431' to hold the locking bar 431' in the locked position against the biasing force of the torsion coil spring 433'.

In starting the motor 20 of the automobile 1, the driver turns on the breath component concentration determining means 300. In response to this, the determination unit 320 of the breath component concentration determining means 300 processes the fourth alcohol concentration determining program as shown in FIG. 29.

Thereafter, the determination unit 320 determines whether or not sensing data of the sensing means 310 has been inputted (i.e., whether or not the sensing means 310 has been breathed on) (s61). As a result, if it is determined that the breathing has not been performed, the processing returns to step 61. On the other hand, if it is determined that the sensing data has been inputted and that the breathing has been performed, the alcohol concentration contained in the breath of the driver is measured based on the sensing data of the sensing means 310 (s62). It is determined whether or not a value of the measurement result (i.e., a value of the alcohol concentration in the breath of the driver) is the reference value on a memory or above (s63). As a result, if it is determined that the value is the reference value or above, the determination unit 320 lights the warning lamp (s64) and finishes the processing of the fourth alcohol concentration determining program. On the other hand, if it is determined that the value of the measurement result is less than the reference value, the internal coil of the driving unit 434' of the attachment preventing means 400' is excited for a predetermined time (s65). Thereafter, the processing of the fourth alcohol concentration determining program is finished.

If the internal coil of the driving unit 434' of the attachment preventing means 400' is excited, the movable body of the driving unit 434' moves from the projected position to the retracted position, as shown in FIG. 28(*a*). In response to this, the locking bar 431' is rotated in the left rotation direction in the figure by the biasing force of the torsion coil spring 433', so that the tip end portion of the locking bar 431' moves from the locked position to the locking released position. At this time, the torsion coil spring 433' is compressed. In response to this, the locking piece 431a' of the locking bar 431' is locked in the hook 435b' of the holding mechanism 435'. This releases the locking of the rod-like body 410' by the locking mechanism 430' to put the rod-like body 410' into the containable state in the housing 401'. Then, when the excitation of the internal coil of the driving unit 434' of the attachment preventing means 400' is stopped, the movable body of the driving unit 434' returns to the projected position from the retracted position, but the locking bar 431' is held by the holding mechanism 435' in the state where it is located in the locking released position.

Thereafter, when the driver attaches the male part 11 to the female part 12, as shown in FIG. 28(*b*), the rod-like body 410' abuts the female part 12 to be contained in the housing 401' against biasing force of the pair of the biasing means 420'. At this time, the pair of the biasing means 420' is compressed. In response to this, the hook 435b' is pressed by the piece member 414' of the rod-like body 410'. The coil spring 435a' is thereby compressed to release the locking between the hook 435b' and the locking piece 431a' of the locking bar 431'. In response to this, the locking bar 431' is rotated in the right rotation direction by the biasing force of the torsion coil spring 433' to move the tip end portion of the locking bar 431' from the locking released position to the locking standby position.

Once the male part 11 is attached to the female part 12, the first start permission signal α is outputted from the attachment sensing means 100 to the start controlling means 200. When the first start permission signal α is inputted, the body controller 210 of the start controlling means 200 puts the motor 20 into the startable state, allowing the driver to start the motor 20.

Thereafter, when the driver detaches the male part 11 from the female part 12, the rod-like body 410' is projected from the housing 401' along the tongue 11a of the male part 11 by the biasing force of the pair of biasing means 420'. In response to this, the biasing force of the torsion coil spring 433' rotates, the locking bar 431' in the right rotation direction in the figure, so that the tip end portion of the locking bar 431' moves from the locking standby position to the locked position. The rod-like body 410' is thereby locked again in the projected state.

In the case of the above-described safe-driving promotion system, if the determination unit 320 of the breath component concentration determining means 300 determines that the breath of the driver contains alcohol of the reference value or above, then the determination unit 320 does not excite the internal coil of the driving unit 434' of the attachment preventing means 400'. Therefore, the rod-like body 410' of the attachment preventing means 400' is kept projected along the tongue 11a, which disables the male part 11 of the seat belt to be inserted into the female part 12. Thus, when the seat belt cannot be fastened, the first start permission signal α is not outputted from the attachment sensing means 100 provided in the male part 11, and the start controlling means 200 does not put the motor 20 of the automobile 1 into the startable state, so that the driver cannot start the motor 20. Thus, the drunk driving of the driver can be effectively prevented.

On the other hand, if the determination unit 320 of the breath component concentration determining means 300 determines that the breath of the driver contains the alcohol of the reference value or above, the internal coil of the driving unit 433' of the locking mechanism 430' is excited, so that the locking of the rod-like body 410' by the locking mechanism 430' is released. The rod-like body 410' is thereby contained in the housing 401', allowing the male part 11 to be inserted into the female part 12. Then, if the male part 11 of the seat belt is not attached to the female part 12, the first start permission signal α is not outputted from the attachment sensing means 100 provided in the male part 11. Since the body controller 210 of the start controlling means 200 is configured to put the motor 20 of the automobile 1 into the startable state only when the first start permission signal α is inputted, the driver can be forced to wear the seat belt.

Additionally, the determination unit 320 of the breath component concentration determining means 300 functions as the driving controller 440' of the attachment preventing means 400'. Therefore, the number of parts can be reduced, thereby achieving cost reduction.

EMBODIMENT 8

Figure 30:
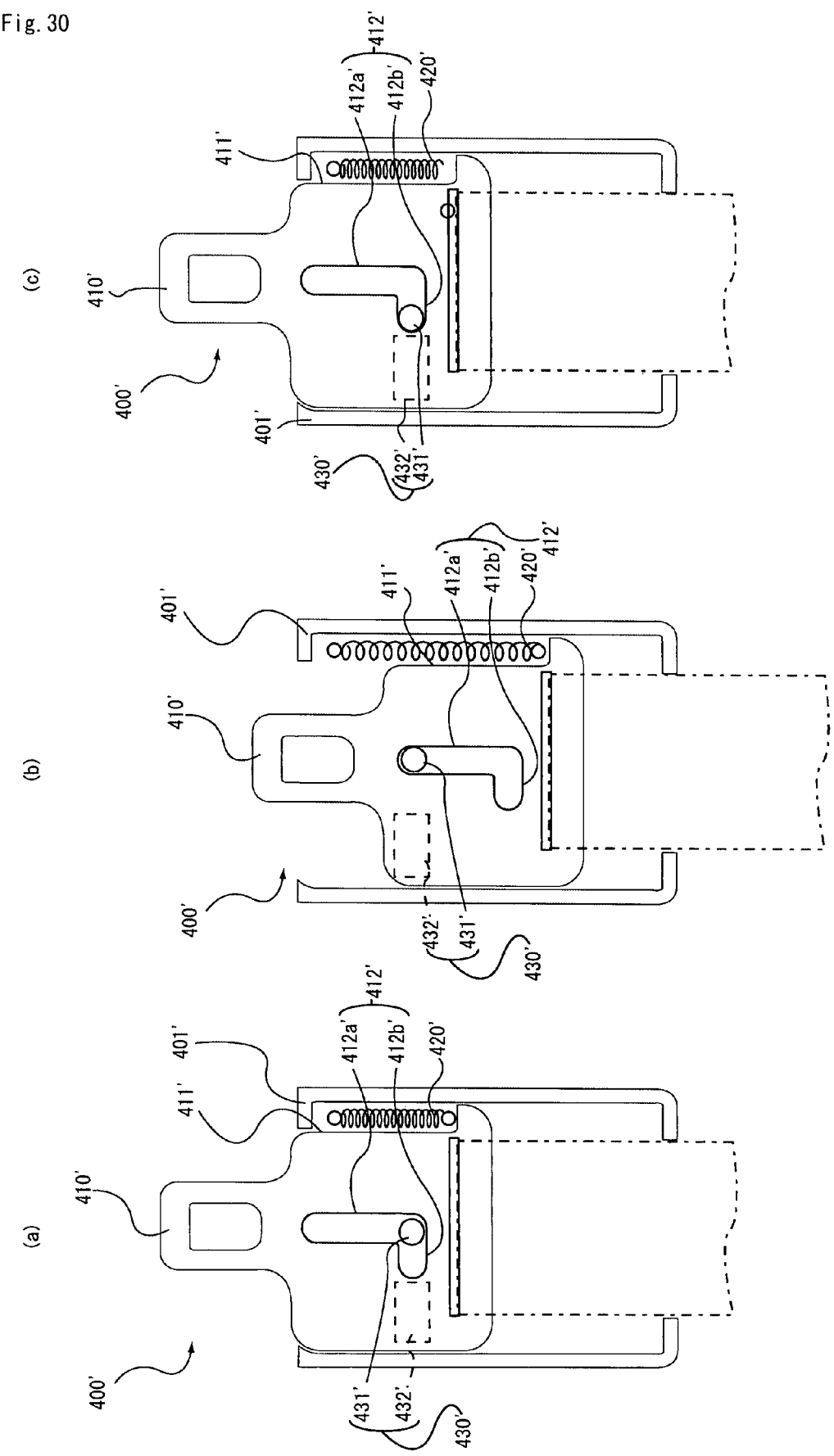
FIG. 30 is schematic cross-sectional views showing an internal structure of attachment preventing means of a safe-driving promotion system according to an eighth embodiment of the present invention, (a) being a view showing a projected and non-locked state of a tongue, (b) being a view showing a contained and non-locked state of the tongue, (c) being a view showing a locked state of the tongue.
Figure 31:
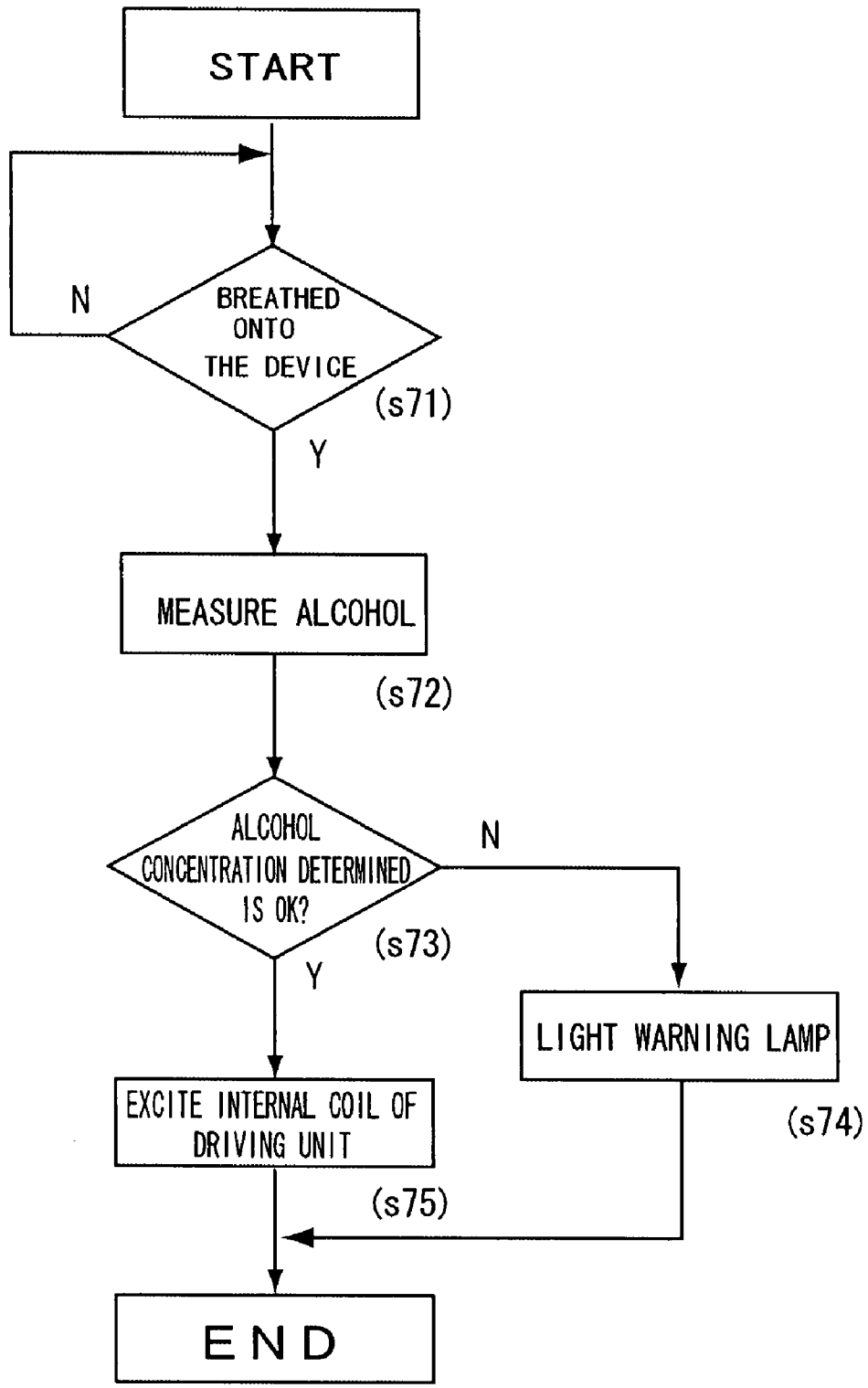
FIG. 31 is a flowchart of a fifth alcohol concentration determining program processed by a determination unit of breath component concentration determining means of the same system.

Next, referring to the drawings, a safe-driving promotion system according to an eighth embodiment of the present invention is described. FIG. 30 is schematic cross-sectional views showing an internal structure of attachment preventing means of the safe-driving promotion system according to the eighth embodiment of the present invention, (a) being a view showing a projected and non-locked state of a tongue, (b) being a view showing a contained and non-locked state of the tongue, (c) being a view showing a locked state of the tongue. FIG. 31 is a flowchart of a fifth alcohol concentration determining program which is processed by a determination unit of breath component concentration determining means of the same system.

The safe-driving promotion system described here is different from the safe-driving promotion system of Embodiment 5 in the configuration of the attachment preventing means 400'. Hereinafter, the different points are described in detail, and overlapping descriptions are omitted. Reference numeral 410' is given to a tongue, and the same reference numerals as those of Embodiment 5 are given to the other members.

The attachment preventing means 400', as shown in FIG. 30, has a housing 401' which is the housing of the male part 11 of the seat belt, a tongue 410' provided movably into and out of the housing 401', biasing means 420' for biasing the tongue 410' toward a direction in which the tongue 410' is projected from the housing 401', and the locking mechanism 430' for locking the tongue 410' in a projected state.

Inside of the housing 401', there is provided a guide (not shown) for holding the tongue 410' movably in the projecting direction.

The tongue 410' has cutaway part 411' in one widthwise end portion. Moreover, in a central portion of the tongue 410' is provided a substantially L-shaped groove part 412'. The groove part 412' has a first groove 412a' which is a long groove extending in the projecting direction of the tongue 410' and a second groove 412b' which is a long groove extending in a direction perpendicular to the first groove 412a'.

The biasing means 420' is a coil spring, whose one end portion is attached to the cutaway part 411' of the tongue 410', and whose other end portion is attached to the housing 401'.

The locking mechanism 430' has a locking bar 431' that movably fits into the groove part 412' of the tongue 410', and a driving unit 432' that moves the locking bar 431'.

The locking bar 431' is attached to a movable body of the driving unit 432'.

The driving unit 432' is a well-known solenoid in which by the excitation of an internal coil, the movable body is moved from a projecting position to a retracting position. When the movable body of the driving unit 432' is located in the projecting position, the locking bar 431' is located within the first groove 412a' of the groove part 412'. On the other hand, when the movable body of the driving unit 432' is located in the retracting position, the locking bar 431' is located within the second groove 412b' of the groove part 412'.

The breath component concentration determining means 300 is the same as in that of Embodiment 5 in the configuration, but is slightly different in the contents of the alcohol concentration determining program that the determination unit 320 processes.

Hereinafter, the usage of the safe-driving promotion system of the above-described configuration is described. Also described in detail are the contents of the fifth alcohol concentration determining program shown in FIG. 31 which is processed by the determination unit 320 of the breath component concentration determining means 300. Also, the operations of the respective units and parts are described.

First, when the seat belt of the automobile 1 has not been attached, as shown in FIG. 30(a), the movable body of the driving unit 432' of the locking mechanism 430' is located in the projecting position, and the locking bar 431' is located within the first groove 412a' of the groove part 412' of the tongue 410'. Therefore, the tongue 410' is now movable into or out of the housing 401' (i.e., in the non-locked state). Accordingly, even if the user attempts to attach the tongue 410' to the female part 12, as shown in FIG. 30(b), the tongue 410' is contained within the housing 401', which disables the tongue 410' to be attached to the female part 12. At this time, the biasing means 420' pulled between the tongue 410' and the housing 401' biases the tongue 410' in the direction in which the tongue 410' is projected from the housing 401' and returns the same to the projected state.

In starting the motor 20 of the automobile 1, the driver turns on the breath component concentration determining means 300. In response to this, the determination unit 320 of the breath component concentration determining means 300 processes the fifth alcohol concentration determining program as shown in FIG. 31.

Thereafter, the determination unit 320 determines whether or not sensing data of the sensing means 310 has been inputted (i.e., whether or not the sensing means 310 has been breathed on) (s71). As a result, if it is determined that the breathing has not been performed, the processing returns to step 71. On the other hand, if it is determined that the sensing data has been inputted and that the breathing has been performed, the alcohol concentration contained in the breath of the driver is measured based on the sensing data of the sensing means 310 (s72). The determination unit 320 determines whether or not a value of the measurement result (i.e., value of the alcohol concentration in the breath of the driver) is the reference value on a memory or above (s73). As a result, if it is determined that the value is the reference value or above, the determination unit 320 lights the warning lamp (s74), and finishes the processing of the fifth alcohol concentration determining program. On the other hand, if it is determined that the value of the measurement result is less than the reference value, the determination unit 320 excites the internal coil of the driving unit 432' of the attachment preventing means 400' for a predetermined time (s75). Thereafter, the processing of the fifth alcohol concentration determining program is finished.

When the internal coil of the driving unit 432' of the attachment preventing means 400' is excited, the movable body of the driving unit 432' moves from the projecting position to the retracting position. In response to this, as shown in FIG. 30(c), the locking bar 431' moves in the left direction in the figure so as to move from the first groove 412a' to the second groove 412b'. Therefore, the tongue 410' is locked in the projected state from the housing 401', which enables the tongue 410' to be attached to the female part 12.

Thereafter, when the driver attaches the tongue 410' to the female part 12, the first start permission signal α is outputted from the attachment sensing means 100 toward the start controlling means 200. Once the first start permission signal α is inputted, the body controller 210 of the start controlling means 200 puts the motor 20 into the startable state. This allows the driver to start the motor 20.

When the excitation of the internal coil of the driving unit 432' of the attachment preventing means 400' is stopped, the movable body moves from the retracting position to the projecting position. In response to this, the locking bar 431' moves in the right direction in the figure to move from the second groove 412b' to the first groove 412a'. That is, the tongue 410' returns to the non-locked state after a predetermined time.

In the case of the above-described safe-driving promotion system, if the determination unit 320 of the breath component concentration determining means 300 determines that the breath of the driver contains alcohol of the reference value or above, then the determination unit 320 does not allow the internal coil of the driving unit 432' of the attachment preventing means 400' to be excited. Therefore, the tongue 410' of the attachment preventing means 400' is kept in the non-locked state, which disables the tongue 410' to be attached to the female part 12. Thus, when the seat belt cannot be fastened, the first start permission signal α is not outputted from the attachment sensing means 100 provided in the male part 11, and the start controlling means 200 does not put the motor 20 of the automobile 1 into the startable state, so that the driver cannot start the motor 20. Thus, the drunk driving of the driver can be effectively prevented.

On the other hand, if the determination unit 320 of the breath component concentration determining means 300 determines that the alcohol of the reference value or above is not contained in the breath of the driver, the internal coil of the driving unit 432' of the locking mechanism 430' is excited, so that the locking mechanism 430' locks the tongue 410' in the projected state. This enables the tongue 410' to be attached to the female part 12. Then, if the tongue 410' is not attached to the female part 12, the first start permission signal α is not outputted from the attachment sensing means 100 provided in the male part 11. The body controller 210 of the start controlling means 200 is configured to put the motor 20 of the automobile 1 into the startable state only when the first start permission signal α is inputted, the driver can be forced to wear the seat belt.

Additionally, since the determination unit 320 of the breath component concentration determining means 300 functions as the driving controller 440' of the attachment preventing means 400', the number of parts can be reduced, thereby achieving cost reduction.

The attachment preventing means according to Embodiments 5, 6, 7 and 8 may have any configuration as long as the means prevents the attachment between the male part 11 and the female part 12 of the seat belt, and allows the male part 11 of the seat belt to be attached to the female part 12 in accordance with the result of the alcohol concentration determination of the breath component concentration determining means 300 (i.e., the result of determining whether the breath of the driver contains the alcohol of the reference value or above).

Moreover, although the driving unit of the attachment preventing means is described above as a solenoid or a magnet latch in which the movable body is operated by the excitation of the internal coil, the driving unit is not limited to such configuration, but may be of any kind that can operate the locking bar as described above. For example, as in Embodiment 2, the motor can be used and an eccentric cam or the like can be provided in the head part thereof to operate the locking bar. Obviously, as in Embodiment 2, a rack-and-pinion mechanism may be employed in the use of the motor. In these cases, the configuration can also be such that the determination unit 320 of the breath component concentration determining means 300 operates the motor in accordance with the result of the alcohol concentration determination of the breath component concentration determining means 300, thereby moving the locking bar to allow the male part 11 of the seat belt to be attached to the female part 12, and that thereafter, a predetermined time is counted in an internal timer circuit, and when the predetermined time has elapsed, the motor is operated in a reverse direction to return the locking bar to the initial position, thereby preventing the male part 11 of the seat belt to be attached to the female part 12.

Figure 32:
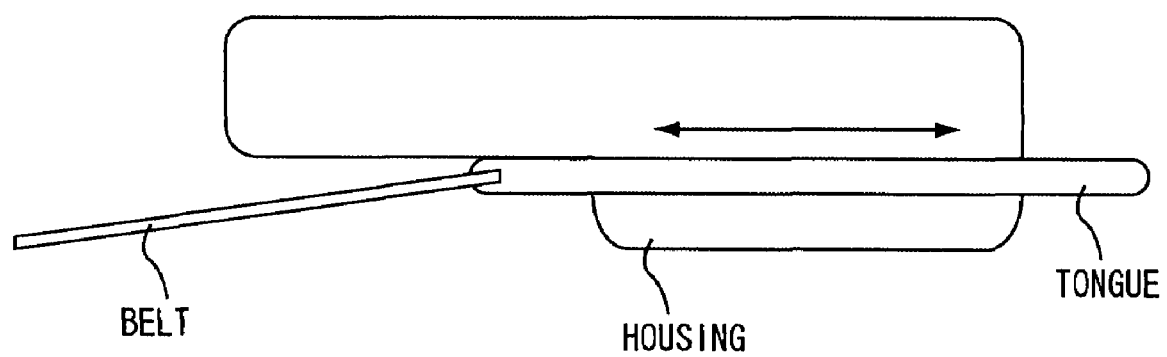
FIG. 32 is a schematic cross-sectional view showing a design modification of a housing of the attachment preventing means of the same system.

Moreover, any type of the housing of the attachment preventing means of the above-described embodiments may be used, as long as it can house the above-described respective means. However, as for the housing of Embodiment 8, considering that the belt of the seat belt is partially contained in the housing, such a configuration may be employed as to avoid the interference between the housing and the belt, or processing for reducing the frictional resistance may be applied to the contacting portion of the housing with the belt, lest at the time of an accident, the belt should be brought into contact with the housing, thereby increasing frictional resistance between both and causing the cut of the belt. An example of the former is shown in FIG. 32 where a belt deriving portion of the housing is cutaway to expose the belt. Obviously, the belt may be attached directly onto the housing of the attachment preventing means. FIG. 32 is a schematic cross-sectional view showing a design modification of the housing of the attachment preventing means of Embodiment 8.

Although it is described in the Embodiments 5, 6, 7 and 8 that the breath component concentration determining means is provided in the male part 11, it can be separately provided, or can be provided in a mobile telephone or the automobile 1. The same is true in the case where the biometric means 800 and/or the GPS transmitter 900 are provided together with the breath component concentration determining means. However, only the GPS transmitter 900 can be separated from the breath component concentration determining means 300 to be provided in the automobile 1.

Although the sensing means of the breath component concentration determining means is described above as means for sensing alcohol, the sensing means may be configured to sense drug. Obviously, the sensing means may be configured to sense both alcohol and drug.

Furthermore, in the case where the male part main body of the seat belt is curved so as to fit along the body of the driver (see FIG. 27), it is preferable that the gap between the male part main body and the housing of the attachment sensing means is filled with resin or another material. Obviously, the housing itself can be also formed into a shape conforming to the shape of the male part main body.

The contents of the above-described program are only examples, and any modification in design can be made as long as it can realize the similar functions.

Each of the above-described safe-driving promotion systems can be a safe-driving promotion device with the attachment sensing means and the start controlling means omitted. That is, the safe-driving promotion device has breath component concentration determining means for detecting alcohol and/or drug contained in the breath of a driver of an automobile and performing concentration determination of the alcohol and/or drug, and attachment preventing means for preventing the attachment between a male part and a female part of a seat belt, wherein the attachment preventing means is configured to allow the male part of the seat belt to be attached to the female part in accordance with a determination result of the breath component concentration determining means. Even with such safe-driving promotion device, similar effects as those of the above-described systems can be obtained if the device is incorporated in an automobile having a function of preventing a motor from starting when the seat belt is not attached, a warning function informing the driver of unattachment of the seat belt, or the like. It goes without saying that for the breath component concentration determining means and the attachment preventing means of the safe-driving promotion device, the configurations of the above-described embodiments can be employed.

A common seat belt normally has the female part provided in the automobile and the male part provided in the belt. However, it goes without saying that the male part may be provided in the automobile, and the female part may be provided in the belt.

The invention claimed is:

1. A safe-driving promotion system employed in an automobile, which is equipped with attachment sensing means for sensing that a male part of a seat belt of an automobile has been attached to a female part of the seatbelt and outputting a first start permission signal, and start controlling means for receiving the first start permission signal and putting a motor of the automobile into a startable state, the system comprising:
   breath component concentration determining means for detecting alcohol and/or drug contained in breath of a driver of the automobile and performing concentration determination of the alcohol and/or drug; and
   attachment preventing means for preventing attachment between the male part and the female part of the seat belt,
   wherein the attachment preventing means is configured to allow attachment of the male part of the seat belt to the female part in accordance with a determination result of the breath component concentration determining means.

2. The safe-driving promotion system according to claim 1, wherein the attachment preventing means is provided in the female part of the seat belt, and is configured to open and close an insertion slot of the female part for receiving the male part.

3. The safe-driving promotion system according to claim 1, wherein the attachment preventing means is provided in the female part of the seat belt, and is projectable and retractable within an insertion slot of the female part for receiving the male part.

4. The safe-driving promotion system according to claim 1, wherein the attachment preventing means is provided in the male part of the seat belt, and is projectable and retractable along an insertion part of the male part, the insertion part insertable into an insertion slot of the female part.

5. The safe-driving promotion system according to claim 1, wherein the attachment preventing means is configured such that an insertion part of the male part of the seat belt can move into and out of a male part main body.

6. The safe-driving promotion system according to claim 1, further comprising biometric means for reading physical characteristics of the driver to authenticate the driver,
   wherein the breath component concentration determining means is adapted to detect the alcohol and/or drug in the breath of the driver only when the biometric means determines that the driver is authentic.

7. The safe-driving promotion system according to claim 6, wherein the breath component concentration determining means is adapted to detect the alcohol and/or drug in the breath of the driver only within a predetermined period of time after the biometric means determines that the driver is authentic.

8. The safe-driving promotion system according to claim 1, wherein the breath component concentration determining means is separately provided from the attachment preventing means and the attachment sensing means.

9. The safe-driving promotion system according to claim 6, wherein the breath component concentration determining means is provided together with the biometric means, and is separately provided from the attachment preventing means and the attachment sensing means.

10. The safe-driving promotion system according to claim 1, wherein a global positioning system transmitter is provided in the male part or the female part of the seat belt.

11. The safe-driving promotion system according to claim 8, wherein the global positioning system transmitter is provided together with the breath component concentration determining means.

12. The safe-driving promotion system according to claim 8, wherein the breath component concentration determining means is incorporated in a mobile telephone.

13. The safe-driving promotion system according to claim 1, wherein the start controlling means is a body controller of an automobile for controlling the start of a motor of an automobile, so as to put the motor into the startable state only when receiving the first start permission signal.

14. The safe-driving promotion system according to claim 1, further comprising signal output means for outputting a second start permission signal to put a motor of an automobile into the startable state,
   wherein the start controlling means puts the motor of the automobile into the startable state only when receiving both of the first and second start permission signals.

15. The safe-driving promotion system according to claim 1,
   wherein the start controlling means comprises first blocking means that is adapted to open and close a keyhole of the automobile, and
   wherein the first blocking means opens the keyhole upon receiving the first start permission signal from the attachment sensing means.

16. The safe-driving promotion system according to claim 1, wherein the start controlling means is projectable and retractable within a keyhole of the automobile, and is configured to be retracted from a projected position with respect to the keyhole in response to the first start permission signal of the attachment sensing means.

17. The safe-driving promotion system according to claim 1, further comprising receiving means for receiving a second start permission signal for putting a motor of an automobile into the startable state, which is outputted from signal output means,
   wherein the start controlling means comprises second blocking means for openably blocking a receiving unit of the receiving means, and releases the receiving means in accordance with the first start permission signal of the attachment sensing means.

18. The safe-driving promotion system according to claim 1, further comprising a start operating unit operated to start the motor of the automobile, wherein the start controlling means comprises operation preventing means for preventing the operation of the start operating unit, and puts the start operating unit into an operable state in accordance with the first start permission signal of the attachment sensing means.

19. The safe-driving promotion system according to claim 18, wherein the start controlling means comprises third blocking means for openably blocking an operating surface of the start operating unit, and opens the start operating unit upon receiving the first start permission signal of the attachment sensing means.

20. The safe-driving promotion system according to claim 18, wherein the start operating unit is a push switch, wherein the start controlling means comprises engagement means for engagement with the start operating unit or a housing of an automobile where the start operating unit is provided, to prevent the pushing operation of the start operating unit, and, wherein, upon receiving the first start permission signal of the attachment sensing means, the start controlling means brings the engagement means out of engagement with the start operating unit or the housing of the automobile where the start operating unit is provided.

21. A safe-driving promotion device comprising:

breath component concentration determining means for detecting alcohol and/or drug contained in breath of a driver of an automobile and performing concentration determination of the alcohol and/or drug; and attachment preventing means for preventing attachment between a male part and a female part of a seat belt, wherein the attachment preventing means is configured to allow attachment of the male part of the seat belt to the female part in accordance with a determination result of the breath component concentration determining means.

* * * * *